US006333406B1

(12) United States Patent
Inselburg et al.

(10) Patent No.: US 6,333,406 B1
(45) Date of Patent: Dec. 25, 2001

(54) **GENE ENCODING PROTEIN ANTIGENS OF *PLASMODIUM FALCIPARUM* AND USES THEREFOR**

(76) Inventors: Joseph W. Inselburg, 26 Rayton Rd., Hanover, NH (US) 03755; David J. Bzik, Box 1064, Grantham, NH (US) 03753; Toshihiro Horii, Higashitoyonaka-cho 2-12-1, 402; Tomohiko Sugiyama, Shibara-cho 5-2-1, 206, both of Toyonaka Osaka 560 (JP)

( * ) Notice: Subject to any disclaimer, the term of this patent is extended or adjusted under 35 U.S.C. 154(b) by 0 days.

(21) Appl. No.: 08/213,419

(22) Filed: Mar. 14, 1994

Related U.S. Application Data

(63) Continuation-in-part of application No. 07/870,806, filed on Apr. 17, 1992, now abandoned, which is a continuation of application No. 07/231,771, filed on Aug. 12, 1988, now abandoned.

(51) Int. Cl.[7] .......................... C07H 21/02; C07H 21/04; C12N 15/30; A61K 39/015

(52) U.S. Cl. .................. 536/23.7; 424/191.1; 424/268.1; 424/272.1; 435/69.3; 435/69.7; 435/70.1; 435/71.1; 435/320.1; 435/455; 435/471; 435/325; 435/243; 514/44; 536/23.5

(58) Field of Search ...................................... 530/350, 387, 530/820, 806; 436/517; 514/2, 12, 44; 424/88, 191.1, 268.1, 272.1; 435/69.7, 71.1, 320.1, 455, 471, 325, 243, 69.3, 70.1; 536/23.5, 23.7

(56) References Cited

U.S. PATENT DOCUMENTS

| | | | |
|---|---|---|---|
| 4,735,799 | 4/1988 | Patarroyo | 424/88 |
| 4,767,622 | 8/1988 | Ristic et al. | 424/88 |
| 4,906,564 | 3/1990 | Lyon et al. | 435/7 |
| 4,978,621 | * 12/1990 | Ardeshir et al. | 435/243 |
| 5,028,425 | 7/1991 | Good et al. | 424/88 |
| 5,194,587 | * 3/1993 | Knapp et al. | 530/324 |

FOREIGN PATENT DOCUMENTS

| | | |
|---|---|---|
| 0 154 454 | 9/1985 | (EP) . |
| 0 283 882 | 9/1988 | (EP) . |
| WO 87/00533 | 1/1987 | (WO) . |
| WO 87/03882 | 7/1987 | (WO) . |

OTHER PUBLICATIONS

Knapp et al., "Molecular Cloning, genomic structures and localization in a blood stage antigen of *Plasmodium falciparum* characterized by a serine stretch," *Molecular and Biochemical Parasitology*, 32(1989) 73–84.*

Maniatis et al., *Molecular Cloning: A Laboratory Manual* (Cold Spring Harbor Laboratory 1982); Chapter 10, pp. 310–361.*

Banyal, H.S. and J. Inselburg, "Isolation and Characterization of Parasite–Inhibitory *Plasmodium falciparum* Monoclonal Antibodies" *Am J. Trop. Med. Hyg.*, vol. 34, No. 6, pp. 1055–1064, 1985.

Bhatia, A. et al., "Immunochemical Analysis of a Major Antigen of *Plasmodium falciparum* (p126) Among Ten Geographic Isolates" *Am. J. Trop. Med. Hyg.*, vol. 36, No. 1, pp. 15–19, 1987.

Chulay, J.D. et al., "Monoclonal Antibody Characterization of *Plasmodium falciparum* Antigens in Immune Complexes Formed When Schizonts Rupture in the Presence of Immune Serum" *J. Immunology*, vol. 139, pp. 2768–2774, 1987.

Delplace, P. et al., "Localization, biosynthesis, processing and isolation of a major 126 kDa antigen of the parasitophorous vacuole of *Plasmodium falciparum*" *Molecular and Biochemical Parasitology*, vol. 23, No. 3, pp. 193–201, 1987.

Horii, T. et al., "Characterization of antigen–expressing *Plasmodium falciparum* cDNA clones that are reactive with parasite inhibitory antibodies", *Mol. Biochem. Parasitol.*, vol. 30, pp. 9–18, 1988.

Inselburg, J. et al., "Protective Immunity in *Aotus* Monkeys by a Recombinant SERA Protein of *Plasmodium falciparum*: Adjuvant Effects on Induction of Protective Immunity" *Infection and Immunity*, vol. 61, No. 5, pp. 2041–2047, May 1993.

Inselburg, J. et al., "Protective Immunity Induced in *Aotus* Monkeys by a Recombinant SERA Protein of *Plasmodium falciparum*: Further Studies Using SERA 1 and MF75.2 Adjuvant" *Infection and Immunity*, vol. 61, No. 5, pp. 2048–2052, May 1993.

Inselburg, J. et al., "Protective Immunity in *Aotus* Monkeys by Recombinant SERA Proteins of *Plasmodium falciparum*" *Infection and Immunity*, vol. 59, No. 4, pp. 1247–1250, Apr. 1991.

(List continued on next page.)

*Primary Examiner*—Christopher L. Chin
*Assistant Examiner*—James L. Grun
(74) *Attorney, Agent, or Firm*—Lahive & Cockfield, LLP; Giulio A. DeConti, Jr, Esq.; Megan E. Williams, Esq.

(57) ABSTRACT

A *Plasmodium falciparum* gene encoding immunogenic SERA protein has been isolated by a) systematically screening a lambda gt11 recombinant DNA expression library with a murine monoclonal antibody directed against protein antigens of this pathogen, and b) systematically screening a lambda gt11 genomic cDNA and oligonucleotide probes directed against this pathogen. A 111 kDa protein has been shown to have immunogenic activity against parasite inhibitory antibodies. The gene encoding this protein, including the signal sequence and regulatory sequence in the adjacent 5' flanking sequence has been isolated and sequenced.

Isolation and characterization of genes encoding major protein antigens of *P. falciparum* make it possible to develop reagents useful in the diagnosis, prevention and treatment of malaria. In addition, the signal sequences or regulatory sequences of this gene can be used to stimulate the production of other useful genetic products.

13 Claims, 26 Drawing Sheets

OTHER PUBLICATIONS

Kemp, D.J. et al., "Expression of *Plasmodium falciparum* blood–stage antigens in *Escherichia coli*: Detection with antibodies from immune humans" *Proc. Natl. Acad. Sci. USA*, vol. 80, pp. 3787–3791, Jun. 1993.

Perrin, L.H. et al., "Antimalarial Immunity in Saimiri Monkeys: Immunization with Surface Components of Asexual Blood Stages" *J. Exp. Med.*, vol. 160, pp. 441–451, Aug. 1984.

Weber, J.L. et al., "Blood Stage Antigen Genes of *Plasmodium falciparum*" in *Molecular Strategies of Parasitic Invasion*, New York: Alan R. Liss, Inc., pp. 379–388, 1987, from the Proceedings of a MacArthur Foundation–UCLA Symposium, Utah, Jan. 26–31, 1987.

* cited by examiner

```
First nt.        10         20         30         40         50         60         70         80         90        100
   +1  AAAATACATA TATTATAACA TAAAGAAAAA TTAAATAAAT CAAACATATT CAAAAAAATT AAAGTTCTTA AAATATTATA TAACTTAATA CTCATATATC
 +101  AAAATGAAGT CATATATTTC CTTGTTTTTC ATATTGTGTG TTATATTTAA CAAAAATGTT ATAAAAATGA CAGGAGAAAG TCAAACAGGT AATACAGGAG
 +201  GAGGTCAAGC AGGTAATACA GTAGGAGATC AAGCAGGTAG TACAGGAGGA AGTCCACAAG GTAGTACGGG AGCAAGTCAA CCCGGAAGTT CCGAACCAAG
 +301  CAATCCTGTA AGTTCCGGAC ATTCTGTAAG TACTGTATCA GTATCACTTC CTTCAACTTC TTCAGAAAAA CAGGATACAA TTCAAGTAAA ATCAGCTTTA
 +401  TTAAAAGATT ATATGGGTTT AAAAGTTACT GGTCCATGTA ACGAAAATTT TTAGTTCCTC TTAGTTCAA ACAGTGGTTC ATATATATAT ACAGAAGATA
 +501  CTAATATCGA ATTAAGAACA ACATTGAACA AACAAATAA TGCAATATCA TTTGAATCAA ACAGTGGTTC ATTAGAAAAA AAAAAAATAT TAAAACTACC
 +601  ATCAAATGGT ACAACTGGTG AACAAGGTTC AAGTACGGGA ACAGTTAGAG AGAGATACAGA ACCAATTTCA GATTCAAGCT CAAGTCAAG TTCAAGTTCT
 +701  AGTTCAAGTT CAAGTTCAAG TTCTAGTTCA CCGCCAAGAA ATTTACAAAG CAAGTTCAAG TTCTAGTTCA ACTGGAAAA AAGTCTTCCT GCTAATGGAC
 +801  CTGATTCCCC TACTGTTAAA CCGCCAAGAA ATTTACAAAG TATATGTGAA ACTTCAAGTT AAGAAAGTAT ATTAAGGAGA ATACATTAAT
 +901  AATTAAATGG AAAGTATACG GAGAATAAAC ACAAAATAAA GATATTGATG AAGTTGATGT TTGATAAATG TACGCATTAG GATCAGACAT AAAAGGAAAC CCCATTTACT
+1001  AGTATACTAA TACATGCGTA TAAAGAACAA AATGGAACAA TTAATTGTTA AGTGCTTC TTTTAGTAGA AAAAGAAAAT AAAAATGACG TATGTTACAA TGTGATACCT
+1101  TAGCTTCCAA TTGCTTTTTA AGTGTAATT TTACATTGA CAAAGAAATA AAAGCTGAGA TGATGAAGAT GATTATACTG AATATAAATT AACAGAATCT
+1201  ATACCTATCT GAAGATATTG TAAGTAACTT CAAAGAAATA ATAATGAAAA ATCAGAATTA AAGAAGTAGA TTTATAATG ATATTAGTTG AAATTAGAAT
+1301  ATTGATAATA TATTAGTAGA AATGTTTCTG ACAAATGAAA AGTACCTTA GATAATTATG GGATGGAAA TGAATGGAT ATATTAATA ACTTAAAGAG
+1401  TAATGAATTA CTGTAGTTA CTTAAAGACG TAGATACAAC TAGATACTTTA AAAAATAAAT AGCTGTATGT CTTAAAAATG TTGATGATTG GATTGTAAAT
+1501  ATTATTAATT TATCATTCAG AAGAAAATAT TAATACTTTA AAAAATAAAT AATATTTCAA TATAATGATA AAAATTCTCC AGAAGATAAA GATAATAAAG
+1601  AAGAGAGGTT TAGTATTACC TGAATTAAAT TATGATTTAG TAGAAAAAGA AGATACTTTA TCATATGATA ACTTCATGG AATAAAGAAT ATTGTAACAG
+1701  GAAAATGTGT CGTACATGTT GATACAACTT GTATATCTAA TCTTCAAGTT GAAGATCAAG CTAATTGTGA TACTTCATGG CAAAATATCA TTTAGAAACT
+1801  ATTAAAAGAT GAAAATAAAT GTATATCTAA TCTTCAAGTT GAAGATCAAG CTAATTGTA ACATAAAGA TAGATGTGAT GAAGGTTCTA
+1901  ATTAGATGTA TGAAAGGATA TGAACCTACC AAAATTCTG ATTATGGATT CTTACCAGCA GAATCAAATT AGCTAATGT TATAAAGGTG AATGTCCAAA
+2001  GTCCAATGGA ATTCTTACAA ATTCTTGAAG ATTAGGAATT CTTACCAGCA GAATCAAATT AGCTATAAGA CTATGTGAAA GTTGGAGAAC TGCATATGAA
+2101  GGTAGAAGAT CACTGGATGA ATCATGGGA TAATGGAAAA ATCCTTACACA ATCCTTACACA AACATAAAGA TTAGATGGTA AGGGATATAC TGCATATGAA
+2201  AGTGAAAGAT TTCATGATAA TATGGATGCA TTTGTTAAAA TTTAAAAGTT CAGTTATTGC AATATATTAA GCTAAAAGTT ATTATGTGAA
+2301  TTATGGGATA TGAATTTAGT GGAAAGAAAG TACAGAACTT ATGTGGTGAT GTAAGTAATG GATACAGCTG GGTTATGGTA AGATATTGGAA
+2401  TAGCGAAGGA GAAAAAAAAT CCTATTGGAT TGTAAGAAAC AGTTGGGGTC CATATTGGGG AGATGAAGGT AGATATGTA TAGATATGTA TGGACCAACT
```

Fig. 2

```
+2501 CATTGTCATT TTAACTTTAT TCACAGTGTT GTTATATTCA ATGTTGATTT ACCTATGAAT AATAAAACAA CTAAAAAAGA ATCAAAAATA TATGATTATT
+2601 ATTTAAAGGC CTCTCCAGAA TTTTATCATA ACCTTTACTT TAAGAATTTT AATGTTGGTA AGAAAAATTT ATTCTCTGAA AAGGAAGATA ATGAAAACAA
+2701 CAAAAATTA GGTAACAACT ATATTATATT CGGTCAAGAT ACGGCAGGAT CAGGACAAAG TGGAAAGGAA AGCAATACTG CATTAGAATC TGCAGGAACT
+2801 TCAAATGAAG TCTCAGAACG TGTTCATGTT TATCACATAT AAAACATAT TAAAATAAGA TGGGTATGCG TAAATATATA GATACACAAG
+2901 ATGTAAATAA GAAACATTCT TGTACAAGAT CCTATGCATT AATTATGAAA AATGTGTAAA TTTATGTAAT GTGAACTGGA AACATGCGA
+3001 GGAAAAAACA TCACCAGGAC TTTGTTTATC CAAATTGGAT ACAAATAACG AATGTTATT CTGTTATGTA TAAAATAATA TAACAAAAAA AAAAAAAAAA
+3101 AAAAAAA
```

Fig. 2 (continued)

MKSYISLFFI LCVIFNKNVI KCTGESQTGN TGGGQAGNTV GDQAGSTGGS
PQGSTGASQP GSSEPSNPVS SGHSVSTVSV SQTSTSSEKQ DTIQVKSALL
KDYMGLKVTG PCNENFIMFL VPHIYIDVDT EDTNIELRTT LKETNNAISF
ESNSGSLEKK KYVKLPSNGT TGEQGSSTGT VRGDTEPISD SSSSSSSSSS
SSSSSSSSSS SSSSSSSSSS SSSSSESLPA NGPDSPTVKP PRNLQNICET
GKNFKLVVYI KENTLIIKWK VYGETKDTTE NNKVDVRKYL INEKETPFTS
ILIHAYKEHN GTNLIESKNY ALGSDIPEKC DTLASNCFLS GNFNIEKCFQ
CALLVEKENK NDVCYKYLSE DIVSNFKEIK AETEDDDEDD YTEYKLTESI
DNILVKMFKT NENNDKSELI KLEEVDDSLK LELMNYCSLL KDVDTTGTLD
NYGMGNEMDI FNNLKRLLIY HSEENINTLK NKFRNAAVCL KNVDDWIVNK
RGLVLPELNY DLEYFNEHLY NDKNSPEDKD NKGKGVVHVD TTLEKEDTLS
YDNSDNMFCN KEYCNRLKDE NNCISNLQVE DQGNCDTSWI FASKYHLETI
RCMKGYEPTK ISALYVANCY KGEHKDRCDE GSSPMEFLQI IEDYGFLPAE
SNYPYNYVKV GEQCPKVEDH WMNLWDNGKI LHNKNEPNSL DGKGYTAYES
ERFHDNMDAF VKIIKTEVMN KGSVIAYIKA ENVMGYEFSG KKVQNLCGDD
TADHAVNIVG YGNYVNSEGE KKSYWIVRNS WGPYWGDEGY FKVDMYGPTH
CHFNFIHSVV IFNVDLPMNN KTTKKESKIY DYYLKASPEF YHNLYFKNFN
VGKKNLFSEK EDNENNKKLG NNYIIFGQDT AGSGQSGKES NTALESAGTS
NEVSERVHVY HILKHIKDGK IRMGMRKYID TQDVNKKHSC TRSYAFNPEN
YEKCVNLCNV NWKTCEEKTS PGLCLSKLDT NNECYFCYV*

```
GTAAAAATATAATTATTATATAATAATAATATAAATATAATATTTTACGCATACACAAACATTTGCATTATTTTTTTTAGGTGTTATATTAACAAAAATGTTATAAAATGTACGGAGAAA 2640
------------------------------------------------------------------------------------ysValIlePheAsnLysAsnValIleLysCysThrGlyGlus 26

GTCAAACAGGTAATACAGGAGGAGTCAAGCAGGTAATACAGTAGGAGATCAAGCAGGTAGTACGGAGCAGTCCACAAGGTACGGAGGAGCAAGTCAACCCGGAAGTTCCGAACCAA 2760
erGlnThrGlyAsnThrGlyGlyGlyGlnAlaGlyAsnThrValGlyAspGlnGlySerThrGlyAlaSerGlnProGlnGlySerProGlnGlySerProGlySerGluPros 66

GCAATCCTGTAAGTTCCGGACATTCTGTAAGTACTGTATCAGTAGTACTGTATCAGTAGTACTCAACTTCTCAGAAAAACAGGATAACAATTCAAGTAAAATCAGCTTTATTAAAGATTATAATGGGTT 2880
erAsnProValSerSerGlyHisSerGlyValSerThrValSerGlnThrSerSerGlyHisSerThrSerSerGluLysGlnThrIleGlnValLysSerAlaLeuLeuLysAspTyrMetGlyL 106

TAAAAGTTACTGGTCCATGTAACGAATAAAATTTCATAATGTTCCTAGTTCCTCATATATATATTGATCTTGATACAGAAGATACTAATATCGAATTGAAAGAACAACATTGAAAGAAACAAATA 3000
euLysValThrGlyProCysAsnGluAsnPheIleMetPheLeuValProHisIleTyrIleAspThrGluAspThrGluAspValAspThrGluAspThrLeuLysGluThrAsnA 146

ATGCAATATCATTGAATCAAAACAGTGGTTCATTAGAAAAAAAAAATATGTAAAACTACCATCAAAATGGTACAACAGTTCAAGCTGTGAACAAGTTCAAGTTCAAGTTCAAGTACGGGAACAGTTACAGGAGATACAG 3120
snAlaIleSerPheGluSerAsnSerGlySerLeuGluGluLysGluLysLysLysTyrValLysLeuProSerAsnGlyThrThrGlyGluGlnGlySerThrGlyThrGlyThrGlyAspThrG 186

AACCAATTTCAGATTCAAGCTCAAGTTCAAGTTCTAGTTCAAGTTCAAGTTCAAGTTCTAGTTCAAGTTCAAGTTCAAGTTCAAGTTCAGTTCAGTTCAAGTTCAG 3240
luProIleSerAspSerSerSerSerSerSerSerSerSerSerSerSerSerSerSerSerSerSerSerSerSerSerSerSerSerSerSerSerSerSerSerSerG 226

AAAGTCTTCCTGCTAATGACCTCATTCCCTACTGTTAAACCGCCAAGAAATTACAAAAATATATGTGAAAACTTCAAGTTGGTAGTATATATTAAGGAGAATACATTAA 3360
luSerLeuProAlaAsnGlyProAspSerProThrValLysProProArgAsnLeuGlnAsnIleCysGluThrGlyLysAsnPheLysValTyrIleLysGluAsnThrLeuI 266

TAATTAAATGAAAGTATACGGAGAACAAAAGATACTACTGAAAGTATAAAAAAAATAACCGAATAAAACAATAATAATAAATACTTTTTCTTTTTTTGATTGATTATTTTATATTTTTCAT 3480
leIleLysTrpLysValTyrGlyValTyrGlyGluThrLysAspThrThrGluA---------------------------------------------------------- 281

AAGAAAAATGTCATTATCATACAACTACTACATCAATATGTATATTTTGTATTATTTTATATTATTTATTATTTATTATTATTATTATTTAGATAACAAAGTTGATGTAACA 3600
------------------------------------------------------------------snAsnLysValAspValArg 287
```

```
GGATTCTTACCAGCAGAATCAAATTATCCATATAACTATGTGAAAGTTGGAGAACAATGTCCAAAGGTAGAAGATCACTGGATGAATCTATGGATAATGGAAAAAATCTTACATAACAAA  4920
GlyPheLeuProAlaGluSerAsnTyrProTyrAsnTyrValGlyGluGlnCysProLysValGlyGluTrpMetAsnLeuTrpAspAsnGlyLysIleLeuHisAsnLys             684

AATGAACCTAATAGTTTAGATGGTAAGGATATACTGCATATGAAACTGAAAGATTTCATGATAATATGGATGCATTGTTAAAATTATTAAAACTGAAGTAATGAATAAAGGTTCAGTT   5040
AsnGluProAsnSerLeuAspGlyLysGlyTyrThrAlaTyrGluArgPheHisAspAsnMetAspAlaPheValLysIleIleLysThrGluValMetAsnLysGlySerVal           724

ATTGCATATATTAAAGCTGAAAATGTTATGGATATGAATTTACTGGAAAGAAAGTACAGAGAACTTATGTGGTGATGATACAGCTGATCATGCAGTTAATATTGTTGGTTATGGTAATTAT   5160
IleAlaTyrIleLysAlaGluAsnValMetGlyTyrGluPheSerGlyLysTyrArgGluLeuMetValAspAspThrAlaAspHisAlaValAsnIleValGlyTyrGlyAsnTyr       764

GTGAATAGCGAAGGAGAAAAAAAATCCTATTGGATTGTAAGAACAGTGGGGTCCATATTGGGAGATGAAGGTTATTTAAAGTAGATATGTGACCAACTCATTGTCATTTAAC           5280
ValAsnSerGluGlyGluLysLysLysSerTyrTrpIleValArgAsnSerTrpGlyProTyrTrpGlyAspGlyTyrPheLysValAspMetTyrGlyProThrHisCysHisPheAsn   804

TTTATTCACAGTGTTGTTATATTCAATGTGATTACCTATGAATAATCAAAAATATAGAATCAAAAATATATGATTATTATTAAAGGCCTCCAGAATTTTATCATAACCTT             5400
PheIleHisSerValValIleAsnValAspLeuProMetAsnLysThrThrLysLysIleSerLysIleTyrAspTyrLeuLysAlaSerProGluPheTyrHisAsnLeu             844

TACTTTAAGAATTTTAATGTGGTAAGAAAAATTATTCTCGAAAAGGAAGATAATGAAAACAAACAAAAAATTAGTAACAACTATATATTCGGTCAAGATACGGCAGGATCAGGA         5520
TyrPheLysAsnPheAsnValGlyLysAsnLeuPheSerGluLysLysAsnLeuPheLysAsnAsnTyrIleIlePheGlyLysAsnAspThrAlaGlySerGly                   884

CAAAGTGGAAAGGAAAGCCAATACTGCATTAGAATCTGCAGGAACTTCAAATGAAGTCTCAGAAGCTGTTCATGTTTATCACAATTAAAACATATAAAGGATGGCAAAATAAGAATGGGT   5640
GlnSerGlyLysGlySerAsnThrAlaLeuGluSerAlaGlyThrSerGluAsnGluValSerGluValHisValTyrHisIleLeuLysHisIleLysAspGlyLysIleArgMetGly     924

ATGCGTAAAATATAGATACAAGATGTAAATACAACATTCTTGTACAAGATCCATGCATTAATCCACAAGAATTATGAAAAATGTGTAAATTATCTAATGTGAACTGGAAAACA         5760
MetArgLysTyrIleAspThrArgGlnAspValAsnLysHisSerCysThrArgSerTyrAlaPheAsnProGluAsnTyrGluLysCysAsnLeuCysAsnValAsnTrpLysThr       964

TGCGAGCAAAAAACATCACCAGGACTTTGTTTATCCAAATTGGATACAAATAACGAAGTTATTCTGTATGTATAAAATAACAAAAAATAATAACAAAAAAATATTTTTTTTATT        5880
CysGluGluLysThrSerProGlyLeuCysLeuSerLysAspThrAsnAsnGluCysTyrPheCysTyrVal***                                                   989

GTATCCTTTAATTTTAAATAGGGCATAAACTCTCCATTATTCATTTTATTAAGGTAGTAATAATATCTTTAATTTATCATGTACCTCTATAAATATATATAAATTATAATTATATTATT     60
TTTTTTTTTAAGAATTATTTTTATTCATGTAAATATAATATTCTTTTTTTTTTTTTTTTAAAAAAAAAATACACGATAGTTGTACATTAAATGTACAATTATATTAACTCGA           6120
ATTC                                                                                                                        6124
```

Fig. 6 (continued)

```
            probe A                                  HinfI
         GGGAACAGTTAGAGGAGATACAG AACCAATTTCA GATTC
```

```
Allele I:    AACAAGGTT CAAGTAC AAGCTCAAGTTCAA   3150
Allele II:   AACAAAGTTCTAGTTCAAGTTCAAGTTCTA
                  probe B Allele I:    GTTCAAGTTCTAGTTCAAGTTCAAGTTCAA   3180
Allele II:   GTTCAAATTCTAGTTCAAGTTCAAGTTCAA Allele I:    GTTCTAGTTCAAGTTCAAGTTCAAGTTCAA   3210
Allele II:   GTTCAAGTTCTAGTTCAAGTTCAAGTTCAA Allele I:    GTTCTAGTTCAAGTTCAAGTTCAAGTTCAG   3240
Allele II:   GTTCTAGTTCAAGTTCAAGTTCAAGTTCAG
```

Fig. 7

DNA and deduced amino-acid sequence of SE47'

```
5'-ATG AAA AAC GTG ATC AAA TGT ACC GGT GAA AGC CAG ACC GGT AAT ACC GGC GGT
   Met Lys Asn Val Ile Lys Cys Thr Gly Glu Ser Gln Thr Gly Asn Thr Gly Gly

GGT CAG GCA GGC AAC ACG GTT GGC GAC CAG GCG GGC TCT ACC GGC GGC TCT CCG
   Gly Gln Ala Gly Asn Thr Val Gly Asp Gln Ala Gly Ser Thr Gly Gly Ser Pro

CAG GGT AGC ACA GGC GCC AGT CAA CCC GGC TCT AGC GAA CCG TCT AAC CCA GTG
   Gln Gly Ser Thr Gly Ala Ser Gln Pro Gly Ser Ser Glu Pro Ser Asn Pro Val

TCT TCT GGC CAT TCT GTT AGT ACC GTT AGC GTT AGC CAG ACC AGC ACC TCT TCT
   Ser Ser Gly His Ser Val Ser Thr Val Ser Val Ser Gln Thr Ser Thr Ser Ser

GAA AAA CAA GAT ACC ATT CAG GTG AAA TCT GCG CTG CTG AAA GAT TAT ATG GGT
   Glu Lys Gln Asp Thr Ile Gln Val Lys Ser Ala Leu Leu Lys Asp Tyr Met Gly

TTA AAA GTT ACG GGC CCG TGT AAC GAA AAT TTC ATC ATG TTC CTG GTT CCG CAT
   Leu Lys Val Thr Gly Pro Cys Asn Glu Asn Phe Ile Met Phe Leu Val Pro His

ATT TAT ATT GAT GTG GAT ACC GAA GAT ACC AAT ATA GAG CTC CGT ACC ACC CTG
   Ile Tyr Ile Asp Val Asp Thr Glu Asp Thr Asn Ile Glu Leu Arg Thr Thr Leu

AAA GAA ACC AAC AAC GCG ATC TCA TTT GAA TCA AAC AGT GGT TCA CTG GAA AAA
   Lys Glu Thr Asn Asn Ala Ile Ser Phe Glu Ser Asn Ser Gly Ser Leu Glu Lys

AAA AAA TAT GTG AAG CTT CCG TCA AAC GGC ACC ACC GGT GAA CAG GGT TCA AGT
   Lys Lys Tyr Val Lys Leu Pro Ser Asn Gly Thr Thr Gly Glu Gln Gly Ser Ser

ACA GGC ACC GTT CGC GGC GAT ACC GAA CCG ATT TCA GAC TCG AGT AGC TCT TCG
   Thr Gly Thr Val Arg Gly Asp Thr Glu Pro Ile Ser Asp Ser Ser Ser Ser Ser

TCC AGT TCA AGC TCC TCT AGC TCG TCA TCT AGC TCG TCT AGC AGT TCA TCC AGC
   Ser Ser Ser Ser Ser Ser Ser Ser Ser Ser Ser Ser Ser Ser Ser Ser Ser Ser

AGT TCT AGC TCG TCC TCT AGT TCC AGC TCA TCG AGC GAA AGT CTT CCG GCG AAT
   Ser Ser Ser Ser Ser Ser Ser Ser Ser Ser Ser Glu Ser Leu Pro Ala Asn

GGC CCG GAT TCC CCG ACC GTT AAA CCC CCG CGT AAC CTG CAG AAC ATC TGT GAA
   Gly Pro Asp Ser Pro Thr Val Lys Pro Pro Arg Asn Leu Gln Asn Ile Cys Glu

ACC GGC AAA AAC TTC AAA CTG GTG GTG TAT ATT AAG GAG AAT ACA TTA ATC ATT
   Thr Gly Lys Asn Phe Lys Leu Val Val Tyr Ile Lys Glu Asn Thr Leu Ile Ile

AAA TGG AAA GTG TAC GGC GAA ACC AAA GAT ACC ACC GAA AAT AAC AAA GTG GAC
   Lys Trp Lys Val Tyr Gly Glu Thr Lys Asp Thr Thr Glu Asn Asn Lys Val Asp

GTA CGC AAG TAT CTG ATT AAC GAA AAG GAA ACC CCG TTT ACT AGT ATT CTA ATC
   Val Arg Lys Tyr Leu Ile Asn Glu Lys Glu Thr Pro Phe Thr Ser Ile Leu Ile

CAT GCA TAT AAA GAA CAT AAT GGC ACC AAC CTG ATC GAA AGT AAA AAC TAC GCG
   His Ala Tyr Lys Glu His Asn Gly Thr Asn Leu Ile Glu Ser Lys Asn Tyr Ala

CTG GGC TCA GAC ATT CCG GAA AAA TGT GAT ACC CTG GCG TCC AAT TGC TTT CTG
   Leu Gly Ser Asp Ile Pro Glu Lys Cys Asp Thr Leu Ala Ser Asn Cys Phe Leu

AGT GGT AAC TTT AAC ATT GAA AAA TGC TTT CAG TGC GCG CTG CTG GTG GAA AAA
   Ser Gly Asn Phe Asn Ile Glu Lys Cys Phe Gln Cys Ala Leu Leu Val Glu Lys

GAA AAT AAA AAC GAC GTG TGT TAC AAA TAC CTA AGC GAA GAT ATT GTG TCT AAT
   Glu Asn Lys Asn Asp Val Cys Tyr Lys Tyr Leu Ser Glu Asp Ile Val Ser Asn

TTC AAG GAG ATC AAA GCG GAG TAA 3'
   Phe Lys Glu Ile Lys Ala Glu ***
```

Fig.11

DNA and deduced amino-acid sequence of SE50A

```
5'-ATG AAA GAT GAA AAC AAC TGC ATT TCG AAC CTG CAG GTG GAA GAT CAG GGT AAC
   Met Lys Asp Glu Asn Asn Cys Ile Ser Asn Leu Gln Val Glu Asp Gln Gly Asn

TGC GAT ACC AGC TGG ATC TTC GCT AGC AAG TAT CAT CTG GAA ACC ATT CGT TGT
   Cys Asp Thr Ser Trp Ile Phe Ala Ser Lys Tyr His Leu Glu Thr Ile Arg Cys

ATG AAA GGC TAC GAA CCG ACT AAA ATC TCC GCC CTC TAT GTG GCC AAC TGT TAT
   Met Lys Gly Tyr Glu Pro Thr Lys Ile Ser Ala Leu Tyr Val Ala Asn Cys Tyr

AAA GGC GAA CAT AAA GAT CGA TGT GAT GAA GGT TCT AGT CCC ATG GAA TTT CTG
   Lys Gly Glu His Lys Asp Arg Cys Asp Glu Gly Ser Ser Pro Met Glu Phe Leu

CAA ATT ATC GAA GAT TAT GGC TTT CTG CCG GCG GAA TCT AAC TAT CCG TAT AAC
   Gln Ile Ile Glu Asp Tyr Gly Phe Leu Pro Ala Glu Ser Asn Tyr Pro Tyr Asn

TAT GTA AAA GTT GGC GAA CAG TGT CCG AAG GTT GAA GAT CAC TGG ATG AAC CTT
   Tyr Val Lys Val Gly Glu Gln Cys Pro Lys Val Glu Asp His Trp Met Asn Leu

TGG GAT AAC GGC AAG ATC TTG CAT AAC AAA AAC GAA CCG AAT AGC CTG GAT GGT
   Trp Asp Asn Gly Lys Ile Leu His Asn Lys Asn Glu Pro Asn Ser Leu Asp Gly

AAG GGC TAT ACC GCG TAC GAA AGC GAG CGT TTT CAC GAT AAC ATG GAC GCG TTT
   Lys Gly Tyr Thr Ala Tyr Glu Ser Glu Arg Phe His Asp Asn Met Asp Ala Phe

GTT AAA ATT ATT AAA ACC GAA GTG ATG AAC AAA GGT TCT GTG ATC GCG TAT ATC
   Val Lys Ile Ile Lys Thr Glu Val Met Asn Lys Gly Ser Val Ile Ala Tyr Ile

AAA GCG GAA AAC GTG ATG GGT TAC GAA TTC AGC GGC AAG AAA GTG CAA AAC CTG
   Lys Ala Glu Asn Val Met Gly Tyr Glu Phe Ser Gly Lys Lys Val Gln Asn Leu

TGC GGC GAT GAT ACG GCT GAT CAT GCA GTT AAC ATT GTG GGT TAC GGC AAC TAT
   Cys Gly Asp Asp Thr Ala Asp His Ala Val Asn Ile Val Gly Tyr Gly Asn Tyr

GTA AAC TCA GAA GGT GAA AAA AAG TCA TAC TGG ATC GTG CGT AAC TCT TGG GGC
   Val Asn Ser Glu Gly Glu Lys Lys Ser Tyr Trp Ile Val Arg Asn Ser Trp Gly

CCG TAC TGG GGC GAT GAA GGT TAT TTT AAA GTC GAC ATG TAC GGC CCG ACC CAC
   Pro Tyr Trp Gly Asp Glu Gly Tyr Phe Lys Val Asp Met Tyr Gly Pro Thr His

TGC CAT ATC GAA TTC TAG 3'
   Cys His Ile Glu Phe ***
```

Fig. 12

```
                     M  E  Q  V  C  D  V  F  D  I  Y  A  I  C  A  C
tctagaaataatttgttaacttttaagaaggagatatacatATGGAGCAGGTATGTGACGTTTTCGACATCTACGCGATTTGCGCGTGC    48
                                          Nde I C  V  E  S  K  N  E  G  K  K  N  E  V  F  N  N  Y  T  F  F  R  G  L  G  N  K  G  V  L  P
TGCAAGGTGGAGTCAAAGAACGAGGGAAAAAAAATGAGGTGTTCAACAACTACACATTTCGAGGCCTTGGCAACAAGGTGTGTTGCCG  138
                                                                  Stu I W  K  C  N  S  L  D  M  K  Y  F  C  A  V  T  T  Y  V  N  E  S  K  Y  E  K  L  K  Y  K  R
TGGAAATGCAACTCATTGGATATGAAGTACTTTTGTGCAGTGACCACGTATGTGAATGAAAGTAAATACGAAAAACTTAAGTATAAGCGG  228
                       Sca I C  K  Y  L  N  K  E  T  V  D  N  V  N  D  M  P  N  S  K  K  L  Q  N  V  V  V  M  G  R  T
TGTAAGTATCTCAACAAAGAAACAGTTGACAACGTCAATGATATGCCTAACTCTAAAAAACTGCAGAACGTCGTTGTAATGGGCCGCACG  318
                                                             Pst I                 (T)

(T')
 S  W  E  S  I  P  K  K  F  K  P  L  S  N  R  I  N  V  I  L  S  R  T  L  K  K  E  D  F  D
AGCTGGGAATCAATCCCGAAAAAATTCAAGCCGTTGTCGAATCGCATCAATGTGATCCTCTCTAGAACGTTGAAGAAAGAGGACTTTGAC  408
(C)

E  D  V  Y  I  I  N  K  V  E  D  L  I  V  L  L  G  K  L  N  Y  Y  K  C  F  I  I  G  G  S
GAAGATGTATATATTATTAATAAGGTGGAAGATTAATCGTCGTCCTCCTAGGTAAGTTGAATTACTACAAATGCTTTATTATTGGCGGCAGC  498
        (T)                                     Avr II

V  V  Y  Q  E  F  L  E  K  K  L  I  K  K  I  Y  F  T  R  I  N  S  T  Y  E  C  D  V  F  F
GTTGTTTATCAGGAATTTTTGGAGAAGAAGCTGATCAAGAAGATCTACTTTACGCGTATCAATAGCCACCTATGAATGTGACGTGTTCTTC  588

P  E  I  N  E  N  E  Y  Q  I  I  S  V  S  D  V  Y  T  S  N  N  T  T  L  D  F  I  I  Y  K
CCCGGAAATTAATGAGAACGAGTACCAGATAATCTCCGTCAGCGACGTCTACACCTCTAACAACACTACTTTGGACTTTATTATTTATAAG  678

K  *
AAGTAAGAtccggctgctaacaaagccgaaggaagctgagttggctgctgccaccgctgagcaataactagcataaccccttggggcc    768

Fig. 17
```

DNA and deduced amino-acid sequence of SE47

```
ATG AAA TCT TAT ATT TCT CTG TTT TTC ATC CTG TGT GTA ATA TTC AAC
Met Lys Ser Tyr Ile Ser Leu Phe Phe Ile Leu Cys Val Ile Phe Asn

AAA AAC GTG ATC AAA TGT ACC GGT GAA AGC CAG ACC GGT AAT ACC GGC
Lys Asn Val Ile Lys Cys Thr Gly Glu Ser Gln Thr Gly Asn Thr Gly

GGT GGT CAG GCA GGC AAC ACG GTT GGC GAC CAG GCG GGC TCT ACC GGC
Gly Gly Gln Ala Gly Asn Thr Val Gly Asp Gln Ala Gly Ser Thr Gly

GGC TCT CCG CAG GGT AGC ACA GGC GCC AGT CAA CCC GGC TCT AGC GAA
Gly Ser Pro Gln Gly Ser Thr Gly Ala Ser Gln Pro Gly Ser Ser Glu

CCG TCT AAC CCA GTG TCT TCT GGC CAT TCT GTT AGT ACC GTT AGC GTT
Pro Ser Asn Pro Val Ser Ser Gly His Ser Val Ser Thr Val Ser Val

AGC CAG ACC AGC ACC TCT TCT GAA AAA CAA GAT ACC ATT CAG GTG AAA
Ser Gln Thr Ser Thr Ser Ser Glu Lys Gln Asp Thr Ile Gln Val Lys

TCT GCG CTG CTG AAA GAT TAT ATG GGT TTA AAA GTT ACG GGC CCG TGT
Ser Ala Leu Leu Lys Asp Tyr Met Gly Leu Lys Val Thr Gly Pro Cys

AAC GAA AAT TTC ATC ATG TTC CTG GTT CCG CAT ATT TAT ATT GAT GTG
Asn Glu Asn Phe Ile Met Phe Leu Val Pro His Ile Tyr Ile Asp Val

GAT ACC GAA GAT ACC AAT ATA GAG CTC CGT ACC ACC CTG AAA GAA ACC
Asp Thr Glu Asp Thr Asn Ile Glu Leu Arg Thr Thr Leu Lys Glu Thr

AAC AAC CGC ATC TCA TTT GAA TCA AAC AGT GGT TCA CTG GAA AAA AAA
Asn Asn Arg Ile Ser Phe Glu Ser Asn Ser Gly Ser Leu Glu Lys Lys

AAA TAT GTG AAG CTT CCG TCA AAC GGC ACC ACC GGT GAA CAG GGT TCA
Lys Tyr Val Lys Leu Pro Ser Asn Gly Thr Thr Gly Glu Gln Gly Ser

AGT ACA GGC ACC GTT CGC GGC GAT ACC GAA CCG ATT TCA CAC TCG AGT
Ser Thr Gly Thr Val Arg Gly Asp Thr Glu Pro Ile Ser His Ser Ser

AGC TCT TCG TCC AGT TCA AGC TCC TCT AGC TCG TCA TCT AGC TCG TCT
Ser Ser Ser Ser Ser Ser Ser Ser Ser Ser Ser Ser Ser Ser Ser Ser

AGC AGT TCA TCC AGC AGT TCT AGC TCG TCC TCT AGT TCC AGC TCA TCG
Ser Ser Ser Ser Ser Ser Ser Ser Ser Ser Ser Ser Ser Ser Ser Ser

AGC GAA AGT CTT CCG GCG AAT GGC CCG GAT TCC CCG ACC GTT AAA CCC
Ser Glu Ser Leu Pro Ala Asn Gly Pro Asp Ser Pro Thr Val Lys Pro

CCG CGT AAC CTG CAG AAC ATA TGT GAA ACC GGC AAA AAC TTC AAA CTG
Pro Arg Asn Leu Gln Asn Ile Cys Glu Thr Gly Lys Asn Phe Lys Leu

GTG GTG TAT ATT AAG GAG AAT ACA TTA ATC ATT AAA TGG AAA GTG TAC
Val Val Tyr Ile Lys Glu Asn Thr Leu Ile Ile Lys Trp Lys Val Tyr

GGC GAA ACC AAA GAT ACC ACC GAA AAT AAC AAA GTG GAC GTA CGC AAG
Gly Glu Thr Lys Asp Thr Thr Glu Asn Asn Lys Val Asp Val Arg Lys

TAT CTG ATT AAC GAA AAG GAA ACC CCG TTT ACT AGT ATT CTA ATC CAT
Tyr Leu Ile Asn Glu Lys Glu Thr Pro Phe Thr Ser Ile Leu Ile His
```

Fig. 21

```
GCA TAT AAA GAA CAT AAT GGC ACC AAC CTG ATC GAA ACT AAA AAC TAC
Ala Tyr Lys Glu His Asn Gly Thr Asn Leu Ile Glu Thr Lys Asn Tyr

GCG CTG GGC TCA GAC ATT CCG GAA AAA TGT GAT ACC CTG GCG TCC AAT
Ala Leu Gly Ser Asp Ile Pro Glu Lys Cys Asp Thr Leu Ala Ser Asn

TGC TTT CTG AGT GGT AAC TTT AAC ATT GAA AAA TGC TTT CAG TGC GCG
Cys Phe Leu Ser Gly Asn Phe Asn Ile Glu Lys Cys Phe Gln Cys Ala

CTG CTG GTG GAA AAA GAA AAT AAA AAC GAC GTG TGT TAC AAA TAC CTA
Leu Leu Val Glu Lys Glu Asn Lys Asn Asp Val Cys Tyr Lys Tyr Leu

AGC GAA GAT ATT GTG TCT AAT TTC AAG GAG ATC AAA GCG GAG TAA
Ser Glu Asp Ile Val Ser Asn Phe Lys Glu Ile Lys Ala Glu ***
```

Fig. 21 continued

GENE ENCODING PROTEIN ANTIGENS OF *PLASMODIUM FALCIPARUM* AND USES THEREFOR

RELATED APPLICATIONS

This application is a continuation-in-part of U.S. application Ser. No. 07/870,806, filed Apr. 17, 1992 (abandoned) which is a continuation of U.S. application Ser. No. 07/231,771, filed Aug. 12, 1988 (abandoned). The contents of these applications are incorporated herein by reference.

FUNDING

Work described herein was supported in part by funding from the National Institutes of Health grant No. AI22038 and under a grant entitled "Study of antigenic variation in malaria for malaria vaccine" from the International Scientific Research Program of the Ministry of Education and Culture of Japan.

BACKGROUND

Malaria is a significant global health problem. It is widespread, and constitutes a growing health problem of major proportions, particularly in developing countries.

Malaria is caused by several species of the genus *Plasmodium*, the most virulent species being *Plasmodium falciparum* (*P. falciparum*). Parasites growing in erythrocytes are responsible for the pathological manifestations of the disease in man. During the blood stage of infection, *P. falciparum* parasites infect the cells and develop within the erythrocytes through three successive, morphologically distinct stages known as ring, trophozoites and schizonts. A mature schizont eventually produces multiple infectious particles, known as merozoites, which are released upon rupture of the red blood cells. The merozoites invade new red blood cells after a short extracellular life in the blood.

The increased resistance of the malaria parasite to drugs, as well as the resistance of the mosquito vector to insecticide, has increased the need for a malaria vaccine. H. S. Banyal and J. Inselburg, *Am. J. Trop. Med. Hyg.*, 34(6): 1055–1064 (1985). One approach to the development of a vaccine has been to use monoclonal antibodies to identify and characterize specific malarial antigens involved in antibody-sensitive processes that are essential to the maintenance of the parasite growth cycle. These antibodies are known as "parasite inhibitory" antibodies. These parasite inhibitory antibodies can be induced by a host's immune response to the complementary antigens. Such an antigen, or combination of antigens, could therefore provide the basis for an effective malarial vaccine. Some parasite inhibitory antibodies have been isolated and the *P. falciparum* parasite antigens they recognize have been identified by H. S. Banyal and J. Inselburg, in *Am. J. Trop. Med. Hyg.*, 34(6):1055–1064 (1985). See also, P. Deplace, et al., *Molecular and Biochemical Parasitology*, 23: 193–201 (1987); J. L. Weber, et al., *Molecular Strategies of Parasitic Invasion*, Agubian, Goodman and Nogueira (Eds.), Alan R. Liss, Inc., New York, N.Y. pp. 379–388 (1987); P. Deplace, et al., *Molecular and Biochemical Parasitology*, 17: 339–251 (1985); J. D. Chulay, et al., *The Journal of Immunology*, 139: 2768–2774 (1987); and A. Bhatia, et al., *Am. J. Trop. Med.*, 36(1): 15–19(1987).

The key to developing an antimalarial vaccine based on a defined antigen is to isolate and characterize the gene encoding the antigen recognized by a parasite inhibitory antibody so it may be manipulated by gene cloning techniques to provide sufficient amounts of appropriate antigen for vaccine production.

Available approaches to diagnosing, preventing and treating malaria are limited in their effectiveness and must be improved if a solution is to be found for the important public health problem malaria represents worldwide.

SUMMARY OF THE INVENTION

The invention pertains to an isolated nucleic acid sequence which encodes the SERA protein antigen of the malaria parasite *Plasmodium falciparum* (*P. falciparum*), which antigen is capable of eliciting parasite inhibitory antibodies in a parasite host. The term "SERA" is derived from serine repeat antigen based on the presence of a serine repeat sequence in the amino acid sequence of the protein.

In particular, the invention comprises the *P. falciparum* cDNA having the nucleotide sequence shown in FIG. 2 (SEQ ID NO: 1), the amino acid sequence derived from it shown in FIG. 3 (SEQ ID NO: 2), and the genomic DNA sequence shown in FIG. 6 (SEQ ID NO: 3). The isolated genomic DNA sequence of the invention can include the SERA gene regulatory sequences contained in the 5' flanking sequence of the gene, and the signal sequences, also shown in FIG. 3 and FIG. 6 (SEQ ID NO: 2 and 3, respectively). The regulatory sequence can be used to direct expression of the SERA gene, or they may be used independent of the SERA DNA sequences, to direct the expression of other DNA sequences, especially other malarial DNA sequences. The signal sequences can be used to direct exportation of the SERA protein, or independent of the SERA DNA, to direct exportation of a protein by a cell.

The invention also pertains to the immunogenic protein antigen, SERA, or immunogenic equivalents thereof, encoded by the isolated DNA of the invention. The amino acid sequence of the protein antigen is shown in FIG. 3 and FIG. 6 (SEQ ID NO: 2 and 3, respectively). The protein can be produced by recombinant DNA techniques. For example, cDNA of the invention can be incorporated into an expression vector and the vector used to infect a host cell for expression of the SERA antigen.

The invention further pertains to a method of producing a malarial protein, in *E. coli* cells, which elicits a malarial inhibitory antibody. This method includes: transforming an *E. coli* cell with an expression vector containing DNA encoding a malarial protein which protein is reactive with antibody inhibitory of *Plasmodium falciparum* wherein the DNA encoding a malarial protein comprises the *E. coli* codons comparable to *P. falciparum* codons based on usage preference for the amino acids of the malarial protein; then culturing the cell to produce the protein as the major *E. coli* protein that is synthesized; and then recovering the protein from the cell in a pure form to facilitate the commercial preparation of the protein. The method can be used, for example, with the nucleotide sequences shown in FIGS. 11, 12 and/or 21 (SEQ ID NO: 14, 16 and 18, respectively). The invention also pertains to the nucleotide sequences shown in FIGS. 11, 12 and 21 (SEQ ID NO: 14, 16 and 18, respectively) and the amino acid sequences for which they code (SEQ ID NO: 15, 17, and 19, respectively). The polypeptides are designated as SE47 (FIG. 21, SEQ ID NO: 19), SE47' (FIG. 11, SEQ ID NO: 15) and SE50A (FIG. 12, SEQ ID NO: 17). Further, isolated polypeptides produced in *E. coli* are included in the invention.

This invention includes a malaria vaccine which is composed of the SERA antigen or a portion thereof, in a pharmaceutically acceptable carrier, and a method of vaccinating against malaria with this vaccine. Also included in the invention are malaria vaccines which include a malarial protein produced in *E. coli* cells in combination with a pharmaceutically acceptable carrier. In addition, vaccines which include DNA which encode all or a portion of the SERA protein in a pharmaceutically acceptable carrier are included in the invention.

BRIEF DESCRIPTION OF THE FIGURES AND TABLES

FIG. 1 shows a schematic representation of the restriction map, cDNA and genomic clones for the SERA gene. (a) Restriction sites shown are B. BglII; E. EcoRI; H. HindIII; K. KpnI; P. PstI; X. XbaI. (b) Enlarged restriction map encompassing the SERA gene. (c) Locations of certain cDNA molecules. (d) Location of the genomic DNA clone MBN#3102. (e) Location of the long open reading frame coding for the SERA protein.

FIG. 2 shows the cDNA sequence encoding the SERA protein (SEQ ID NO: 1). The sequence begins in the nontranslated leader sequence for the SERA gene mRNA.

FIG. 3 shows the amino acid sequence of the SERA protein (SEQ ID NO: 2). The 989 amino acids encoded by the SERA gene are shown using the one letter code. The signal sequence and the three possible N-linked glycosylation sites of the SERA gene are underlined.

FIG. 4 shows the results of a Northern blot analysis of the SERA gene mRNA. The locations of RNA size markers of 5.1 and 2.1 Kb are shown.

FIG. 5 shows the a schematic representation of the restriction map of the SERA gene, cDNA clones and genomic DNA clones. (a) Restriction sites shown are $B_1$ BglII; E, EcoRI; H, HindIII; K, KpnI; P, PstI; X, XbaI. (b) Enlarged restriction map encompassing the SERA gene. (c) Location of the cDNA clones used as probes in this study. (d) Location of the genomic clones E31 and E3C. (e) Location of the genomic DNA clone MBN#3102. (f) Location of the SERA genomic DNA including the exons, introns and flanking sequences. Three introns are clear (☐) boxes and the exons are filled (■) boxes.

FIG. 6 shows the genomic DNA sequence of the SERA gene (SEQ ID NO: 3) and the amino acid sequence (SEQ ID NO: 4) which it encodes. Nucleotide sequences corresponding to the broken line of the amino acid sequence indicates the location of the three SERA gene introns. The stop codon is marked ***. Several restriction sites arc boxed: three HinfI sites, GANTC, and one EcoRI site, GAATTC. The 5' nucleotide of the clone MBN#3102 is underlined (T, nucleotide 3795). The regulatory sequence is encoded by base pairs 485–2526.

FIG. 7 shows portions of the SERA allele I (SEQ ID NO: 5) and allele II (SEQ ID NO: 4) repeat sequences, AG(T or C) TC(A or T), encoding the polyserine repeats. The nucleotide numbers in the right margin correspond to those in FIG. 6. The upper 39 bp sequence found in allele I at the position shown, is absent from allele II. Eight single nucleotide differences between allele I and allele II were underlined in allele II. A ninth nucleotide change in the coding region is not shown (nucleotide 3993 in Table I). The two boxed sequences shown were chosen to make the oligonucleotide probes (probe A in cDNA to identify allele I and probe B in clone E31 genomic DNA to identify allele II). A HinfI restriction site in the 39 bp sequence is also boxed.

FIG. 8 shows the results of Southern hybridization of HinfI-treated clone E3C, clone E31, FCR3 genomic DNA, and Honduras I genomic DNA with the 210 bp HinfI fragment of allele II (clone E31). Lanes a–c respectively contained 0.9 μg, 1.8 μg and 3.6 μg of FCR3 genomic DNA. Lanes d–f respectively contained 0.225 ng, 0.45 ng and 0.90 ng of clone E3C. Lanes g–i contained clone E31 in the same amounts as lanes d–f. Lanes j–l contained Honduras −1 genomic DNA in the same amounts as lanes a–c. The filter was hybridized with the $^{32}$P-labeled 210 bp HinfI fragment of clone E31. The upper band in lanes a–c and g–i is a 210 bp fragment. The lower broader bands in lanes a–f and j–l contain two fragments (132 bp and 117 bp), which are not well resolved in agarose gels.

FIG. 9 shows the results of Southern hybridization of EcoRI digested clone E3C, clone E31 and FCR3 genomic DNA. The filter was probed with $^{32}$P-labeled probe A. Lanes a–c respectively contained 1.8 ug, 3.6 ug and 7.2 ug of FCR3 genomic DNA. Lanes d–f respectively contained 0.45 ng, 0.90 ng and 1.8 ng of pUC19 plasmid containing clone E3C. Lanes g–i respectively contained 0.45 ng, 0.90 ng and 1.8 ng of pUC19 plasmid containing clone E31.

FIG. 11 shows the DNA sequence (SEQ ID NO: 14) and deduced amino acid sequence (SEQ ID NO: 15) of SE47'. The DNA has been constructed using the preferred *E. coli* codons as discussed in the Examples.

FIG. 12 shows the DNA sequence (SEQ ID NO: 16) and deduced amino acid sequence (SEQ ID NO: 17) of SE50A. The DNA has been constructed using the preferred *E. coli* codons as discussed in the Examples.

Figure 13:
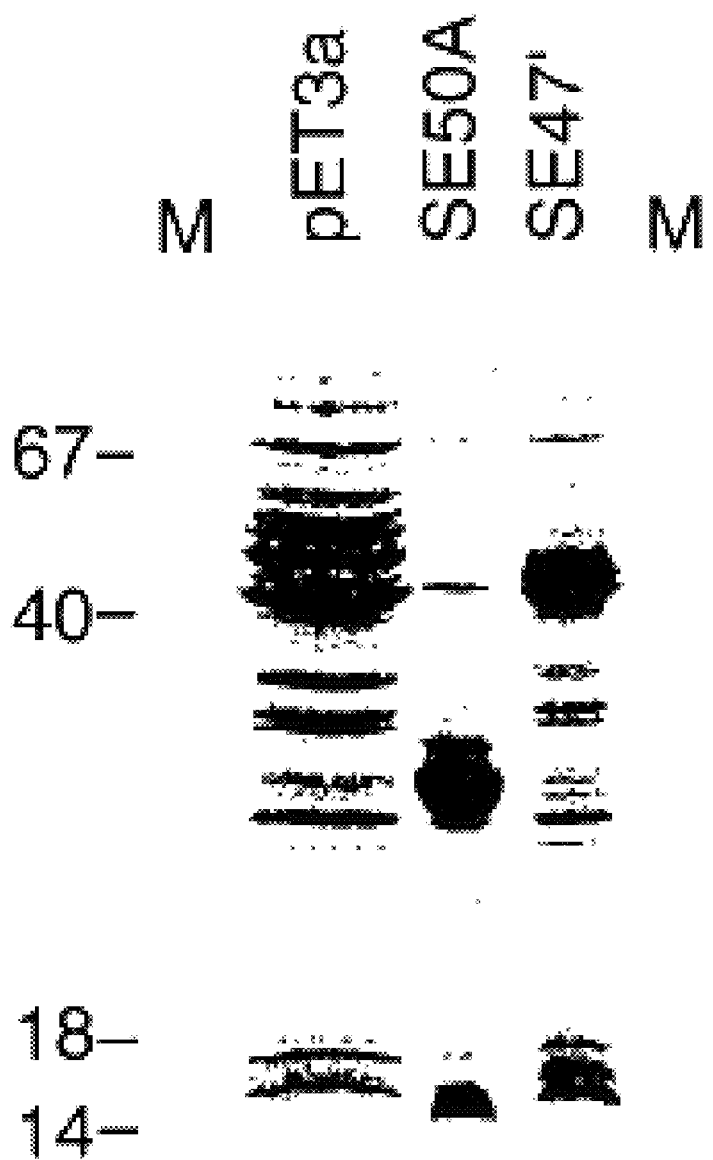

FIG. 13 shows SDS-polyacrylamide gel electrophoresis of the recombinant SERA proteins induced in *E. coli* cells. The lanes contained: M, molecular weight standards; pET3a, cell containing vector DNA; SE50A, cell containing pET3a-SE50A plasmid; SE47', cell containing pET3a-SE47' plasmid.

Figure 14:
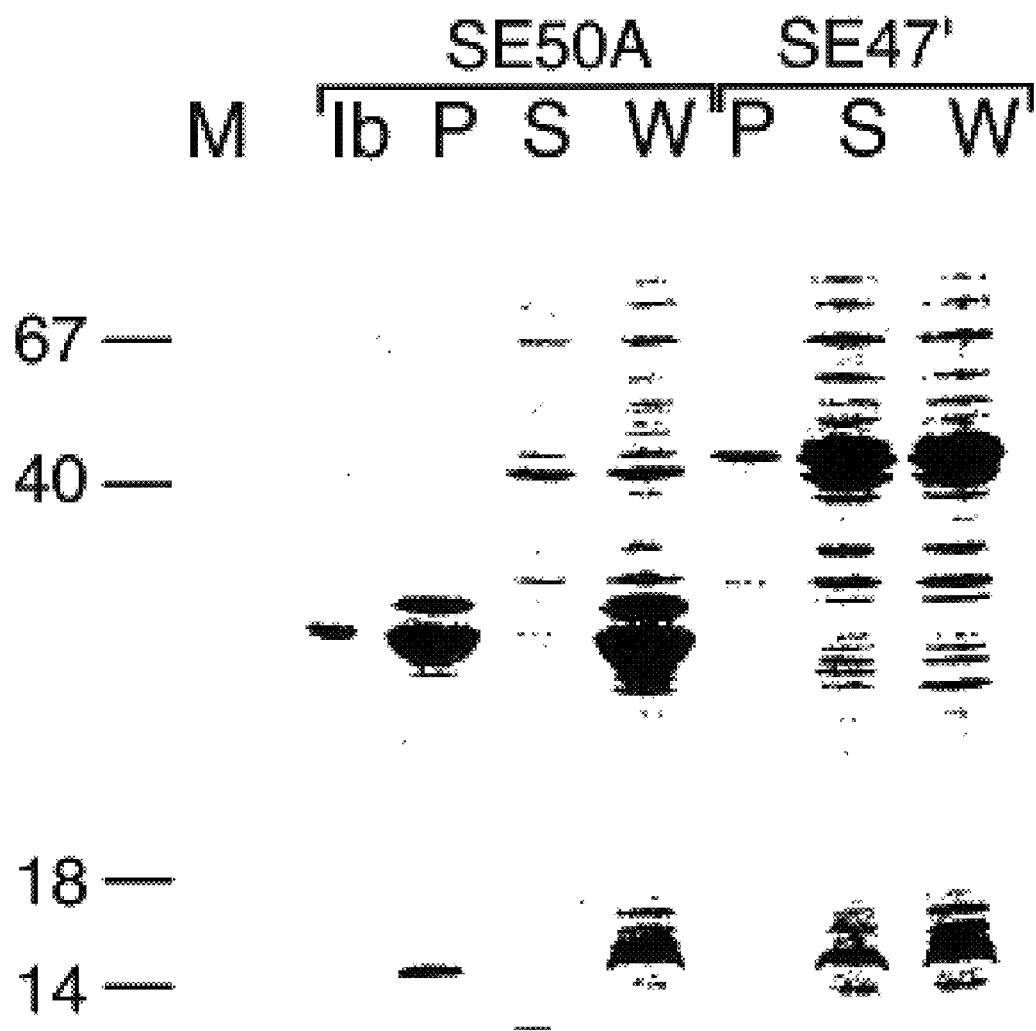

FIG. 14 shows the cellular location in *E. coli* of the recombinant SE47' and SE50A proteins after the protein's induction in *E. coli* cells. The lanes contained M, molecular weight standards; W, whole cell; S, soluble fraction after cell lysis; P, insoluble fraction after cell lysis, and Ib, purified inclusion body from the precipitate of lysed cells producing SE50A. The precipitate was solubilized with a buffer containing 10% SDS and 0.1M 2-mercaptoethanol. After removal of insoluble materials, the protein was precipitated by removing the SDS and 2-mercaptoethanol again. The final precipitate was run on the gel. The newly synthesized recombinant proteins, in large amounts, are of the expected sizes.

Figure 15:
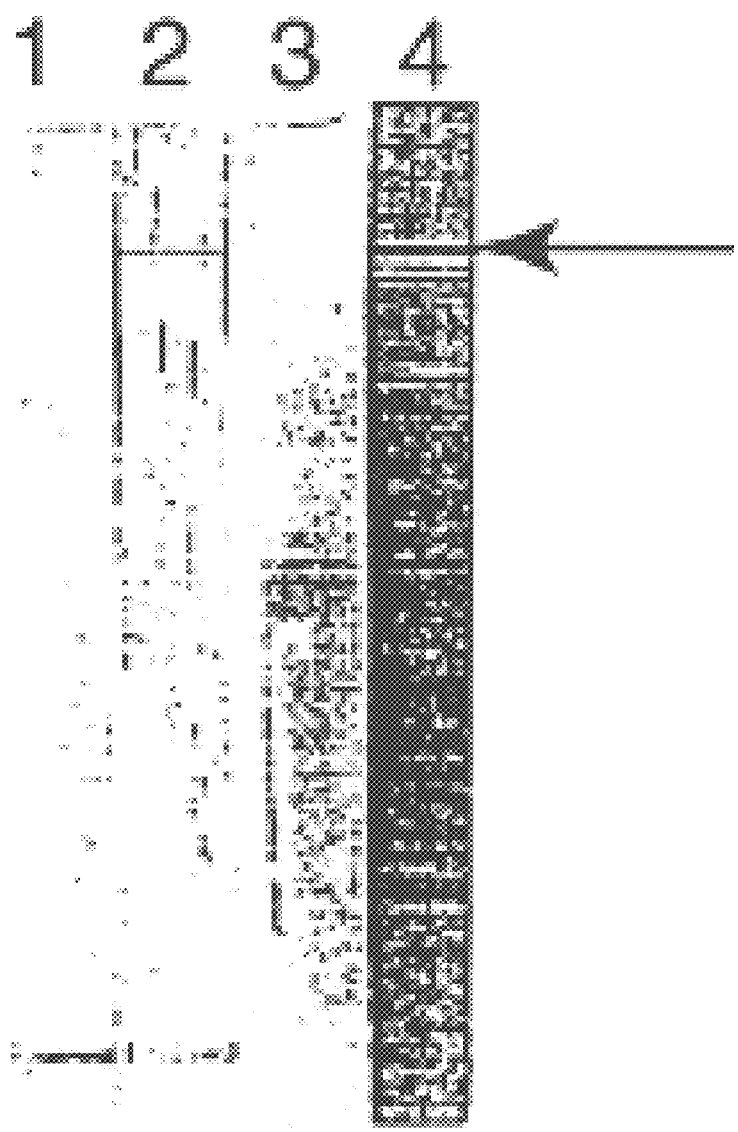

FIG. 15 shows an immunoblot of whole cellular proteins of *Plasmodium falciparum* FCR3 strain with anti-serum against SE47' or SE50A. The antisera used for the immunoblot were as follows: lane 1, control mouse serum; lane 2, mouse anti-SF47' serum; lane 3, control rat serum; lane 4, rat anti-SE50A serum. The arrow indicates the molecular weight corresponding to SERA protein. Thus, anti-SE47' and SE50A antibodies recognize the complete SERA protein.

Figure 10:
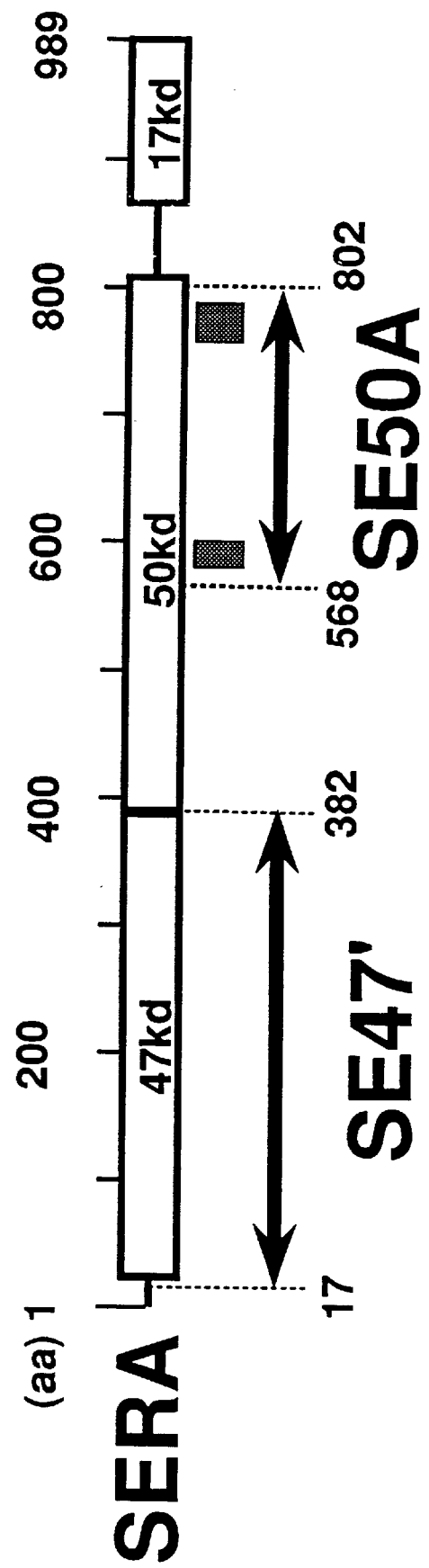
FIG. 10 shows the location in the whole SERA gene of the synthetic SERA gene sequences, SE47'(SEQ ID NO: 14) and SE50A (SEQ ID NO: 16), that were synthesized with *E. coli* codon preferences.
Figure 16A:
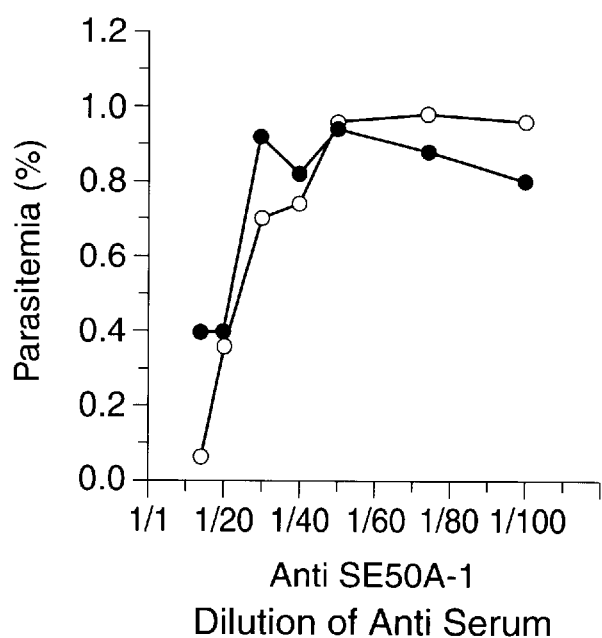
Figure 16B:
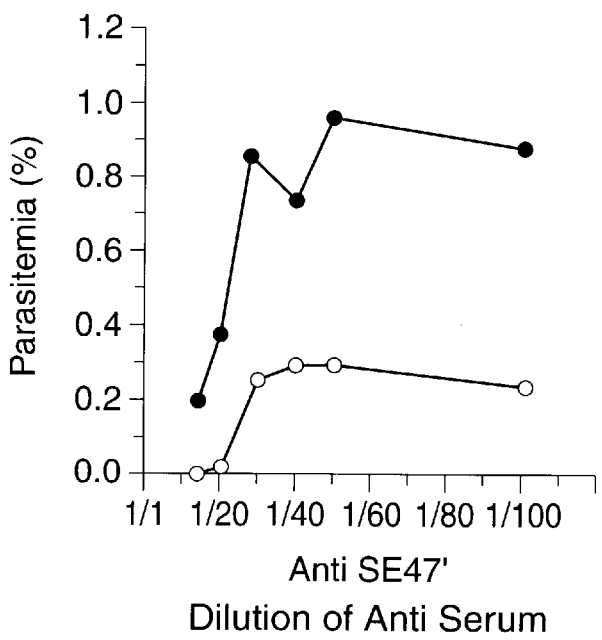

FIGS. 16A and 16B show *Plasmodium falciparum* growth inhibition with anti-SER47' and anti-SE50A serum. FIG. 16A shows the growth inhibition of *Plasmodium falciparum* using varying dilutions of anti-SE50A1 serum from rat #1 (Table VI) and FIG. 16B shows the growth inhibition of *Plasmodium falciparum* using varying dilutions of anti-SE47' serum from mouse #3 (Table VI). The inhibition confirms that the new constructs of SERA (FIG. 10, FIG. 11, and FIG. 12) produce immunogenic material and that adjuvant enhances the induction of parasite inhibitory levels of antibodies.

FIG. 17 shows the DNA sequence of the synthetic gene encoding the DHFR of P. falciparum DHFR-TS complex (SEQ ID NO: 11). The 684 nucleotide coding region encoding the DHFR protein was divided into five units by utilizing the restriction sites as shown. Each unit was composed of 2 to 5 synthetic oligonucleotides which were annealed to form each unit. Since the DNA synthesizer occasionally introduced erroneous nucleotides, each unit with the designated sequence was screened by sequencing before connecting the units. The amino acid sequence (SEQ ID NO: 12) encoded by the constructed DHFR is shown by the one letter code. The nucleotide sequence with the capital letters is the constructed gene and the proximal nucleotide sequences with small letters are from a plasmid pET-3a(Studier, F. W., et. al. (1 990) *Methods Enzymol.*, 185:60–89). The sequence in the parentheses is for DHFR$^{Thr108}$ in which the serine at position 108 in the drug-sensitive P. falciparum strain 3D7 (Peterson et al. (1 988) *PNAS USA* 85:9114–9118; Cowman et al. (1988) *PNAS USA* 85:9109–9113; and Zolg et al. (1989) *Mol. Biochem. Parasitol.* 36:253–262) is changed to threonine. Four additional nucleotide changes that were DNA synthesizer errors are in the third letters of each of the codons resulting in no amino acid alterations.

Figure 18:
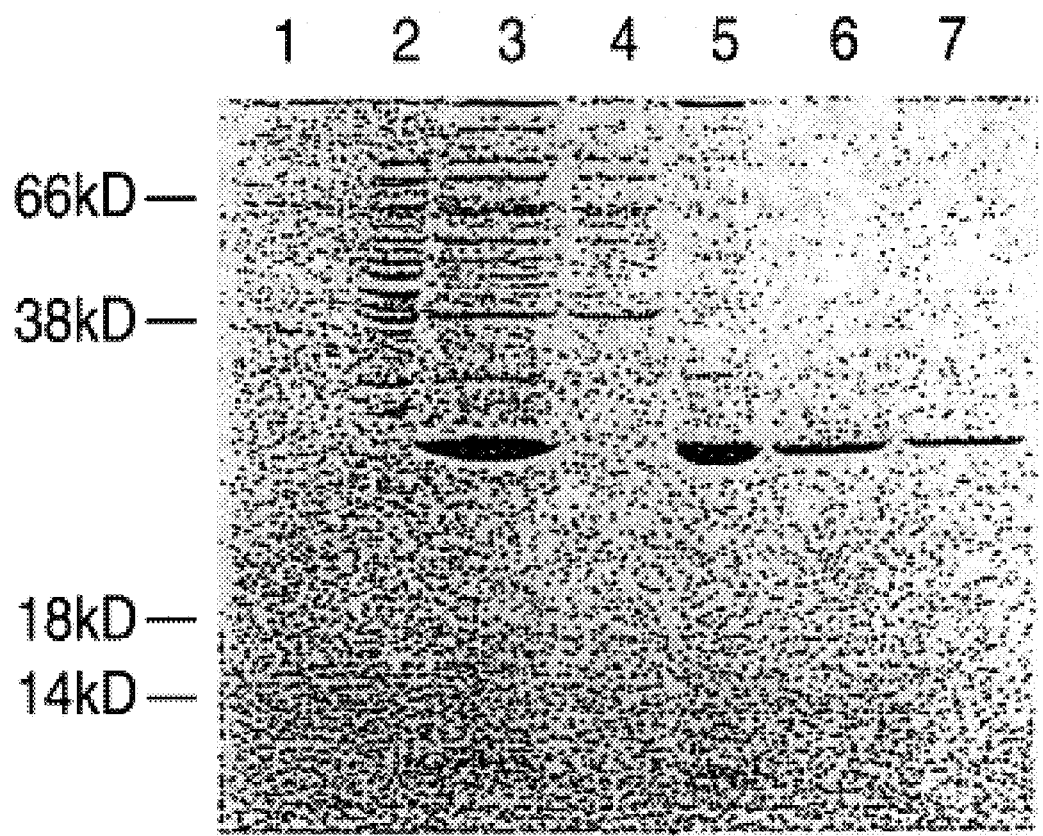

FIG. 18 shows SDS-polyacrylamide gel electrophoresis of DHFR following each step of the protein purification from E. coli cells containing pET-PfDHFR$^{Thr108}$. A sample from each purification step was electrophoresed in a 12.5% SDS-polyacrylamide gel and stained with Coomassie Brilliant Blue R-250. Lane 1, the molecular weight standards, bovine serum albumin, 66 kd, RecA protein of E. coli, 38 kd, β-lactoglobulin, 18 kd, lysozyme, 14 kd; lane 2, total E. coli JM103 cell protein containing pET-3a induced by M13-pKM2 and IPTG; lane 3, total E. coli JM103 protein containing pET-PfDHFR$^{Thr108}$ induced by M13-pKM2 and IPTG. Lanes 4–7 are each step of the DHFR purification as described below; lane 4, supernatant fraction of cell lysate; lane 5, precipitate fraction of cell lysate; lane 6, fraction after hydroxylapatite column; lane 7, fraction after S-300 column.

Figure 19A:
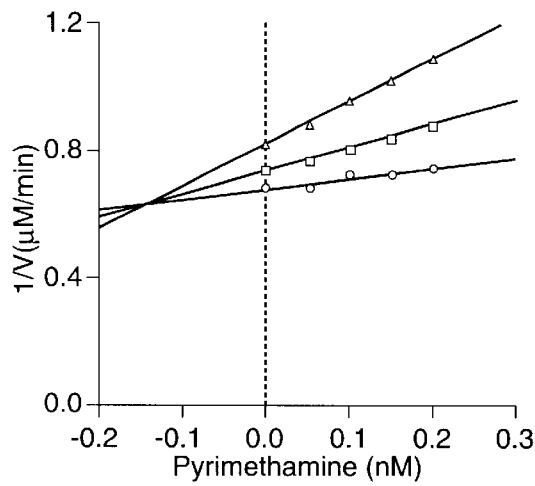
Figure 19D:
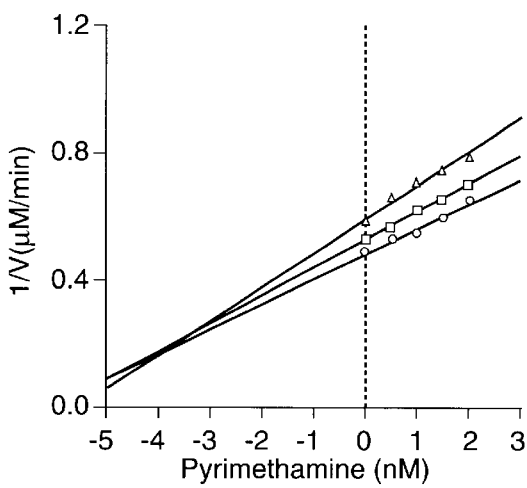
Figure 19B:
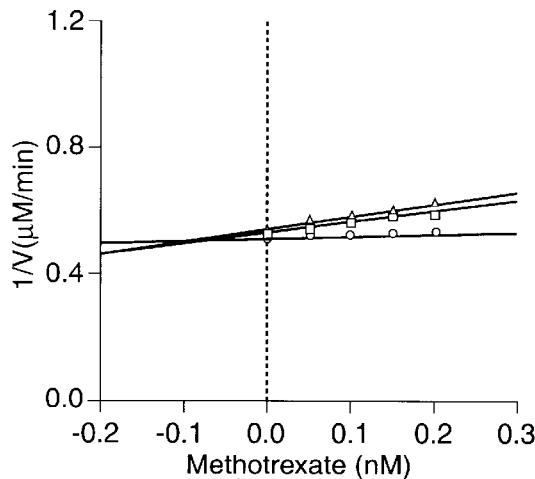
Figure 19E:
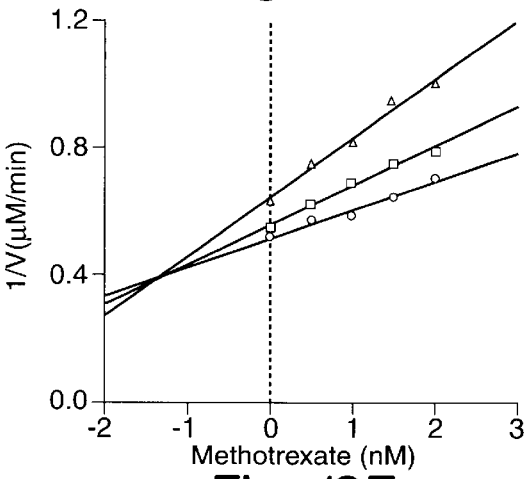
Figure 19C:
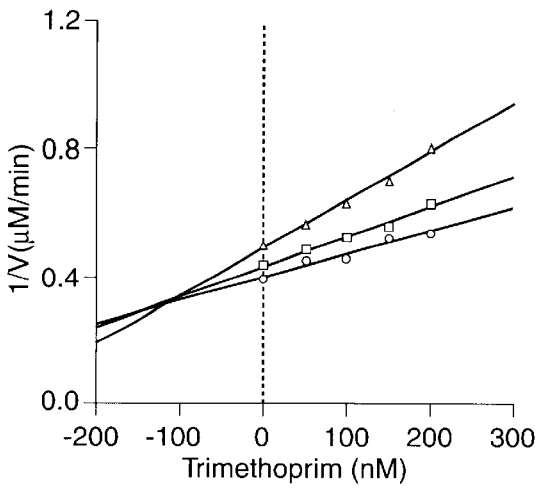
Figure 19F:
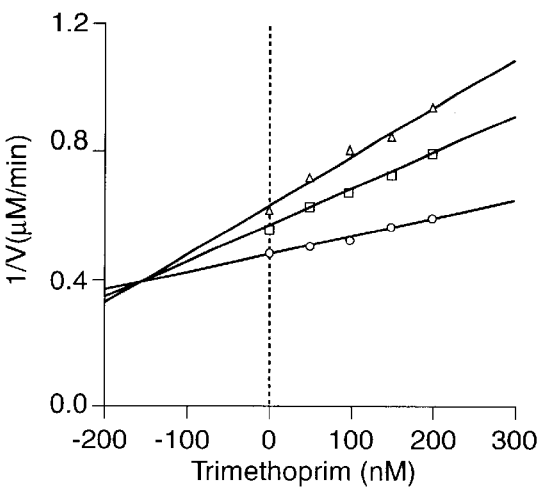

FIGS. 19A–19F show Dixon plots of the inhibition of DHFR$^{Thr108}$ and DHFR$^{Ser108}$ with pyrimethamine, methotrexate, and trimethoprim. The reaction was carried out as described below except that the reaction was started by adding the indicated amount of DHF after the preincubation with the indicated amount of the inhibitor for two minutes at 37° C. Each point represents the mean of triplicate samples with a variation of less than 5%. FIGS. 19A–19C are DHFR$^{Thr108}$; FIGS. 19D–19F are DHFR$^{Ser108}$.

Figure 20A:
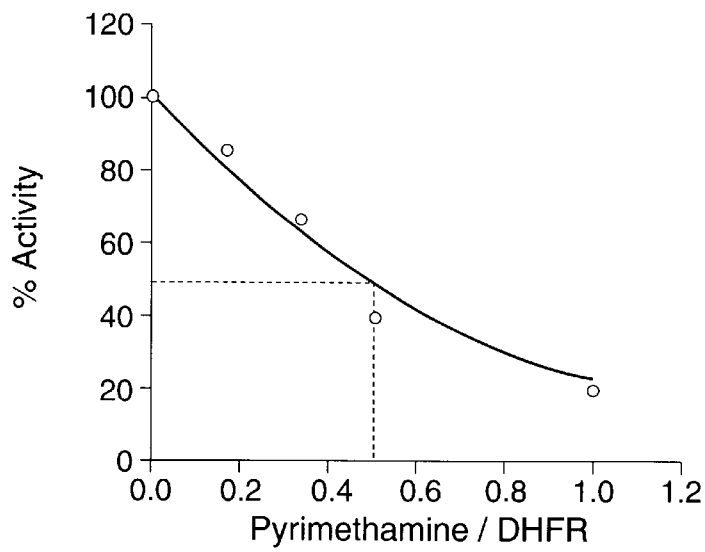
Figure 20B:
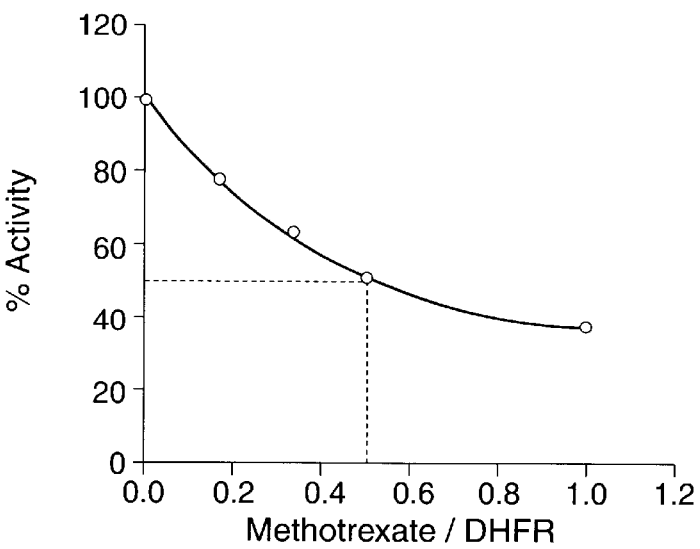
Figure 20C:
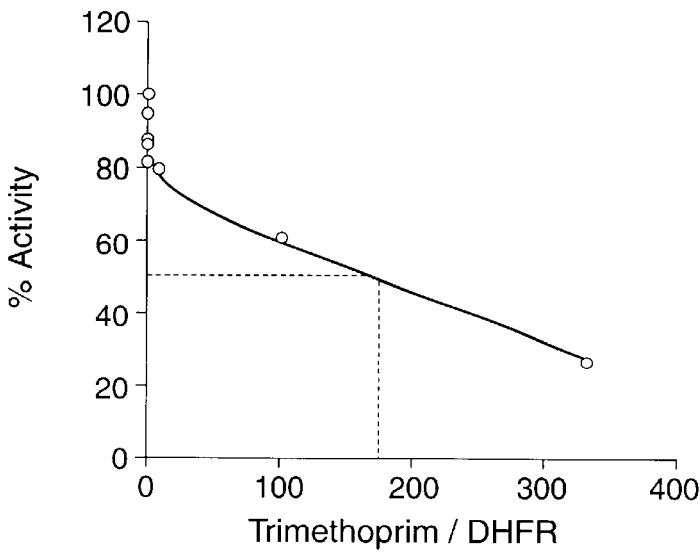

FIGS. 20A–20C show the titration of DHFR with pyrimethamine (FIG. 20A), methotrexate (FIG. 20B), and trimethoprim (FIG. 20C). Each reaction contained 3 nM of purified DHFR$^{Thr108}$ and DHFR$^{Ser108}$. Enzyme activity was measured spectrophotometrically as described below after preincubation of the reaction mixture with inhibitor for two minutes at 37° C. The amount of inhibitor included in the reaction is described as a molar ratio with the DHFR. Each point represents the mean of two samples.

FIG. 21 shows the DNA sequence (SEQ ID NO: 18) and the deduced amino acid sequence (SEQ ID NO: 19) of SE47. The DNA has been constructed using the preferred E. coli codons as discussed in the Examples.

DETAILED DESCRIPTION OF THE INVENTION

Figure 6:
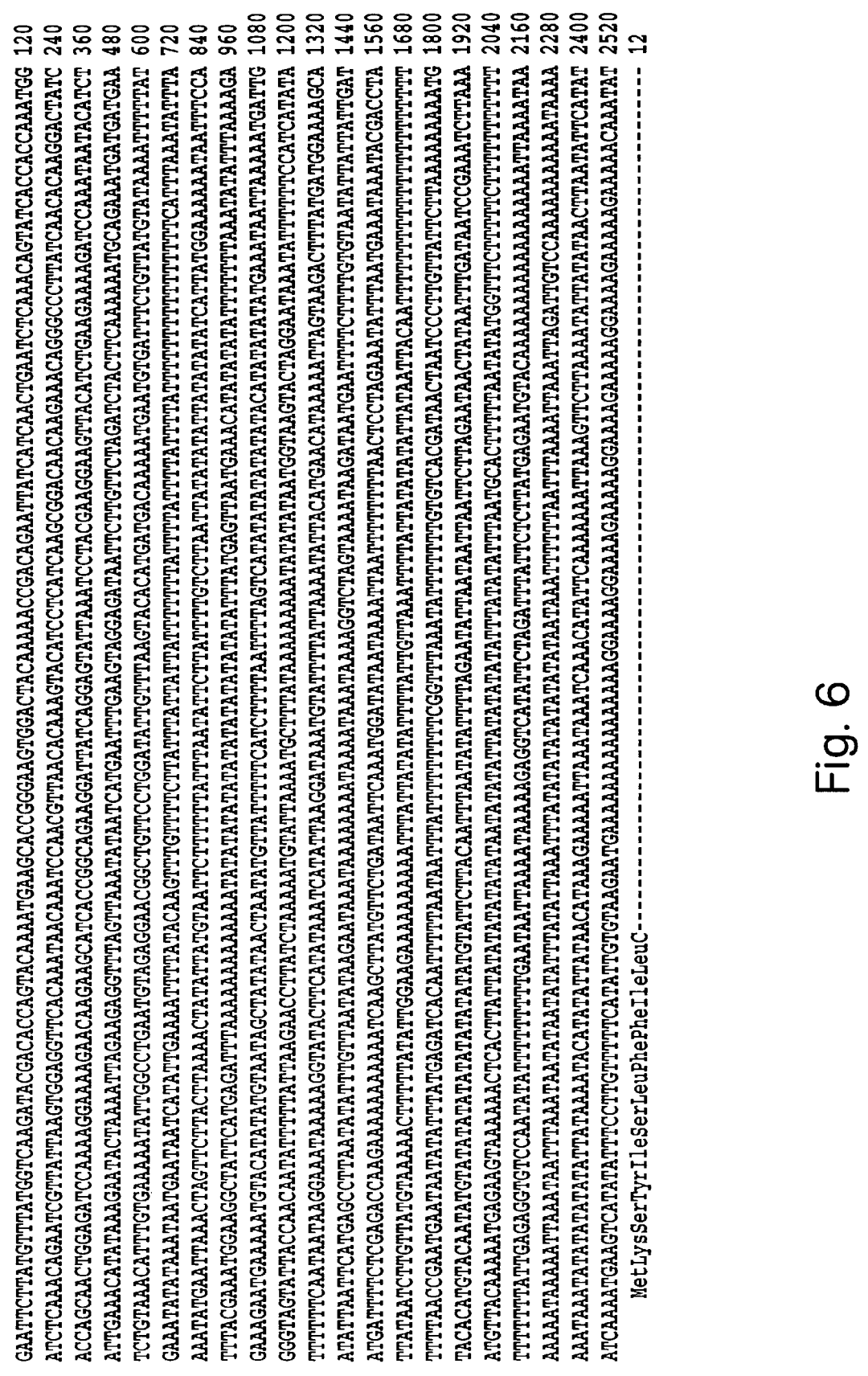
Figure 6:
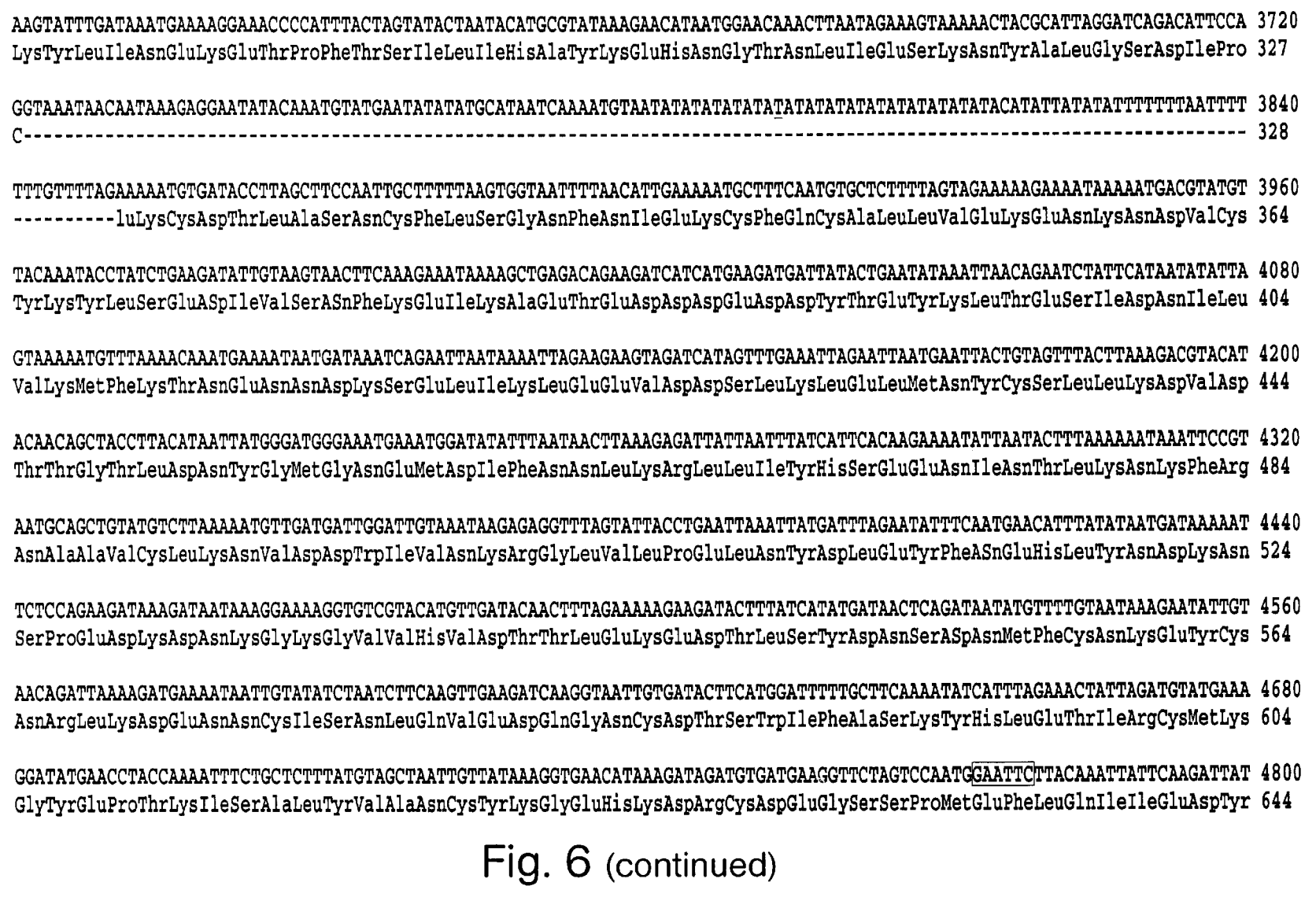

The SERA gene encodes the SERA antigen, which is an immunogenic protein antigen of the parasite P. falciparum, the most virulent species of malaria. FIG. 2 shows the nucleotide sequence encoding the SERA antigen (SEQ ID NO: 1). FIG. 3 shows the amino acid sequence (SEQ ID NO: 2) derived from that cDNA sequence, and FIG. 6 shows the genomic DNA, introns, and flanking sequences that contain the transcriptional regulatory sites as well as the encoded amino acid sequence (SEQ ID NO: 4). The nucleotide sequence of the invention includes DNA sequences substantially complementary to the nucleotide sequence shown in FIGS. 2 and 6 (SEQ ID NO: 1 and 3, respectively), or portions thereof, including additions, deletions and variations of the nucleotide sequence which encode one or more antigenic determinants of the SERA antigen.

Figure 1:
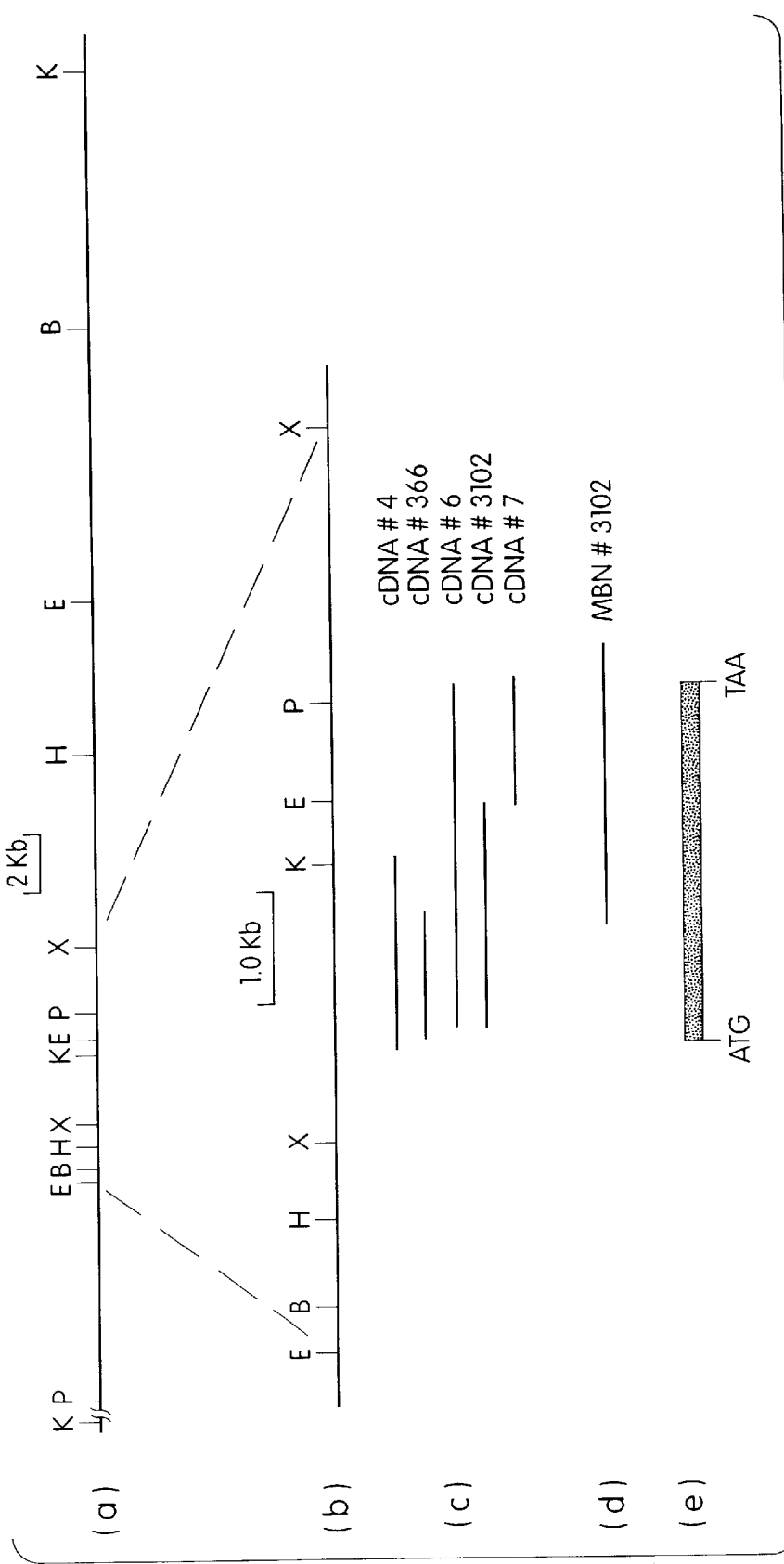

The SERA gene was isolated from the P. falciparum genome using recombinant DNA techniques. Briefly, RNA was obtained from red blood cells containing parasites in the trophozoite and schizont stages. A lambda gtll expression library was constructed from the RNA, and the expression library was screened immunologically with pooled human immune serum to form a gene bank of positive clones. The gene bank expressed antigens recognized by human antimalarial polyclonal serum. The positive-clone gene bank was then screened with a parasite-inhibitory, mouse monoclonal antibody, 43E5, to identify clones producing antigens recognized by both it and the parasite-inhibitory human antibodies. A cDNA clone in the gene bank, designated clone #366, was isolated. Clone #366 strongly reacted with both the human immune sera and the murine monoclonal antibody, indicating that it encoded an immunogenic protein antigen present in the blood stage of the parasite. The cDNA clone was then sequenced to obtain part of the complete nucleotide sequence shown in FIG. 2 (SEQ ID NO: 1). The complete cDNA sequence in FIG. 2 was finally established using clone #366 as a probe of cDNA libraries and other probes developed from clones in such libraries. A representation of the clones derived starting with clone #366, from which the complete cDNA sequence was determined, is shown in FIG. 1.

Figure 5:
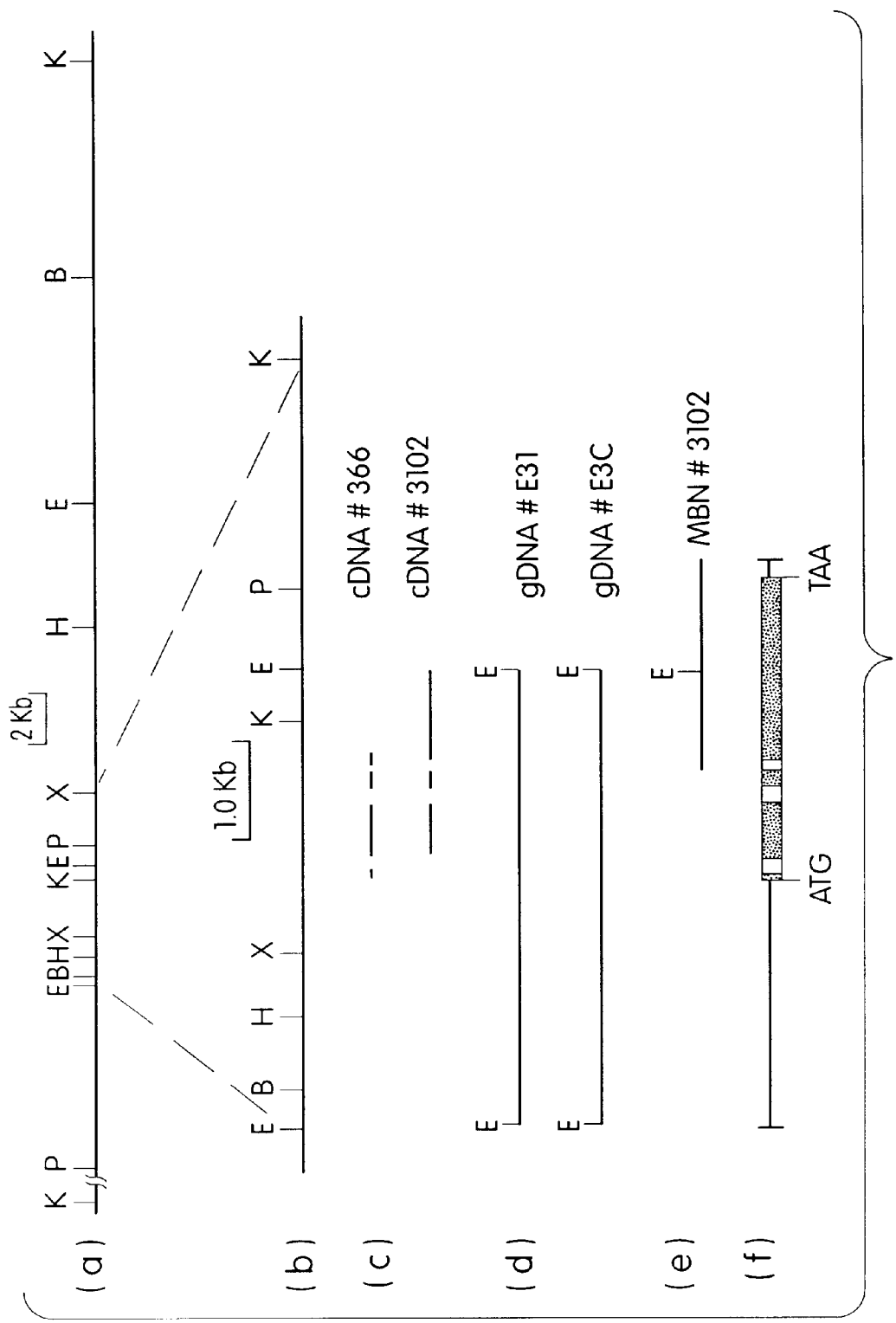

The complete genomic DNA sequence was established using two genomic DNA clones gDNA #E3C and MBN#3102 (see FIG. 5). The genomic sequence with introns is shown in FIG. 6.

The gross protein structure appears to be conserved in ten geographically separate P. falciparum isolates (Bhatia et al., *Am. J. Trop. Med. Hyg.*, 36:15–19 (1987)). The independent demonstration of its parasite-inhibitory immunogenicity, its abundance in late developmental stages, its accessibility to the host immune system, and its apparent conservation in geographically isolated strains all suggest the antigen is an excellent candidate antigen for a vaccine. Also, SERA is processed in P. falciparum as three fragments at the time of parasite release at the end of schizogony. The fragments are 47, 50 and 18 kd fragments. The synthesized nucleotide sequences that encode SE47, SE47' and SE50A protein represent sequences encoding parts of the 47 and 50 kd portions of processed protein. The knowledge of the complete SERA sequence and genomic structure, which is essential for the engineering of its production, makes its use as a vaccine practical.

In another embodiment, a nucleic acid of the invention encodes a peptide comprising all or a portion of the amino acid sequence encoded by the nucleotide sequences of FIGS. 2 or 6 (SEQ ID NO: 1 and 3, respectively). Preferred nucleic acids encode a peptide having at least about 50% homology, more preferably at least about 60% homology and most preferably at least about 70% homology with all or a portion of the amino acid sequence encoded by the nucleotide sequences of FIGS. 2 or 6 (SEQ ID NO: 1 and 3, respectively). Nucleic acids which encode peptides having a Der p III activity and having at least about 90%, more preferably at least about 95%, and most preferably at least about 98–99% homology with all or a portion of the amino acid sequence encoded by the nucleotide sequences of FIGS. 2 or 6 (SEQ ID NO: 1 and 3, respectively) are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Further embodiments of the invention include isolated nucleic acids wherein the peptide is at least 50% homologous with a sequence comprising the amino acid sequence MKSYISLFFILCVIFN (SEQ ID NO: 7), a sequence comprising an amino acid sequence shown in FIG. 21 (SEQ ID NO:19), a sequence comprising an amino acid sequence shown in FIG. 11 (SEQ ID NO:15), or a sequence comprising an amino acid sequence shown in FIG. 12 (SEQ ID NO:17).

A vaccine based on the SERA protein, or an immunogenic portion of the protein, can be made by incorporating the protein into a pharmaceutically acceptable carrier. For example, the SERA antigen or portions thereof, including SE47 (SEQ ID NO: 19), SE47' (SEQ ID NO: 15) and SE50A (SEQ ID NO: 17), containing one or more antigenic determinants of the SERA antigen can be prepared in injectable form for parenteral administration by incorporating them in a vehicle with or without an adjuvant. In addition, isolated SERA protein, or an immunogenic portion thereof, can be provided in the vaccine substantially free of other malarial proteins.

Also, a vaccine based on the SERA DNA, or an immunogenic portion thereof, can be made by incorporating the DNA into a pharmaceutically acceptable carrier. For example, DNA encoding SE47 (SEQ ID NO:18) can be prepared in injectable form for parenteral administration by incorporating it into a vehicle with or without an adjuvant.

The protein antigens encoded by part of or the entire SERA gene of P. falciparum may be used in serodiagnostic tests for malaria. Such antigens would be highly specific to P. falciparum, and the tests in which they are used would also be highly specific. Highly specific serological tests would be of great value in screening populations for individuals producing antibodies to P. falciparum; in monitoring the development of active disease in individuals; and in assessing the efficacy of treatment. As a result of using such a diagnostic tool, early diagnosis of malaria will be feasible, thus making it possible to institute treatment at an early stage in the disease and, in turn, reduce the likelihood it will be transmitted.

The cDNA nucleotide sequence of the SERA gene, (shown in FIG. 2) (SEQ ID NO: 1), the amino acid sequence (SEQ ID NO:2) and the genomic sequence (SEQ ID NO: 3) of the SERA gene (both shown in FIG. 6), have been identified. Recombinant DNA techniques can be used to produce the SERA protein. In these techniques, generally, the DNA encoding all or a desired part of the protein would be incorporated into a DNA expression vector, such as a plasmid. The resulting recombinant vector can then be introduced into a host cell. Generally the host cell is prokaryote, such as E. coli, but eukaryotic host cells can be employed. The transformed cells can be screened for the production of the gene product. This can be accomplished by linking the DNA of interest to a marker gene in the vector, such as LacZ, or by direct assay, such as by using antibodies to detect the presence of the antigen. The cells which are found to express the antigen at high levels can then be cultivated to produce desired quantities of the protein.

The region of the genomic DNA containing gene regulatory sequences associated with the SERA gene (shown in FIG. 6, bp 485–2526) cause the SERA gene product to be produced at very high levels in the parasite. Based on a Northern blot analysis of trophozoite and schizont mRNA and an analysis of the P. falciparum cDNA library with SERA gene probes, as much as 2% of trophozoite and schizont mRNA is devoted to this antigen's production (see FIG. 4). The regulatory sequence of the SERA DNA can be used to stimulate high-efficiency expression of other genes in addition to the SERA gene. For example, the regulatory sequence can be isolated using the appropriate restriction endonucleases, or it can be synthesized. The regulatory sequence can then be incorporated into a vector, such as a plasmid, to direct the expression of a gene of choice.

The SERA signal sequence (shown in FIG. 3, in one letter code for amino acids, as the amino acid sequence MKSYISLFFILCVIFN (SEQ ID NO: 7)) can be used to cause the SERA protein, or other proteins to which it becomes linked, to be exported. The SERA signal sequences can be linked to a protein-encoding DNA sequence to produce secretable protein. The signal sequence directs the passage of the protein through the cell membrane. Such signal or "pre" sequences are characteristic of secreted proteins and consist mainly of hydrophobic amino acid residues which determine the export of the protein across the cell membrane. The SERA signal sequence can be incorporated into a vector with the gene of choice with an appropriate flanking promoter sequence. Normally the signal sequence is placed upstream of and adjacent to the gene. The vector is then used to transform a host cell. The recombinant host cell will secrete the protein encoded by the gene of choice as directed by the SERA signal sequence.

Another embodiment of the invention is a method of producing a malarial protein in E. coli cells which includes transforming an E. coli cell with an expression vector containing DNA encoding a malarial protein which protein is reactive with antibody inhibitory of Plasmodium falciparum wherein the DNA encoding a malarial protein comprises the preferred E. coli codons for the amino acids of the malarial protein, then culturing the cell to produce the protein and recovering the protein from the cell. As examples, the dihydrofolate reductase (DHFR) protein and portions of the SERA protein have been expressed using this method (see Examples 2 and 3). The malarial protein produced using this method can elicit a malarial inhibitory antibody. Further, the malarial protein that is produced is substantially free of other malarial proteins. The portions of the SERA protein include SE47 (SEQ ID NO: 19), SE47' (SEQ ID NO: 15) and SE50A (SEQ ID NO: 17) and are substantially free of other malarial proteins.

Expression of a recombinant malarial protein in E. coli involves first resynthesizing the genetic information after selecting a codon preference that takes into account both the P. falciparum codon preference and the E. coli codon preference. If a similar protein exists in E. coli, then the E. coli preference can be taken directly. If no similar protein exists in E. coli, the following codon selection strategy can be used. A table of codon frequencies for "all" P. falciparum proteins is established as is a table of codon frequencies for "all" *E. coli* proteins (Table V). For example, if an amino acid in SERA is encoded by a codon that is the second most frequently used codon for that amino acid then the corresponding *E. coli* codon for that amino acid is selected for the gene. This strategy has been chosen to provide comparable translation velocities that can influence protein folding and protein activity of the product produced in *E. coli*. Codons that are either more or less favored by *E. coli* than those in *P. falciparum* can also be used for resynthesizing the genetic information from *P. falciparum*.

A further embodiment of the invention is an isolated nucleic acid encoding the amino acid sequence of a malarial protein wherein each codon is the preferred codon in *E. coli* for encoding an amino acid of the malarial protein. For example, the preferred codon can be a codon which is used as frequently or more frequently than the codon which codes for the amino acid in the original *P. falciparum* gene.

Another embodiment of the invention is an isolated polypeptide expressed in, for example, *E. coli*. For example, the polypeptide can be a portion of the SERA protein produced recombinantly in *E. coli* such as SE47' or SE50A. The protein can be in a soluble form or found in inclusion bodies. The term isolated as used herein refers to a nucleic acid or peptide that is substantially free of cellular material or culture medium when produced by recombinant DNA techniques, or chemical precursors or other chemicals when chemically synthesized. Such peptides are also characterized as being free of all other malarial proteins. Accordingly, an isolated peptide is produced recombinantly or synthetically and is substantially free of cellular material and culture medium or substantially free of chemical precursors or other chemicals and is free of all other malarial proteins. An isolated nucleic acid is also free of sequences which naturally flank the nucleic acid (i.e., sequences located at the 5' and 3' ends of the nucleic acid) in the organism from which the nucleic acid is derived.

A further embodiment of the invention are isolated polypeptides encoded by the nucleotide sequence shown in FIG. 21 (SEQ ID NO:18), the nucleotide sequence shown in FIG. 11 (SEQ ID NO:14), or the nucleotide sequence shown in FIG. 12 (SEQ ID NO: 16). The nucleotide sequences reflect the *E. coli* codon bias for expression in *E. coli*. In addition, isolated, immunogenic portions of the SERA protein expressed in *E. coli* encompass another embodiment of the invention.

The invention is further illustrated by the following exemplification.

EXEMPLIFICATION

Example 1

Materials and Methods
Parasites and Culture Conditions

*P. falciparum* strains FCR3 and Honduras I were grown in vitro as described by W. Trager and Jensen in *Science*, 193:673–675 (1976) and by J. Inselburg, *J. Parasitol.*, 69:584–591 (1983). RPMI 1640 medium was supplemented with 25 mM HEPES buffer (pH 7.2), 0.2% sodium bicarbonate, 10% heat inactivated human plasma (type A, Rh+), penicillin (100 IU ml$^{-1}$), streptomycin (100 μg ml$^{-1}$), and gentamycin (20 μg ml$^{-1}$).

Synchronization of parasites was done by the sorbital method (C. Lambros and S. P. Vandenburg, *J. Parasitol.*, 65:418–420 (1976)), and a population of trophozoite and schizont containing red blood cells (RBC) was prepared by Plasmagel fractionation of a culture (R. T. Reese, et al., (1979) B711.WHO57 (suppl.), 53–61).

Preparation of Parasite RNA and DNA

Red blood cells (RBCs) containing parasites in the trophozoite and schizont stages were washed once with RPMI 1640 medium, resuspended in a solution that contained 0.015% saponin, incubated for 0.3 hours at 37° C., and were then collected and washed twice by centrifugation with phosphate buffered saline (PBS, 0.01 M KH$_2$PO$_4$/NaHPO$_4$, 0.14 M NaCl, pH 7.4).

Total parasite RNA was isolated using the guanidium isothiocynate method. The poly(A) RNA was purified through an oligo d(T)-cellulose column as described previously (T. Maniatis, et al., *Molecular Cloning: A Laboratory Manual*, Cold Spring Harbor Laboratory, Cold Spring Harbor, N.Y. (1982)).

Chromosomal DNA was co-purified with the RNA from the GuITC homogenate. After ultracentrifugation of the GuITC homogenate, the DNA on the CsCl shelf was collected and purified by conventional CsCl banding (T. Maniatis, et al., ibid.).

Construction of a cDNA Expression Library

The method of cDNA synthesis using reverse transcriptase and the Klenow fragment of *Eschericia coli* DNA polymerase I was followed (T. Maniatis, et al., ibid.). Ten micrograms of poly(A) RNA was used in each reaction. After the synthesis of the second strand, the cDNA hairpin structure was cut with S1 nuclease (Bethesda Research Labs), and the reaction was treated with a phenol/chloroform mixture. The purified double stranded cDNA was repaired by successive treatment with the Klenow fragment of DNA polymerase I and T4 DNA polymerase (New England Biolabs). The DNA was methylated with EcoRI methylase and the cDNA was ligated with an octamer EcoRI linker (GGAATTCC). After digestion with EcoRI, the DNA was fractionated by size using agarose gel electrophoresis to avoid possible bias in the size distribution of the cDNA library. The cDNAs with the length of 0.2–0.5 kb, 0.5–2 kb, 2–5 kb and 5–10 kb were separately collected by electrophoresis onto DEAE 81 paper (G. Dretzen, et al., *Anal. Biochem.*, 112:295–298 (1981)). The lambda gt11 phage (R. A. Young and R. W. Davis, *Proc. Natl. Acad. Sci. USA*, 80:1194–1198 (1983)), was the vector used for construction of the cDNA expression library (T. Maniatis et al., ibid.).

Mung Bean Nuclease Genomic DNA Libraries

Mung bean nuclease (MBN) digestion of FCR3 parasite DNA was done as described by D. J. Bzik et al. in *Proc. Natl. Acad. Sci. USA*, 84:8360–8364 (1987). DNA fragment sizes of 0.75 to 3.0 kb and 3.0 to 10 kb were collected from a 1.0% agarose gel and purified. The libraries were constructed in the lambda phage vector lambda gt11, as for the cDNA library above.

Construction and Screening of Genomic DNA Libraries

Genomic DNA libraries were constructed in lambda gt11 as an EcoRI library (G. Dretzen et al., (1981) *Anal. Biochem.*, 112:295–298) and as an MBN library. Gene fragments in lambda gt11 were subcloned into the plasmid pUC19 and the recombinant plasmids were introduced into *E. coli* strain DH5δ by transformation (D. Hanahan, *J. Mol. Biol.*, 166:557–580 (1983)). Plasmid DNA was prepared exactly as previously described (T. Maniatis et al., ibid.).

Screening of Recombinant Phage by Immunochemical Reactions

Phage producing parasite antigens were screened by an in situ plaque immunoassay (R. A. Young and R. W. Davis, *Proc. Natl Acad. Sci. USA*, 80: 1194–1198 (1983)). About 100,000 packaged phage were screened. The source of antimalarial polyclonal antibody was pooled Nigerian serum provided by Dr. D. Haynes (Walter Reed Army Institute of Research). The Nigerian serum was used at a 1:200 dilution. In total, 288 of the screened Nigerian positive phages were collected, and represented clones from each size fraction of the cDNA library.

Oligonucleotide Synthesis and Labeling

Two single stranded SERA gene specific oligonucleotides, called probe A (a 30-mer: 5' CTG TAT CTC CTC TAA CTG TTC CCG TAC TTG 3') (SEQ ID NO: 8) and probe B (a 31-mer: 5' CTA GAA CTT GAA CTT GAA CTA GAA CTT TGT T 3') (SEQ ID NO: 9) were synthesized at the Dartmouth Molecular Genetics Center, Hanover, N.H. The oligonucleotides were purified on polyacrylamide gels and end-labeled using $T_4$ polynucleotide kinase and ($^{32}$P) ATP (T. Maniatis et al., ibid.).

Subcloning of the cDNA Inserts

DNA from positive phage clones identified in the previous section were purified and subcloned into plasmid pUC19 at its EcoRI site (T. Maniatis et al., ibid.). A pUC19 plasmid cloning vector was linearized by EcoRI digestion and treated with calf intestinal phosphatase. One microgram of a phage clone DNA was cleaved with EcoRI, extracted with phenol/chloroform, ethanol precipitated, and mixed with 0.5 μg of the prepared plasmid DNA in 25 μl of ligation mixture. *E. coli* HB101 or DA52 competent cells (Bethesda Research Labs) were transformed with the ligated DNA by the procedure described by the manufacturer and plated on ampicillin (100 μg m1$^{-1}$) containing LB plates.

In situ and Southern Hybridization

Phage DNA was transferred to nitrocellulose (T. Maniatis et al., ibid.). Restriction enzyme digested *P. falciparum* DNA was transferred to Zeta probe membranes (BioRad, Richmond, Calif.) using the alkaline transfer method as previously described (K. C. Reed and D. A. Mann, *Nucleic Acids Res.*, 13:72077221 (1985) and J. Inselburg et al., *Mol. Biochem. Parasitol.*, 26:121–134 (1987), A. P. Feinberg and B. Vogelstein, *Anal. Biochem.*, 32:6–13 (1983) and *Anal. Biochem.*, 137:266–267 (1984)). Typically, 50 ng of DNA to be used as a probe was oligo-labeled to a specific activity of 1 to 3×10$^9$ cpm,μg$^{-1}$ of DNA. Hybridization conditions were identical for plaque lifts and Southern blots. Hybridizations were usually done overnight at 42° C., in 35% formamide (vol/vol), 6×SSC (T. Maniatis et al., ibid.), 0.5% BLOTTO (D. A. Johnson et al., (1984) *Gene Anal. Tech.*, 1:3–8) and 5 μg poly(A) ml$^{-1}$. The addition of exogenous poly(A) dramatically decreased background hybridization. After hybridization, filters were washed 3 times, for a total of 0.5 h in 1×SSC and 0.1% sodium dodecylsulfate (NaDodSO$_4$) at room temperature. The filters were then washed twice for 1 hour at 60° C., or more, in 1×SSC and 0.1% NaDodSO$_4$ to remove non-specific hybridizing material.

Northern Blot Analysis

Total *P. falciparum* RNA and poly(A)$^+$ RNA were prepared as previously described. Total RNA and poly(A)$^+$ RNA of malaria were size-fractionated by electrophoresis in a 1.2% agarose formaldehyde (6.7%) gel (Lehrach et al., *Biochemistry*, 16:4743–4751 (1977)) and then electrophoretically blotted onto Zetabind membrane (CUNO, Inc. Meriden, Conn.). Hybridization of $^{32}$P-labeled cDNA to RNA-containing filters was done overnight at 42° C. (Wahl, et al., *Proc. Natl. Head. Sci. USA*, 76:3683–3687 (1979)). Hybridization of probe A and probe B oligonucleotides to the RNA-containing filters was done by treating the filters for 2 hr at 37° C. in a solution containing 1 M NaCl, 10×Denhardt's solution, 5% NaDodSO$_4$, 10 mg of poly(A) ml$^{-1}$, and 0.1 mM ATP, followed by hybridization overnight at 37° C. in 1 M NaCl, 10×Denhardt's solution, 1% NaDodSO$_4$, 5% formamide, and 10% Dextran sulfate. The filters were then washed in 1 M NaCl, 10× Denhardt's solution and 1% NaDodSO$_4$ for 30 min at 37° C. Finally, the filters were washed, as required, in more stringent conditions.

DNA Sequencing

DNA sequencing was performed as previously described by D. J. Bzik, et al. in *Proc. Natl Acad. Sci. USA*, 84:8360–8364 (1987), using the dideoxynucleotide technology (F. Sanger et al., *Proc. Natl Acad. Sci. USA*, 74:5463–5467 (1977)). Briefly, DNA fragments were purified (G. Dretzen et al., (1981), *Anal. Biochem.*, 112:295–298), self-ligated, and sonicated (P. L. Deininger, *Biochem.*, 129:216–223 (1983)). 0.3 to 0.7 kb fragments were purified and the DNA ends were enzymatically repaired (blunted) and cloned into SmaI digested, alkaline phosphatase treated M13mp8. Every bp of the sonicated fragments was independently sequenced approximately 6 times (average), and both DNA strands were completely sequenced. DNA sequences were reconstructed using the DNA Inspector II programs (Textco, West Lebanon, N.H.). The BIONET computer resource for molecular biology (IntelliGenetics, Palo Alto, Calif.) was also utilized to manipulate and to compare DNA and amino acid sequences.

RESULTS

Construction of the Blood Stage cDNA Gene Bank

Parasite poly(A) RNA was prepared from parasites in the late trophozoite and schizont stages to construct a lambda gt11 cDNA expression library. This period of the erythrocytic growth cycle is when both protein and RNA synthesis is most active, and when the greatest numbers of different proteins appear to be synthesized (H. Banyal and J. Inselburg, *Am. J. Trop. Med. Hyg.*, 34: 1055–1064 (1985)). The FCR3 cDNA library was screened with a pooled human Nigerian serum that contained antibodies reactive with numerous malaria proteins identified by Western blot analysis. About 100,000 packaged phage were screened and 288 positive clones were picked, purified, and numbered to form the FCR3 gene bank that was used to screen other sources of antimalarial antibodies.

Lambda gt11 is a bacteriophage vector which is capable of driving the expression of foreign DNA which is inserted into its genome with *E. coli* transcription and translation signals. Lambda gt11 expresses the insert DNA as a fusion protein connected to the *E. coli* beta-galactosidase polypeptide. This approach ensures that the foreign DNA sequence will be efficiently transcribed and translated in *E. coli*. This approach is also useful in addressing the problem of the highly unstable nature of most foreign proteins; fusion proteins are often more resistant to proteolytic degradation than the foreign polypeptide alone. The use of lambda gt11 and the *P. falciparum* strains used (FCR3 and Honduras-1) are described by T. Horii, D. J. Bzik and J. Inselburg in *Molecular and Biochemical Parasitology*, 30:9–18 (1988). The teachings of this publication are incorporated herein by reference.

Determining the Structure of the SERA cDNA

Clone cDNA #366 reacted more strongly with mMAb 43E5, so this clone was selected for further study. The cDNA #366 was subcloned into pUC19.

The frequencies of expression of the genes coding for cDNA #366 were estimated by using the oligo-labeled cDNA #366 sequence as a probe of the original cDNA library. Ten thousand phage plaques from the library were assayed by in situ DNA hybridization with each probe. 1.5% of total cDNA phage containing inserts were hybridizable with the cDNA #366.

Isolation of SERA cDNA Clones and a Genomic DNA Clone cDNA#366 DNA was used as a probe to select additional cDNA clones from a cDNA library by DNA hybridization. Five additional cDNA clones that hybridized with radioactively labeled cDNA#366 DNA were isolated, purified, and analyzed. Each of those five cDNA clones contained a single EcoRI fragment insert. The largest clone, cDNA#3102, contained a 1.8 kb EcoRI insert. The cDNA#3102 DNA sequence did not contain a poly(A) sequence. The DNA sequences of cDNA#366 and cDNA#3102 had a 971 bp overlap and together they encoded a 629 amino acid sequence of the SERA gene.

In order to obtain the 3' cDNA sequences, a MBN genomic DNA library was constructed and screened to identify both the 3' cDNA and 5' cDNA containing clones of the SERA gene, because MBN was previously shown to cleave near, but outside of, P. falciparum coding regions. Radioactively labeled cDNA#3102 was used to screen the genomic MBN libraries (0.75 to 3.0 kb; and 3.0 to 10 kb size fractions). 100,000 phage from each library were screened and one clone, MBN#3102, from the 0.75 to 3.0 kb MBN library, hybridized with cDNA#3102. The MBN#3102 clone contained two EcoRI fragments, of 1.0 kb and 1.4 kb. The 1.0 kb EcoRI fragment strongly hybridized with cDNA#3102 sequences. The 1.4 kb EcoRI fragment hybridized very weakly with cDNA#3102 sequences under low but not high stringency washing conditions. Two approaches were used to determine if the 1.4 kb EcoRI fragment of MBN#3102 contained 3' coding sequences of the SERA gene or represented a random double ligation event. The cDNA libraries were screened by hybridization with either the 1.0 or the 1.4 kb EcoRI fragment of MBN#3102. If both of these fragments were adjacent on chromosomal DNA and represented SERA gene sequences, then many cDNA clones should strongly hybridize with both of them. In cDNA libraries constructed from both the 0.5 to 2.0 kb and the 2.0 to 5.0 kb cDNA fragments, many of the cDNA clones strongly hybridized with both the 1.0 kb and 1.4 kb EcoRI fragments. In the second approach, the hybridization pattern of both the 1.0 kb and 1.4 kb EcoRI fragments in Southern blotting experiments were analyzed.

In Southern blotting experiments of parasite genomic DNA it was observed that the 1.0 kb and 1.4 kb EcoRI fragments of MBN#3102 hybridized to the same major bands in BglII, HindIII, and KpnI digests of chromosomal DNA. It was concluded that the two fragments were adjacent on the chromosomal DNA and did not represent a double-ligation event of random EcoRI fragments. A preliminary restriction map for FCR3 and Honduras-1 DNA, which behaves similarly to FCR3 DNA, was constructed from hybridization data (see FIG. 1).

Nucleotide Sequence of the cDNA Clones and the Amino Acid Sequence of the SERA Gene Additional cDNA clones that hybridized with MBN#3102 DNA sequences were identified. Sixteen of those cDNA clones were selected, plaque purified, and their inserts subcloned into pUC19. Their insert sizes were determined by EcoRI digestion and Southern hybridization with the 1.0 kb and 1.4 kb EcoRI fragment of MBN#3102 (the 3' probe) were all approximately 1.0 to 1.1 kb in size. This indicated the distance from the unique EcoRI site in the SERA gene to the 3' end of the mRNA was about 1.0 to 1.1 kb. Several 5' cDNA clones were selected for DNA sequence analysis. The locations of some of those cDNA clones (FIG. 1c) and the MBN#3102 clone (FIG. 1d) are shown. The alignment of the cDNA clones with the genomic restriction map (FIG. 1b) was based on the presence or absence of the unique KpnI, PstI, and EcoRI sites in the cDNA clones, and upon the aligned DNA sequences of the cDNA clones. The DNA sequences for the following cDNA clones: cDNA#4, cDNA#6, cDNA#7, cDNA#366 and cDNA#3102 were determined.

The aggregate cDNA sequence derived from all of those clones is shown in FIG. 2 (SEQ ID NO: 1). The complete DNA sequence for both DNA strands was determined for each cDNA clone. Minor differences from the consensus cDNA sequence were found in some cDNA clones and are summarized in Table 1.

TABLE I

Resolution of Base-pair Differences Between SERA cDNA clones.

| cDNA clone | Location[a] | bp difference | Resolution |
|---|---|---|---|
| cDNA#4 | 1 to 1571 | NONE | |
| cDNA#366[b] | 126 to 1183 | bp 233; G to A | G was present in cDNA#4, cDNA#6, and cDNA#3102 |
| | | bp 1169; G to A | G was present in cDNA#4, cDNA#6, and cDNA#3102 |
| | | bp 1175; G to A | G was present in cDNA#4, cDNA#6, and cDNA#3102 |
| | | bp 1180; T to A | T was present in cDNA#4, cDNA#6, and cDNA#3102 |
| cDNA#6 | 168 to 3058 | bp 1738; deleted | A was present to cDNA#3102 T was present in cDNA#4, |
| | | bp 222; T to G | cDNA#366, and cDNA#3102 |
| | | bp 288; A to G | A was present in cDNA#4, cDNA#366, and cDNA#3102 |
| cDNA#3102 | 212 to 2014 | NONE | |
| cDNA#7 | 2009 to 3107 | NONE | |

[a]- bp location numbers are from FIG. 2.
[b]- cDNA#366 sequence is from reference Horii, T., et al., Molec. and Biochem. Parasitol., 30: 9–18 (1988)

There were 7 base pair (bp) discrepancies between the total 8,427 bp determined for the cDNA clones, and a bp at these locations was assigned (Table 1). Three of the base differences were located at the 3' end of cDNA#366 and were caused during the second strand synthesis in cDNA construction due to the annealing of an oligo-dT molecule at this site (Table 1). cDNA#6 had a 1 bp deletion (bp 1738), probably generated during either cDNA synthesis or the cloning process. The remaining three base changes were clustered at bp 222, 228 and 233 and may represent mRNA polymorphism based on those changes being located in the degenerate octamer repeat of the SERA gene. The presence of the unique EcoRI site (bp 2009 to 2014) in the gene was confirmed by sequencing across that EcoRI site in the phage DNA for both cDNA#6 and MBN#3102.

A long open reading frame began with the ATG at bp 104 and ended at the TAA at bp 3071 (FIG. 1 and FIG. 2). That reading frame, which encoded the SERA gene, contained 989 amino acids with a predicted molecular mass of 111 kDA (FIG. 3). The SERA gene amino acid sequence contained a hydrophobic signal peptide (amino acids 1 to 16 in FIG. 3), but did not contain a membrane anchor domain. The absence of a membrane anchor domain was not unexpected as the antigen was reported to be an exported protein that accumulated in the parasitophorous vacuole (P. Deplace et al., Mol. Biochem. Parasitol., 23:193–201 (1987); P. Delplace et al., Mol. Biochem. Parasitol., 17:239–251 (1985)).

The protein which is highly acidic has an expected net charge of −35. Serine residues account for 11% of the amino acids in the protein and 57% of those serine residues (62 of 108) were localized within a 201 amino acid sequence (residues 26 to 227) that included a 35-mer polyserine repeat. Forty percent of the amino acid residues in that serine rich segment were either serine or threonine (serine=30%; threonine=10%). The coding portion of the SERA gene conformed to the known properties of P. falciparum coding regions in that the coding region had a relatively low A+T content (71%), a high A to T ratio (1.4), an S-value comparable to that of other P. falciparum coding sequences, and an increasing A+T content for the three coding positions (62%, 66%, 86%).

Expression of the SERA Gene in the Parasite

Figure 4:
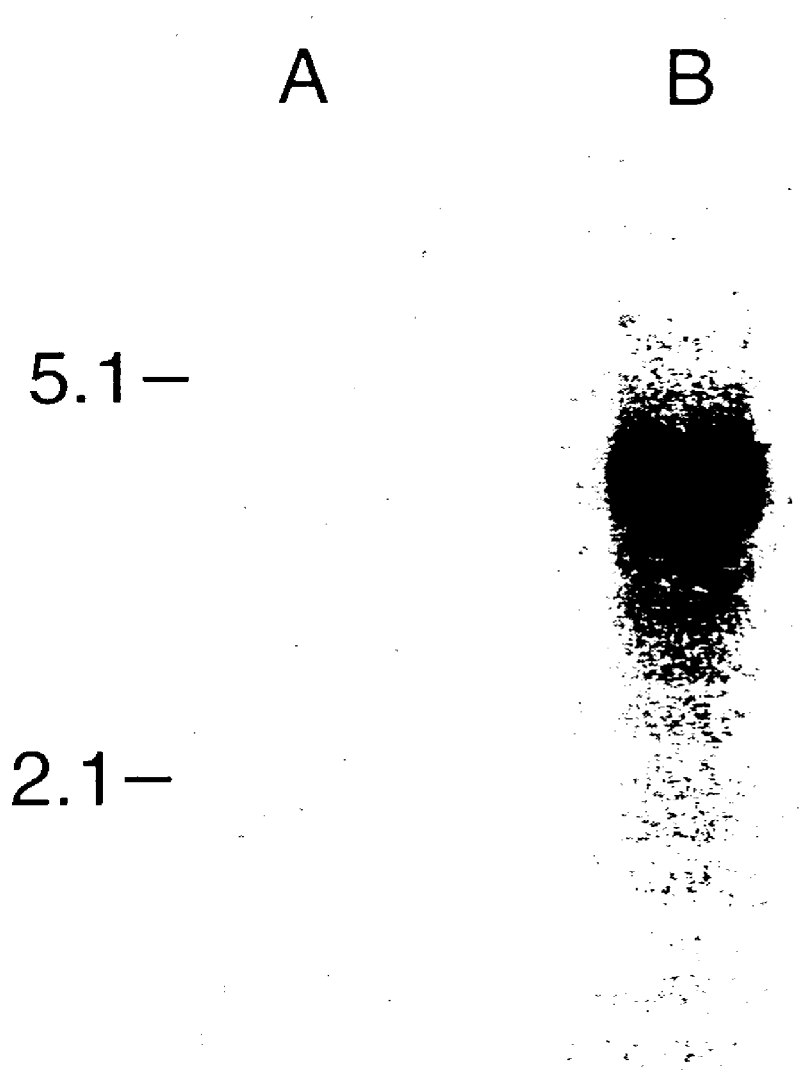

It was previously found that the mRNA for the SERA gene was probably abundant during late trophozoite-schizont stages because a large fraction (1.5%) of cDNA clones in that cDNA library hybridized with cDNA#366. Total RNA was isolated from late trophozoite-schizont stage parasites and was purified into poly (A)⁻ and poly(A)⁺ fractions by oligo-dT affinity chromatography. Northern blot analysis of the SERA mRNA revealed it was a single 4.1 kb species (FIG. 4). It was concluded that the mRNA was apparently very abundant because the 4.1 kb SERA mRNA in the Northern blot was easily detectable autoradiographically, requiring only a one minute exposure of the X-ray film. In addition, on the ethidium bromide stained gel prior to the blotting of the RNA, four stained bands in the smear of parasite mRNA could be visually detected, one of which corresponded in size with the 4.1 kb SERA mRNA. All available evidence suggests that both the SERA mRNA and protein are abundant during late trophozoite-schizont parasite stages.

Nucleotide Sequencing of SERA Genomic DNA

A P. falciparum genomic EcoRI library constructed in lambda gt11 was screened with $^{32}$P-labeled cDNA#366 and twelve positive phage clones were isolated. A genomic DNA clone that was plaque purified, clone E31, contained a 4.8 kb DNA insert (FIG. 5). Its sequence was determined and compared to the previously determined nucleotide sequence of the SERA cDNA (FIG. 1). Clone E31 contained sequences 5' to the unique EcoRI site in the SERA gene. Portions of its nucleotide sequence differed significantly from the sequence of the SERA cDNA. Because a 39 bp sequence was present in the SERA cDNA sequence, but was absent in clone E31, it was believed that clone E31 might not represent an expressed form (allele) of the gene that encoded the SERA antigen. To identify possible genomic DNA clones that corresponded to the allele encoding the cDNA defined SERA antigen, a 30 bp single-stranded oligonucleotide (probe A, see Methods section) was synthesized. That 30 base oligonucleotide was the antisense sequence of nucleotides 630 to 659 in the SERA cDNA sequence FIG. 2 (SEQ ID NO: 1), and contained part of the 39 bp sequence that was missing from clone E31. Probe A did not hybridize with clone E31.

$^{32}$P-labeled probe A was used to re-screen the genomic EcoRI library and eight of 40,000 phage plaques hybridized with probe A. Each of those eight plaque-purified clones contained a 4.8 kb EcoRI fragment that hybridized with the previously characterized SERA cDNA clones, cDNA#366 and cDNA#3102 (FIG. 1 and FIG. 5). One genomic DNA clone, clone E3C (FIG. 5), was subcloned into plasmid pUC19, and it was completely sequenced (nucleotides 1 to 4779 in FIG. 6). The sequence of clone E3C and the previously determined SERA cDNA sequence was identical in the coding region of the SERA gene. This result indicated that probe A specifically hybridized to an allele of the SERA gene that encoded the previously isolated SERA cDNA clones. The comparison of the sequence of clone E3C and clone E31 is summarized in Table II.

TABLE II

Nucleotide Differences Between the Nucleotide Sequence Defined by the cDNA Clones and Clone E3C (allele I), and the Clone E31 (allele II).

| Location[a] | Allele I[b] | Allele II |
| --- | --- | --- |
| 132 | A | C |
| 158 | A | G |
| between 1817 and 1818 | | TATATATATA |
| between 2047 and 2048 | | TT |
| 2151 | A | deleted |
| from 2478 to 2483 | GAAAAA | deleted |
| between 2649 and 2650[c] | | 24 bp insert[d] |
| 3087 | G | A |
| 3092 | A | T |
| 3096 | A | T |
| from 3098 to 3136 | 39 bp[e] | deleted |
| 3140 | C | T |
| 3149 | A | T |
| 3157 | G | A |
| 3185 | T | A |
| 3191 | A | T |
| from 3812 to 3815 | ATAT | deleted |
| 3993 | C | A |

[a]The nucleotide locations are based on the SERA genomic DNA sequence defined by cDNA and clone E3C (allele I) as shown in FIG. 6.
[b]The nucleotide sequence of clone E3C in the SERA coding region and the corresponding cDNA clones are identical. The previously determined SERA cDNA sequence was encoded between nucleotides 2304 and 5867 of the genomic DNA sequence in FIG. 6.
[c]As there are two identical 24-bp sequences in clone E31. This 24 bp insert may either be located between nucleotides 2649 and 2650 or 2673 and 2674.
[d]The 24 bp insert was 5' GTAATACAGGAGGAGGTCAAGCAG 3' (SEQ ID NO: 10).
[e]The 39 bp sequence was 5' GGGAACAGTTAGAGGAGATACAGAAC-CAA TTTCAGATTC 3' (SEQ ID NO: 11).

Clone E3C, that encoded the SERA mRNA defined by the previously sequenced SERA cDNA clones, was called allele I, while the clone E3 1 was considered to represent another SERA gene allele, allele II, not represented in SERA cDNA.

The 3' portion of the SERA gene was previously identified in clone MBN#3102 (FIG. 1 and FIG. 5), which was isolated by using cDNA#3102 to probe a P. falciparum MBN genomic DNA library. MBN#3102 was sequenced and its sequence was compared to the 4.8 kb fragments of allele I (clone E3C) and allele II (clone E31), as well as to the corresponding SERA cDNA sequences. The sequence 5' of the EcoRI site in MBN#3102 (FIG. 5) differed from the sequence of clone E3C by one nucleotide (nucleotide 3993, Table I) and was identical to the sequence of clone E31. Therefore, MBN#3102 represented allele II DNA (Table II). Because the 1.4 kb sequence 3' of the EcoRI site (FIG. 5) in MBN#3102 was identical to the 3' nucleotide sequence in the SERA cDNA, we concluded that the 3' genomic sequence of allele I was identical to that of allele II. The 6124 bp genomic DNA sequence containing the SERA gene, allele I, is shown in FIG. 6 (SEQ ID NO: 3).

Structure of the SERA Gene

The open reading frame which encoded the SERA antigen began with the ATG at nucleotide 2407 and ended at the TAA at nucleotide 5836 (FIG. 6) (SEQ ID NO: 3). The SERA gene (allele I and allele II) contained two separate regions of repeated amino acid sequences. One region in allele I which included amino acids 23 to 62 contained 5 copies of a degenerate octamer amino acid repeat. Allele II contained one additional octamer amino acid repeat in that region caused by a 24 bp insert (see Table II). The other amino acid repeat of allele I, which included amino acids 191 to 225, contained a polyserine repeat composed of 35 serine residues. The polyserine repeat was encoded by a hexanucleotide repeat, AG(T or C) TC(A or T). Allele II contained a polyserine repeat of only 34 serine residues because a 39 bp deletion (Table II) removed amino acids 178 to 191 (FIG. 3 and FIG. 6). Amino acid 191 is the first serine residue in the polyserine repeat of allele I. In addition, there were nucleotide differences between allele I and allele II in the polyserine repeat region (Table II, FIG. 6).

There were three large sequences present in SERA genomic DNA that were not found in SERA cDNA (FIG. 6). They were believed to be intron sequences of the SERA gene for several reasons. Those reasons were: a) all the presumed intron sequences contained nucleotides immediately flanking exon borders (FIG. 6) that conformed to the eukaryotic introns GT . . . AG junction rule (Mount, S. M. (1982) *Nucleic Acids Res.*, 10:459–472); b) all of these presumptive intron sequences had higher A+T contents (85–89%) than the surrounding exons (A+T content 71%); and c) each presumptive intron sequence contained multiple stop codons in each reading frame. Both SERA gene alleles contained three introns.

The genomic DNA contained a 2406 bp flanking sequence at the 5' end and a 286 bp flanking sequence at the 3' end of the gene. Both 5' and 3' flanking sequences contained higher A+T content (87%) than the coding sequence (71%) and also contained multiple stop codons in all reading frames. These differences between coding and flanking sequences have been observed in other *P. falciparum* genes (Weber, J. L, *Gene*, 52:103–109 (1987)). Another open reading frame was found at the 5' end of the clone E3C (FIG. 6) which started within the EcoRI site at the 5' end of the sequence and ended at nucleotide 485. The precise ends of the genomic DNA sequence that encode the SERA gene cannot be identified until the 5' and 3' mRNA termini and the SERA gene regulatory elements have been mapped.

Copy Number Analysis of the SERA Gene

Figure 8:
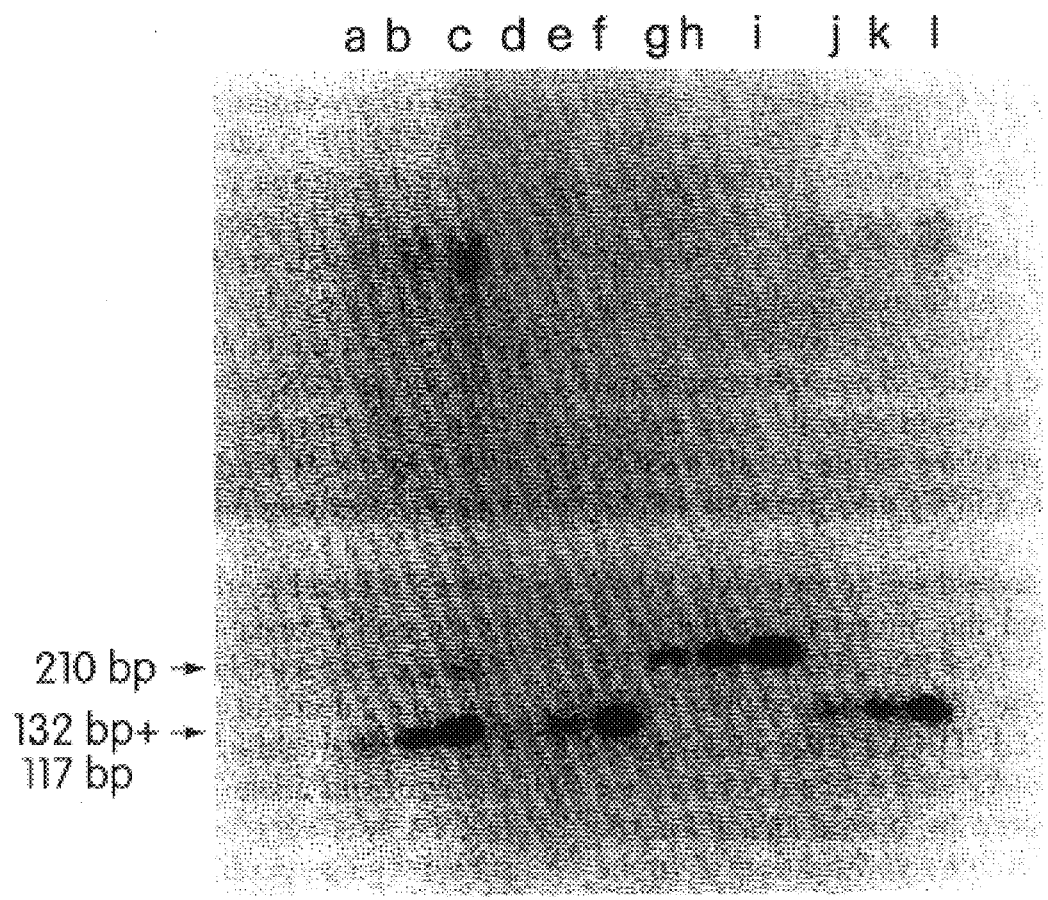

One explanation of the previously observed abundance of SERA gene mRNA (allele I) in late trophozoite and schizont stage parasites could be the presence of a high SERA gene copy number. The SERA gene copy number per parasite of allele I and allele II in the chromosomal DNA was therefore determined according to the Wellems method. Wellems, T. E. et al., *Cell*, 49:633–642 (1987). Alleles I and II were discriminated based on the observation that allele I contained an additional and unique HinfI restriction site (FIGS. 6 and 7, nucleotides 3132–3136) within the 39 bp sequence which was not present in allele II (Table II). Digestion of allele II with HinfI produced only one fragment (210 bp) while digestion of allele I with HinfI produced 2 fragments (117 bp and 132 bp) from that region. The DNA concentration of clone E3C, clone E31, FCR3, and Honduras-1 were quantitated both spectrophotometrically and by agarose gel electrophoresis. A defined amount of clone E3C, clone E31, FCR3, and Honduras-1 DNA was digested with HinfI, electrophoresed, and Southern blotted. The filter was hybridized with the purified and $^{32}$P-labeled 210 bp HinfI fragment of allele II (FIG. 8). Clone E3a (lanes g,h,i) contained only the 210 bp HinfI fragment used as the probe for Southern blot, while clone E3C (lanes d,e,f) contained the 117 bp and 132 bp fragments, which were not well resolved in the agarose gel. HinfI digestion of Honduras-1 genomic DNA produced the 117 bp and the 132 bp fragments only (lanes j,k,l), while digestions of FCR3 genomic DNA produced the 210 bp, 132 bp and 117 bp DNA fragments (lanes a,b,c). The results indicated that FCR3 genomic DNA contained both alleles, at unequal levels. A comparison between the binding of the probe to the genomic DNA and to both cloned alleles was made by optical density analysis of the autoradiograms (FIG. 8). The copy number of allele I and allele II was calculated to be 1.3 and 0.2 copies per FCR3 parasite based on the *P. falciparum* genomic size of 30,000 kb. Only allele I of the SERA gene was found in the *P. falciparum* Honduras-1 strain and was detected at a level of 1.1 copy per parasite.

Figure 9:
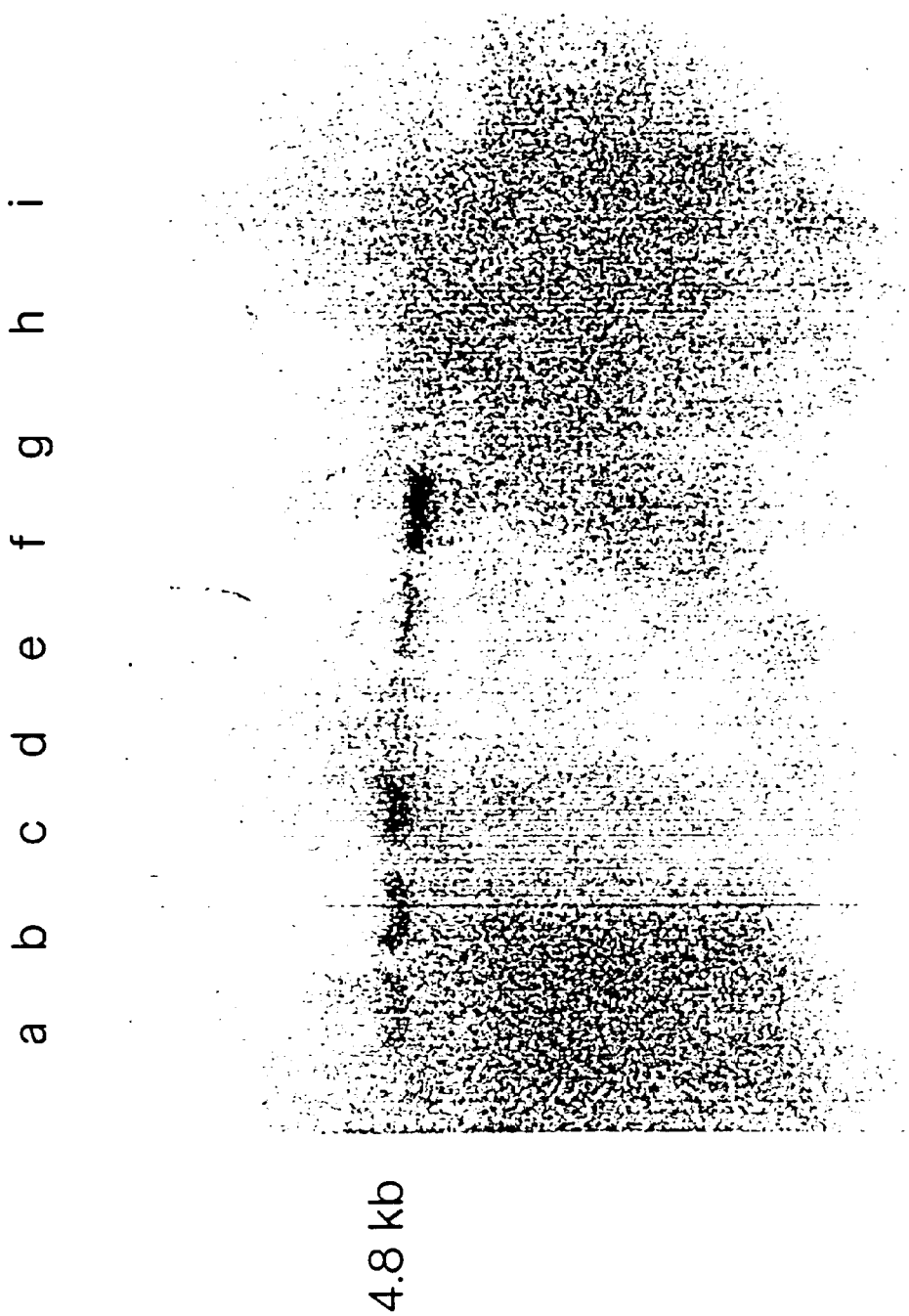

The copy number of allele I in FCR3 using probe A (probe A is specific for allele I) was also determined. As expected, probe A only hybridized to allele I (FIG. 9) and the copy number of allele I was determined to be 1.3 copies per parasite.

DISCUSSION

A lambda gt11 cDNA expression library was constructed from poly(A) RNA prepared from trophozoite and schizont enriched cultures of *P. falciparum*. About 1% of the clones containing cDNA inserts expressed antigens that were recognized by a pooled antimalarial Nigerian serum. A cDNA gene bank was established consisting of 288 independent antigen-expressing phage that reacted with parasite inhibitory Nigerian serum that strongly reacts with *P. falciparum* antigens. It was observed that a number of cDNA clones were recognized by a parasite inhibitory mMAb, 43E5. H (Banyal et al., *Am. J. Trop. Med. Hyg.*, 34:1055–1064 (1985)).

The cDNA366 was sequenced and it exhibited a well conserved homology to the partial genomic DNA sequence reported for a *P. falciparum* gene previously designated p126 (J. L. Weber et al., *Molecular Strategies of Parasitic Invasion*, Agabian, Goodman and Nogueira (eds.) p. 379–388, Alan R. Liss, Inc. NY (1987)). Their sequence was from a clone isolated from a genomic DNA library of the *P. falciparum* Camp strain screened by a monospecific rabbit antiserum against an "exported" parasite antigen reported to be a 126 kDa protein that was processed into antigens of 50, 47 and 18 kDa that were released into the culture supernatant (DelPlace et al., *Mol. Biochem. Parsitol.*, 23:193–201 (1987)). The MAb 43E5 reacted with antigens of 40 and 35 kd at all stages of development by Western blot analysis, though it reacted with greater intensity of binding to the schizont and merozoite preparations (H. Banyal et al., *Am. J. Trop. Med. Hyg.*, 34:1055–1064 (1985)). Some parts of the 126 kDa schizont precursor protein (i.e., 40 and 35 kDa peptides) may remain associated with the schizonts and merozoites and may be the only form of the original protein recognized by MAb 43E5. With the knowledge of the eDNA and amino acid sequence, we have been able to establish a structural basis for developing a malarial vaccine based upon the SERA gene has been established.

Among the 288 pre-screened Nigerian positive clones, 2.8% (8 clones) reacted with MAb 43E5 and 5H10. These frequencies might reflect the populations of each antibody in the pooled Nigerian serum that was used for the pre-screening of the original cDNA expression library. The estimation of the frequencies of clones that hybridized with cDNA#366 in the total cDNA library was 1.5%. While neither the frequency of phage plaques that are reactive with the mMAb nor the frequency of plaques that hybridize with the cDNA probe can provide an unambiguous measure of the relative expression of the gene coded for by the cDNAs, the results did suggest that the gene was expressed at relatively high frequencies. This was substantiated by the subsequent Northern blot analysis of the mRNA obtained from trophozoites and schizonts (FIG. 4).

The genomic DNA constituting the parasite SERA gene and its flanking sequence have been cloned and sequenced. The gene copy number was found to be one per parasite, which means that the high levels of mRNA and SERA protein are most likely related to a strong promoter which should be located in the 5' flanking region of the gene. This sequence should enhance the production of the SERA antigen when cloned and expressed in an appropriate host. In addition, the relation of the first SERA gene intron to the signal sequence (FIGS. 5 and 6) provides the potential for manipulating the signal sequence to improve the recovery of the SERA protein from the cloned gene that will be used to produce a genetically engineered protein.

In summary, the defining of the cDNA and gDNA sequences of the *P. falciparum* SERA gene opens a number of avenues for utilization of this knowledge for providing a vaccine and as a source of antigenic material to be used in diagnostic tests.

Example 2

Material and Methods
Bacteria, Plasmids, and Phage

The *E. coli* strains used here were BL21, BL21(DE3) (Studier, F. W., et. al. (1990) *Methods Enzymol.*, 185:60–89) and JM103 (Messing, J. (1983) *In Methods Enzymol.*, 101:20–78). Plasmids used here were pET-3a ( )Studier, F. W., et. al. (1990) *Methods Enzymol.*, 185:60–89, M13mp18, M13mp19 (Yanish-Perron, et al. (1985) *Gene* 33:103–1 19) and M13-pKM2, a derivative of M13 phage, which contains the T7 RNA polymerase gene under the control of lac promoter (Morimatsu, K., Ogawa, H. and Horii, T. (1933) *J. Mol. Biol.* in press).

Synthesis of Oligonucleotides

The oligonucleotides with a nucleotide length of 56 to 130 were synthesized using a Pharmacia LKB GENE ASSEMBLER PLUS DNA synthesizer. The products were purified by electrophoresis in a 10% polyacrylamide gel (50 mM Tris-borate, pH 8.3, 1 mM EDTA).

Reconstruction of the DHFR Gene

The purified oligonucleotides (17 pmol each) were annealed to form double strand DNA in a 50 μl reaction mixture containing 100 mM NaCl, 50 mM Tris-HCl(pH 7.6), 1 mM dithiothreitol, 0.1 mM EDTA. The products were electrophoresed in a 10% polyacrylamide gel in a buffer containing 50 mM Tris-borate (pH 8.3), 1 mM EDTA. The DNA electrophoresed at the proper position was eluted and used for ligation. Each of the annealed fragments was designed to contain the cohesive ends for ligation with M13mp18 or M13mp19 cut with appropriate restriction enzymes except for Nde I—Stu I unit (FIG. 17). This unit was ligated with pET-3a plasmid DNA cut with Nde I and Bam HI whose site was placed after the Stu I site in the synthetic oligonucleotides. The basic methods for ligation and cloning of DNA fragment followed were by Sambrook et al., (Sambrook, J., et al. (1989) *Molecular Cloning. A Laboratory manual*, Cold Spring Harbor Laboratory Press, Cold Spring Harbor, N.Y.). After cloning of each unit, the synthetic region was sequenced by the dideoxy DNA sequencing method (Sanger, F., et al. (1977) *Proc. Natl. Acad. Sci USA*, 74:5463–5467). Each synthesized DNA unit was confirmed by its sequence and ligated with the pET-3a containing Nde I—Bam HI unit to eventually give a plasmid, pET-PfDHFR, containing the complete DHFR gene.

Purification of the Reconstructed DHFR

The freshly transformed JM103 cells with pET-PfDHFR were grown in L-broth to 1×10⁸ cells ml⁻¹ at 37° C., at which time IPTG and M13-pKM2 phage was added at a final concentration of 50 μg ml⁻¹ and at multiplicity of infection (moi) 15 respectively. After 120 minutes incubation, cells were harvested and stored at −80° C. until used.

Subsequent operations were carried out at 4° C. and centrifugations were performed at 10,000 g for 20 min unless otherwise indicated. Frozen cells (5 g) were thawed and suspended in 45 ml of buffer A (20 mM potassium phosphate pH 7.0, 5 mM EDTA, 10 mM β-mercaptoethanol, 25% sucrose w/v). L,ysozyme was added to the suspension at a final concentration of 100 μg/ml. After incubation for 20 min on ice, the suspension was sonicated using a TOMY SEIKO ultrasonic disrupter Model UR-200P for 15 second periods until the viscosity was reduced. The pellet formed after centrifugation was collected and resuspended in 320 ml of buffer B (20 mM potassium phosphate pH7.0, 10 mM β-mercaptoethanol, 1 mM EDTA, 50 mM NaCl) containing 4 M guanidine HCl and sonicated to facilitate its solubilization. Immediately after the resuspension, 7680 ml of buffer C (20 mM potassium phosphate pH 7.0, 10 mM, β-mercaptoethanol, 10% glycerol v/v) was gradually added with stirring in 2 hr. The resulting solution was centrifuged at 8,000 rpm for 20 min at 4° C. to remove insoluble material. The supernatant was applied to a 5.0 cm×15.3 cm hydroxylapatite column previously equilibrated with buffer C, and washed with 400 ml of buffer D (150 mM potassium phosphate pH 7.0, 10 mM, β-mercaptoethanol, 10% glycerol v/v). The enzyme fractions were eluted with 250 ml of buffer E (400 mM potassium phosphate pH 7.0, 10 mM β-mercaptoethanol, 10% glycerol v/v). The active fractions were collected and subjected to dialysis against buffer F (90% saturated $(NH_4)_2SO_4$ solution containing 50 mM potassium phosphate pH 7.0, 10 mM β-mercaptoethanol, 10% glycerol) for 12 hours. The precipitate was collected by centrifugation and resuspended in 2 ml of buffer G (50 mM potassium phosphate pH 7.0, 10 mM β-mercaptoethanol, 400 mM $(NH_4)_2SO_4$, 1 mM EDTA, 10% glycerol). After the removal of undissolved materials by centrifugation, the suspension was applied to a 2.2 cm×90 cm SEPHACRYL S-300 HR column (Pharmacia) previously equilibrated with the same buffer. The active enzyme fractions were collected and subjected to dialysis against buffer F for 12 hours. The precipitate obtained was dissolved in 2 ml of buffer H (200 mM potassium phosphate pH 7.0, 10 mM β-mercaptoethanol, 400 mM $(NH_4)_2SO_4$, 1 mM EDTA, 20% glycerol v/v) and subjected to dialysis against the same buffer. The obtained fraction was kept at 0° C. until used.

The concentration of each purified DHFR was determined by absorbance at 278 nm, using $\epsilon_{278}=1.2$ M⁻¹. This value was calculated from the molecular extinction coefficients of amino acid residues in the constructed DHFR sequence.

Assay for DHFR Activity

DHFR activity was spectrophotometrically measured by the absorbance at 340 nm in a reaction mixture (200 μl) containing 50 mM TrisHCl (pH 7.6), 1 mM EDTA, 100 mM, β-mercaptoethanol, 100 μM NADPH, 100 μM DHF, 100 μg ml⁻¹ BSA, and an indicated amount of enzyme at 37° C. All components contained in 196 μl of reaction mixture except DHF were preincubated together at 37° C. for 2 min. The reaction was initiated by addition of 4 μl of 5 mM DHF. The decrease in $A_{340}$ was monitored by a HITACHI spectrophotometer U-2000. The blank sample consisted of all the reaction components except the enzyme. DHFR$^{Ser108}$ activity was measured as described above except that both concentrations of DHF and NADPH were 300 μM instead of 100 μM. The specific activity of the enzyme was calculated from the combined decreases in $A_{340}$ of NADPH and DHF by using the molar extinction coefficient of 12,300 $M^{-1}$ $cm^{-1}$ at 340 nm (Hillcoat, B. L. et al. (1967) *Analytical Biochem.*, 21:178–189). The inhibition of DHFR activity by pyrimethamine, methotrexate or trimethoprim was investigated by assaying the activity of DHFR at various substrate concentrations in the presence of several fixed concentrations of DHFR inhibitors.

Amino Acid Sequence Analysis

The amino acid sequence from the N-terminal end of the protein was determined by Edman degradation with an Applied Biosystems 473A protein sequencer.

RESULTS

Design and Construction of a Gene Encoding *P. falciparum* DHFR

The gene encoding DHFR part of the *P. falciparum* DHFR-TS complex was designed by changing codon usages based on the hypothesis that the *P. falciparum* sequence contains impediments for its expression in *E. coli*. The simplest hypothesis for achieving the efficient production of the active enzyme in *E. coli* would be to choose the most frequent codons used in *E. coli* for the synthetic gene. However, the possibility existed that the local velocity of the translation of the gene product could significantly influence the correct folding of secondary and tertiary structures of the protein. It is possible that the velocity of synthesis and thus folding could be affected by the presence of tracts of rare codons or frequent codons, although the mechanisms directing the folding of peptide synthesized de novo in a cell are still unknown. Based on this hypothesis, a DNA sequence encoding DHFR was designed by changing the original codons in *P. falciparum* to those used in the DHFR gene of *E. coli* (Smith, D. R. and Calvo, J. M. (1980) *Nucleic Acids Res.*, 8:2255–2274) at the identical or similar amino acid sites with the exception of codons that reside within the restriction sites required for facilitating the gene construction. Codons of amino acids which were absent in the *E. coli* DHFR sequence were constructed using moderately frequent codons of *E. coli*.

The amino (N-) terminus and carboxyl (C-) terminus of the constructed DHFR were decided as follows. At the N-terminus of the *P. falciparum* DHFR-TS, there are two consecutive methionines. Since *P. chabaudi* DHFR-TS has only one methionine in its N-terminus (Cowman, A. F. and Lew, A. M. (1989) *Mol. Cellular Biol.* 9:5182–5188), the second methionine in *P. falciparum* DHFR was taken as the N-terminal methionine in the constructed DHFR. As for the C-terminus, the amino acid sequence of *P. falciparum* DHFR-TS was compared with that of *E. coli* DHFR. The homology between the two sequences could extend to two consecutive lysines in *P. falciparum* which correspond to the consecutive two arginines at the C-terminus of *E. coli* DHFR (Smith, D. R. and Calvo, J. M. (1980) *Nucleic Acids Res.*, 8:2255–2274). Therefore, the translation termination codon TAA was placed after these two lysine codons.

The gene was divided into 5 blocks each of which was composed of 2 to 5 synthetic oligonucleotides. Each block was cloned and connected to each other after confirming their nucleotide sequences (see above). The DNA sequence thus constructed is shown in FIG. 17 (SEQ ID NO: 11). The constructed DHFR gene was inserted in an expression vector pET-3a utilizing a Nde I site at its first methionine and Bam HI site at the end, giving rise to the plasmid pET-PfDHFR$^{Ser108}$.

An additional oligonucleotide was synthesized with the alternative sequence directing a threonine residue at the Ser$^{108}$ position in the drug sensitive sequence. The thus constructed plasmid and its product were referred as pET-PfDHFR$^{Thr108}$ and DHFR$^{Thr108}$ respectively.

Expression of *P. falciparum* DHFR

The DHFR gene in pET-3a was placed under the T7 promoter that is recognized by T7 RNA polymerase but not by *E. coli* RNA polymerase. To control the possible toxicity caused by leaky synthesis, the plasmid pET-PfDHFR was introduced into an *E. coli* cell without the T7 RNA polymerase gene. The expression of the constructed DHFR gene was induced by infection with the M13-pKM2 phage which is a derivative of M13 phage containing the T7 RNA polymerase gene under the control of *E. coli* lac promotor (Morimatsu, K., Ogawa, H. and Horii, T. (1933) *J. Mol. Biol.* in press). When the DHFR gene was induced, a protein with a molecular weight of 27,000 was accumulated to about 30% of the total cellular protein as determined by SDS-polyacrylamide gel electrophoresis of the total proteins. The molecular weight of the protein observed by SDS-polyacrylamide gel electrophoresis matched that predicted from the nucleotide sequence of the DHFR gene.

Purification of DHFR

The DHFR activity was assayed in the supernatant fraction after centrifugation of the lysed cells containing a plasmid pET-PfDHFR$^{Ser108}$ or pET-PfDHFR$^{Thr108}$ by looking for any DHFR activity that exceeded the background of *E. coli* DHFR. None of the activity was found in the lysate of the cell containing pET-PfDHFR$^{Ser108}$ but it was found in the cell containing pET-PfDHFR$^{Thr108}$. Therefore the cell containing pET-PfDHFR$^{Thr108}$ was purified. Although the supernatant fraction had an excess of DHFR activity, the majority of the induced products was not in the supernatant fraction but rather in the pellet fraction (FIG. 18, lane 5). Therefore, several reagents including urea, β-mercaptoethanol and guanidine HCl were used to try to solubilize and reactivate the protein. Among them, 4 M guanidine HCl solubilized the precipitate and the DHFR activity appeared after lowering the concentration of guanidine HCl. The reactivated DHFR was subjected to purification with by hydroxylapatite and the SEPHACRYL S-300 HR column chromatography (see above). In the S-300 chromatography, DHFR activity was eluted at the position of a molecular weight of 27,000, indicating that DHFR behaved as monomer. About 10 mg of the protein with 98% purity was prepared from 5 g of cell paste using these procedures (Table III and FIG. 18, lane 7). The N-terminal amino acid sequence of the purified protein was shown to be identical to that from the nucleotide sequence by ten cycles of Edman degradations. The DHFR$^{Ser108}$ was also reactivated by the same procedure and purified. Although the total yield of both enzymes were about ten fold less than the DHFR$_{Thr108}$, both enzymes were similarly stable for at least a month under the described conditions.

TABLE III

| | Protein (mg/ml) | Volume (ml) | Total protein (mg) | Specific activity (n mol/min)/ mg protein) | Total activity (n mol/min) |
|---|---|---|---|---|---|
| Dilution of Glu-HCl | 0.0365 | 8000 | 292.0 | 9000 | 2628000 |
| Hydroxyla- patite colummn | 0.42 | 75 | 31.5 | 62000 | 1953000 |
| S-300 column | 0.21 | 60 | 12.6 | 69000 | 869000 |
| Ammonium sulfate concentration | 25.1 | 0.43 | 10.8 | 69000 | 745000 |

Characterization of the DHFR Activity

The kinetic characterization of the purified recombinant DHFR$^{Ser108}$ showed that Km values for DHF and NADPH were 67 mM and 90 mM respectively (Table IV). Both values were about 20 times higher than those reported for the DHFR-TS prepared from the drug sensitive *P. falciparum* 3D7 strain (Walter, R. D. (1986) *Mol. Biochem. Parasitol.* 19:61–66; Chen, G.-X., et al. (1987) *Mol. Pharmacol.* 31:430–437) of which the DHFR part has the identical amino acid sequence of DHFR$^{Ser108}$. In contrast, the Km values of DHFR$^{Thr108}$ for DHF and NADPH were 17 mM and 19 mM respectively. The Ki values for the DHFR inhibitors including pyrimethamine, methotrexate and trimethoprim were determined by the Dixon plot analyses. All of these compounds inhibited enzyme in a competitive manner (FIGS. 19A–19F). The Ki values obtained are summarized in Table IV.

TABLE IV

|  | Reconstructed P.f. DHFR | |
| --- | --- | --- |
|  | Thr108 | Ser108 |
| Specific activity (nmol/min/mg protein) | 69,000 | 36,600 |
| Km$^{DHF}$ (μM) | 16.8 ± 0.6 | 66.6 ± 2.6 |
| Km$^{NADPH}$ (μM) | 19.2 ± 0.4 | 90.2 ± 4.3 |
| Ki$^{Pyr}$ (nM) | 0.14 ± 0.02 | 4.14 ± 0.16 |
| Ki$^{TMP}$ (nM) | 143 ± 21 | 161.4 ± 3.5 |
| Ki$^{MTX}$ (nM) | 0.86 ± 0.08 | 1.28 ± 0.05 |

Since the recombinant DHFR was reactivated, the enzyme preparation might contain a fraction of inactive molecules. To examine this possibility, the enzyme molecules were titrated with pyrimethamine, methotrexate and trimethoprim. FIGS. 20A–20B show that 50% inhibition of DHFR$^{Thr108}$ activity was achieved when a 1:2 ratio of pyrimethamine or methotrexate and enzyme molecules were included in the reaction. Since the concentration of enzyme in the reaction was 3 nM which is much higher than Ki values for these inhibitors, the results suggest that almost all of the enzymes are active molecules in both DHFR$^{Thr108}$ and DHFR$^{Ser108}$ preparations. In contrast, trimethoprim inhibited the activity at the concentration of its Ki which is much higher than the concentration of enzyme in the reaction (FIG. 20C).

Example 3

The expression of portions of the SERA protein followed that for DHFR in Example 2 except where noted. The purification of the expressed proteins was as described below.

The two parts of SERA to be expressed were: a) SE47' (FIG. 11) which encodes amino acids 17–382 which correspond to the original SERA clone cDNA #366 that encodes amino acids 9–354. SE47 (SEQ ID NO: 18)(FIG. 21) encodes the 17 amino acid signal sequence at the N-terminal end of the protein as well as the rest of SE47' amino acids 1 to 382 (SEQ ID NO: 14)); and b) the portion of the 50 kd processed protein, SE50A (FIG. 12), that encodes the conserved amino acid sequences potentially having a proteinase function (SEQ ID NO: 16).

The SE50A product can be produced as up to 30–40% of the total *E. coli* protein. It is produced as an insoluble inclusion body that can be recovered in purified form by breaking the cells and pelleting the inclusion bodies.

The SE47 gene product was not synthesized in *E. coli*. However, the SE47' gene product, in which the signal peptide coding sequence was excluded, was produced in high amounts. The SE47' product was produced in soluble form and represents 30–40% of total *E. coli* protein.

The expression of portions of SERA was substantially the same as that for DHFR in Example 2 except where noted.

Expression of the material involved first resynthesizing the genetic information after selecting a codon preference that took into account both the *P. falciparum* codon preference and the *E. coli* codon preference. No SERA protein exists in *E. coli*, therefore, the following codon selection strategy was devised. A table of codon frequencies for "all" *P. falciparum* proteins was established as was a table of codon frequencies for "all" *E. coli* proteins Table V. If an amino acid in SERA was encoded by a codon that was the second most frequently used codon for that amino acid then the corresponding *E. coli* for that amino acid was selected for the gene. This strategy was chosen to provide comparable translation velocities that could influence protein folding and protein activity of the product produced in *E. coli*.

TABLE V

Comparison of codon usage in *P. falciparum* and *E. coli*

|  |  | P. falciparum | E. coli |  |  | P. falciparum | E. coli |
| --- | --- | --- | --- | --- | --- | --- | --- |
| Phe | TTT | 2.49 | TTT 1.85 | Ser | TCA | 2.51 | AGC 1.50 |
|  | TTC | 1.01 | TTC 1.82 |  | AGT | 2.25 | TCT 1.04 |
|  |  |  |  |  | TCT | 1.44 | TCC 0.96 |
| Leu | TTA | 5.12 | CTG 5.48 |  | TCC | 0.67 | TCG 0.79 |
|  | CTT | 0.98 | TTG 1.12 |  | AGC | 0.42 | AGT 0.71 |
|  | TTG | 0.81 | TTA 1.03 |  | TCG | 0.11 | TCA 0.63 |
|  | CTA | 0.34 | CTT 0.99 |  |  |  |  |
|  | CTC | 0.22 | CTC 0.98 | Pro | CCA | 2.80 | CCG 2.42 |
|  | CTG | 0.04 | CTA 0.30 |  | CCT | 1.08 | CCA 0.81 |
|  |  |  |  |  | CCC | 0.32 | CCT 0.65 |
| Ile | ATT | 2.69 | ATC 2.71 |  | CCG | 0.06 | CCC 0.42 |
|  | ATA | 2.31 | ATT 2.70 |  |  |  |  |
|  | ATC | 0.40 | ATA 0.38 | Thr | ACA | 2.39 | ACC 2.46 |
|  |  |  |  |  | ACT | 1.86 | ACG 1.25 |
| Met | ATG | 1.82 | ATG 2.65 |  | ACC | 0.62 | ACT 1.05 |
|  |  |  |  |  | ACG | 0.19 | ACA 0.64 |
| Val | GTT | 2.19 | GTG 2.53 |  |  |  |  |
|  | GTA | 2.11 | GTT 2.04 | Ala | GCA | 2.68 | GCG 3.33 |
|  | GTC | 0.31 | GTC 1.43 |  | GCT | 2.07 | GCC 2.37 |
|  | GTG | 0.29 | GTA 1.18 |  | GCC | 0.70 | GCA 2.06 |
|  |  |  |  |  | GCG | 0.07 | GCT 1.78 |
| Tyr | TAT | 3.29 | TAT 1.49 | Cys | TGT | 1.33 | TGC 0.62 |
|  | TAC | 0.59 | TAC 1.34 |  | TGC | 0.25 | TGT 0.47 |
| * | TAA | 0.13 | TAA 0.20 | Trp | TGG | 0.45 | TGG 1.28 |
| * | TAG | 0.02 | TGA 0.08 |  |  |  |  |
| * | TGA | 0.02 | TAG 0.02 | Arg | AGA | 1.66 | CGT 2.47 |

TABLE V-continued

Comparison of codon usage in
P. falciparum and E. coli

| | P. falciparum | | E. coli | | | P. falciparum | | E. coli |
|---|---|---|---|---|---|---|---|---|
| | | | | | | CGT | 0.33 | CGC 2.20 |
| His | CAT | 1.90 | CAT | 1.15 | | AGG | 0.28 | CGG 0.46 |
| | CAC | 0.93 | CAC | 1.10 | | CGA | 0.15 | CGA 0.31 |
| | | | | | | CGC | 0.02 | AGA 0.20 |
| Gln | CAA | 2.65 | CAG | 3.01 | | CGG | 0.01 | AGG 0.13 |
| | CAG | 0.27 | CAA | 1.30 | | | | |
| | | | | | Gly | GGA | 3.14 | GGC 3.07 |
| Asn | AAT | 7.41 | AAC | 2.42 | | GGT | 2.54 | GGT 2.80 |
| | AAC | 2.11 | AAT | 1.59 | | GGC | 0.19 | GGG 0.96 |
| | | | | | | GGG | 0.19 | GGA 0.67 |
| Lys | AAA | 8.46 | AAA | 3.69 | | | | |
| | AAG | 1.56 | AAG | 1.19 | | | | |
| Asp | GAT | 5.58 | GAT | 3.20 | | | | |
| | GAC | 0.79 | GAC | 2.23 | | | | |
| Glu | GAA | 7.55 | GAA | 437 | | | | |
| | GAG | 0.81 | GAG | 193 | | | | |

For the transcription system used in E. coli, the T7 promoter was placed at the 5' end of the SERA sequence to be expressed. The synthetic gene was inserted into the NdeI and BamHI sites in pET3a expression vector (Studier et al. (1990) Meth. Enzymol. 185:60–89). The thus constructed plasmid was introduced into the E. coli XL-1 blue strain. The plasmid with the T7 promoter-SE47' or SE50A was carried in an E. coli strain that does not contain T7 RNA polymerase. No leaky transcription and translation of the gene was therefore possible. Leaky expression causes a toxic effect that kills the host bacterium and may be one cause of a low yield of the cloned gene product. When the cells had grown to the density of $1 \times 10^8$ cells/ml in LB broth, expression of SE47' or SE50A was initiated by infecting the cells with an M13 phage derivative containing the T7 RNA polymerase gene at m.o.i. 20. The stage of E. coli growth (i.e., $1 \times 10^8$ cells/ml in log phase) at which time phage infection occurs is important for the yield of SERA product. Too many cells or altered growth conditions at the time of infection significantly reduces the protein yield. After additional incubation at 37° C. for 3 hours, cells were harvested and analyzed by SDS-polyacrylamide gel electrophoresis (12.5%).

SDS-Polyacrylamide Gel Electrophoresis of the Recombinant SERA Protein Induced in E. coli Cells Phage-infected whole cells carrying either only a plasmid pET3a or plasmid and DNA insert SE50A or SE47', were lysed with lysing solution containing 1% sodium dodecyl sulfate (SDS) and 2-mercaptoethanol and run on a SDS-polyacrylamide gel (12.5%). Protein bands were visualized with Coomassie staining. The lanes in FIG. 13 contained: M, molecular weight standards; pET3a, cell containing vector DNA; SE50A, cell containing pET3a-SE50A plasmid; SE47', cell containing pET3a-SE47' plasmid. As shown in FIG. 13, the bulk of total protein of the SE47' is around 40 kd (365 amino acids) and the SE50A product is at the lower size corresponding to 234 amino acids. FIG. 14 shows the recombinant protein induced in E. coli cells. In FIG. 14, the SE50A product is in the pellet (P) and the whole cell extract (W) and not in the soluble part of the extract. The SE47' product is in the soluble (S) and whole cell extract (W) and not the pellet. The purified inclusion body protein (Ib) is a marker. These specific products react with the appropriate antibody just as antibodies to SE47' and SE50A react with SERA total protein (FIG. 15).

ELISA Value of Mouse and Rat Sera Immunized with the Recombinant SERA Protein, SE47' and SF50A The SE47' protein was prepared as follows: the cleared lysate of the induced E. coli cell containing the pET3a-SE47' plasmid was run on a SDS-polyacrylamide gel (12.5%). The gel block containing SF47' protein was ground then mixed with Freund's complete adjuvant. Three mice were injected subcutaneously with the mixture. After two weeks, boost injections were made with Freund's incomplete adjuvant.

The SE50A protein was produced in E. coli cells as described for SE47'. The products were obtained as an inclusion body in the precipitate of lysed cells. The precipitate was solubilized with a buffer containing 5M guanidine HCl. After removal of insoluble materials, SE50A protein was precipitated by removing the 5M guanidine HCl again. These processes were repeated 3 times. The final precipitate contained SE50A at more than 80% purity. Three rats were immunized by subcutaneous injection of the insoluble form of SE50A without adjuvant three times on days 1, 22, and 50. The ELISA values of the mice and rats immunized with SE47' or SE50A are shown in Table VI.

Immunization of mice with SE47' using Freund's adjuvant produced effective parasite inhibitory antibodies (FIG. 16B). Immunization of mice with SE50A inclusion body material in an insoluble form without Freund's adjuvant produced antibodies but was indistinguishable from control serum except at the lowest dilution (less than 1/20) (FIG. 16A).

TABLE VI

| SE47' (Mouse) | ELISA Titer | SE50A (Rat) | ELISA Titer |
|---|---|---|---|
| 1 | 12,000 | 1 | 10,000 |
| 2 | 14,000 | 2 | 8,330 |
| 3 | 22,000 | 3 | 8,330 |
| C | <200 | C | <50 |

Immunoblot of Whole Cellular Proteins of Plasmodium falciparum FCR3 Strain with Antiserum Against SE47' or SE50A Parasite cells were isolated by saponin lysis of the in vitro culture. The prepared cells were analyzed by immunoblotting using SDS-polyacrylamide gel electrophoresis (12.5%). The antisera used for the immunoblot (FIG. 15) were as follows: lane 1, control mouse serum; lane 2, mouse #3 anti-SE47' serum; lane 3, control rat serum; lane 4, rat #1 anti-SE50A serum. The arrow indicates the molecular weight corresponding to SERA protein.

Plasmodium falciparum Growth Inhibition with Anti-SERA Serum

The Plasmodium falciparum cell (FCR3) was grown in an in vitro culture containing 5% red blood cells (RBC). When the parasitized RBC, 96% were trophozoite and schizont, reached 4.4% of total RBC, the culture was diluted to 1% of parasitized cell in total RBC and 2% of RBC in medium. The 100 l of the diluted culture was incubated in a 96 well dish. The culture media which contains rat or mouse serum at the indicated dilution were changed each 24 hours. Parasitemia was measured by Giemsa staining after 72 hours incubation. The results are shown in FIGS. 16A–16B. The sera used here were from the animal #3 of SE47' and #1 of SE50A, each of whose ELISA titer was described in Table VI.

Equivalents

Those skilled in the art will recognize or be able to ascertain, using no more than routine experimentation, many equivalents to the specific materials and components described herein. Such equivalents are intended to be encompassed in the scope of the following claims.

What is claimed is:

1. An isolated and purified nucleic acid molecule, encoding an immunogenic protein of *Plasmodium falciparum*, comprising a nucleotide sequence selected from the group consisting of: SEQ ID. NO:1 (FIG. 2). SEQ ID NO:3 (FIG. 6), and a nucleotide sequence completely complementary to SEQ ID NO:1 (FIG. 2) or SEQ ID NO:3 (FIG. 6).

2. An expression vector comprising the nucleic acid molecule of claim 1.

3. A cell transformed with the expression vector of claim 2.

4. An isolated and purified DNA molecule comprising nucleotide sequence SEQ ID NO:1 (FIG. 2).

5. A recombinant plasmid comprising the isolated DNA molecule of claim 4.

6. An isolated and purified nucleic acid molecule, encoding an immunogenic protein of *Plasmodium falciparum*, consisting of a nucleotide sequence selected from the group consisting of: SEQ IN NO:1 (FIG. 2), SEQ ID NO:3 (FIG. 6), and a nucleotide sequence completely complementary to SEQ ID NO:1 (FIG. 2) or SEQ ID NO:3 (FIG. 6).

7. An isolated and purified DNA molecule consisting of nucleotide sequence SEQ ID NO:1 (FIG. 2).

8. An isolated and purified DNA molecule comprising nucleotide sequence SEQ ID NO:20 (nucleotides 126–1183 of SEQ ID NO:1).

9. An isolated and purified DNA molecule consisting of nucleotide sequence SEO ID NO:20 (nucleotides 126–1 183 of SEQ ID NO:1.

10. An isolated nucleic acid molecule comprising nucleotide sequence SEQ ID NO:14 (FIG. 11).

11. An isolated nucleic acid molecule consisting of nucleotide sequence SEQ ID NO:14 (FIG. 11).

12. An isolated nucleic acid molecule comprising nucleotide sequence SEQ ID NO:16 (FIG. 12).

13. An isolated nucleic acid molecule consisting of nucleotide sequence SEQ ID NO:16 (FIG. 12).

* * * * *

```
                        SEQUENCE LISTING

<160> NUMBER OF SEQ ID NOS:  20

<210> SEQ ID NO 1
<211> LENGTH: 3107
<212> TYPE: DNA
<213> ORGANISM: Plasmodium falciparum
<220> FEATURE:
<221> NAME/KEY: CDS
<222> LOCATION: (104)..(3070)

<400> SEQUENCE: 1
aaaatacata tattataaca taaagaaaaa ttaaataaat caaacatatt caaaaaaatt      60
aaagttctta aaatattata taacttaata ctcatatatc aaa atg aag tca tat     115
                                                Met Lys Ser Tyr
                                                  1 att tcc ttg ttt ttc ata ttg tgt gtt ata ttt aac aaa aat gtt ata     163
Ile Ser Leu Phe Phe Ile Leu Cys Val Ile Phe Asn Lys Asn Val Ile
  5                  10                  15                  20 aaa tgt aca gga gaa agt caa aca ggt aat aca gga gga ggt caa gca     211
Lys Cys Thr Gly Glu Ser Gln Thr Gly Asn Thr Gly Gly Gly Gln Ala
                 25                  30                  35 ggt aat aca gta gga gat caa gca ggt agt aca gga gga agt cca caa     259
Gly Asn Thr Val Gly Asp Gln Ala Gly Ser Thr Gly Gly Ser Pro Gln
             40                  45                  50 ggt agt acg gga gca agt caa ccc gga agt tcc gaa cca agc aat cct     307
Gly Ser Thr Gly Ala Ser Gln Pro Gly Ser Ser Glu Pro Ser Asn Pro
         55                  60                  65 gta agt tcc gga cat tct gta agt act gta tca gta tca caa act tca     355
Val Ser Ser Gly His Ser Val Ser Thr Val Ser Val Ser Gln Thr Ser
     70                  75                  80 act tct tca gaa aaa cag gat aca att caa gta aaa tca gct tta tta     403
Thr Ser Ser Glu Lys Gln Asp Thr Ile Gln Val Lys Ser Ala Leu Leu
 85                  90                  95                 100 aaa gat tat atg ggt tta aaa gtt act ggt cca tgt aac gaa aat ttc     451
Lys Asp Tyr Met Gly Leu Lys Val Thr Gly Pro Cys Asn Glu Asn Phe
                105                 110                 115 ata atg ttc tta gtt cct cat ata tat att gat gtt gat aca gaa gat     499
Ile Met Phe Leu Val Pro His Ile Tyr Ile Asp Val Asp Thr Glu Asp
            120                 125                 130 act aat atc gaa tta aga aca aca ttg aaa gaa aca aat aat gca ata     547
Thr Asn Ile Glu Leu Arg Thr Thr Leu Lys Glu Thr Asn Asn Ala Ile
        135                 140                 145 tca ttt gaa tca aac agt ggt tca tta gaa aaa aaa aaa tat gta aaa     595
Ser Phe Glu Ser Asn Ser Gly Ser Leu Glu Lys Lys Lys Tyr Val Lys
    150                 155                 160 cta cca tca aat ggt aca act ggt gaa caa ggt tca agt acg gga aca     643
Leu Pro Ser Asn Gly Thr Thr Gly Glu Gln Gly Ser Ser Thr Gly Thr
165                 170                 175                 180 gtt aga gga gat aca gaa cca att tca gat tca agc tca agt tca agt     691
Val Arg Gly Asp Thr Glu Pro Ile Ser Asp Ser Ser Ser Ser Ser Ser
                185                 190                 195
```

```
tca agt tct agt tca agt tca agt tca agt tct agt tca agt tca agt        739
Ser Ser Ser Ser Ser Ser Ser Ser Ser Ser Ser Ser Ser Ser Ser Ser
            200                 205                 210 tca agt tca agt tct agt tca agt tct agt tca agt tca gaa agt ctt        787
Ser Ser Ser Ser Ser Ser Ser Ser Ser Ser Ser Ser Ser Glu Ser Leu
            215                 220                 225 cct gct aat gga cct gat tcc cct act gtt aaa ccg cca aga aat tta        835
Pro Ala Asn Gly Pro Asp Ser Pro Thr Val Lys Pro Pro Arg Asn Leu
230                 235                 240 caa aat ata tgt gaa act gga aaa aac ttc aag ttg gta gta tat att        883
Gln Asn Ile Cys Glu Thr Gly Lys Asn Phe Lys Leu Val Val Tyr Ile
245                 250                 255                 260 aag gag aat aca tta ata att aaa tgg aaa gta tac gga gaa aca aaa        931
Lys Glu Asn Thr Leu Ile Ile Lys Trp Lys Val Tyr Gly Glu Thr Lys
            265                 270                 275 gat act act gaa aat aac aaa gtt gat gta aga aag tat ttg ata aat        979
Asp Thr Thr Glu Asn Asn Lys Val Asp Val Arg Lys Tyr Leu Ile Asn
                280                 285                 290 gaa aag gaa acc cca ttt act agt ata cta ata cat gcg tat aaa gaa       1027
Glu Lys Glu Thr Pro Phe Thr Ser Ile Leu Ile His Ala Tyr Lys Glu
295                 300                 305 cat aat gga aca aac tta ata gaa agt aaa aac tac gca tta gga tca       1075
His Asn Gly Thr Asn Leu Ile Glu Ser Lys Asn Tyr Ala Leu Gly Ser
310                 315                 320 gac att cca gaa aaa tgt gat acc tta gct tcc aat tgc ttt tta agt       1123
Asp Ile Pro Glu Lys Cys Asp Thr Leu Ala Ser Asn Cys Phe Leu Ser
325                 330                 335                 340 ggt aat ttt aac att gaa aaa tgc ttt caa tgt gct ctt tta gta gaa       1171
Gly Asn Phe Asn Ile Glu Lys Cys Phe Gln Cys Ala Leu Leu Val Glu
            345                 350                 355 aaa gaa aat aaa aat gac gta tgt tac aaa tac cta tct gaa gat att       1219
Lys Glu Asn Lys Asn Asp Val Cys Tyr Lys Tyr Leu Ser Glu Asp Ile
            360                 365                 370 gta agt aac ttc aaa gaa ata aaa gct gag aca gaa gat gat gat gaa       1267
Val Ser Asn Phe Lys Glu Ile Lys Ala Glu Thr Glu Asp Asp Asp Glu
            375                 380                 385 gat gat tat act gaa tat aaa tta aca gaa tct att gat aat ata tta       1315
Asp Asp Tyr Thr Glu Tyr Lys Leu Thr Glu Ser Ile Asp Asn Ile Leu
390                 395                 400 gta aaa atg ttt aaa aca aat gaa aat aat gat aaa tca gaa tta ata       1363
Val Lys Met Phe Lys Thr Asn Glu Asn Asn Asp Lys Ser Glu Leu Ile
405                 410                 415                 420 aaa tta gaa gaa gta gat gat agt ttg aaa tta gaa tta atg aat tac       1411
Lys Leu Glu Glu Val Asp Asp Ser Leu Lys Leu Glu Leu Met Asn Tyr
            425                 430                 435 tgt agt tta ctt aaa gac gta gat aca aca ggt acc tta gat aat tat       1459
Cys Ser Leu Leu Lys Asp Val Asp Thr Thr Gly Thr Leu Asp Asn Tyr
            440                 445                 450 ggg atg gga aat gaa atg gat ata ttt aat aac tta aag aga tta tta       1507
Gly Met Gly Asn Glu Met Asp Ile Phe Asn Asn Leu Lys Arg Leu Leu
            455                 460                 465 att tat cat tca gaa gaa aat att aat act tta aaa aat aaa ttc cgt       1555
Ile Tyr His Ser Glu Glu Asn Ile Asn Thr Leu Lys Asn Lys Phe Arg
470                 475                 480 aat gca gct gta tgt ctt aaa aat gtt gat gat tgg att gta aat aag       1603
Asn Ala Ala Val Cys Leu Lys Asn Val Asp Asp Trp Ile Val Asn Lys
485                 490                 495                 500 aga ggt tta gta tta cct gaa tta aat tat gat tta gaa tat ttc aat       1651
Arg Gly Leu Val Leu Pro Glu Leu Asn Tyr Asp Leu Glu Tyr Phe Asn
            505                 510                 515
```

```
gaa cat tta tat aat gat aaa aat tct cca gaa gat aaa gat aat aaa   1699
Glu His Leu Tyr Asn Asp Lys Asn Ser Pro Glu Asp Lys Asp Asn Lys
            520                 525                 530 gga aaa ggt gtc gta cat gtt gat aca act tta gaa aaa gaa gat act   1747
Gly Lys Gly Val Val His Val Asp Thr Thr Leu Glu Lys Glu Asp Thr
        535                 540                 545 tta tca tat gat aac tca gat aat atg ttt tgt aat aaa gaa tat tgt   1795
Leu Ser Tyr Asp Asn Ser Asp Asn Met Phe Cys Asn Lys Glu Tyr Cys
    550                 555                 560 aac aga tta aaa gat gaa aat aat tgt ata tct aat ctt caa gtt gaa   1843
Asn Arg Leu Lys Asp Glu Asn Asn Cys Ile Ser Asn Leu Gln Val Glu
565                 570                 575                 580 gat caa ggt aat tgt gat act tca tgg att ttt gct tca aaa tat cat   1891
Asp Gln Gly Asn Cys Asp Thr Ser Trp Ile Phe Ala Ser Lys Tyr His
            585                 590                 595 tta gaa act att aga tgt atg aaa gga tat gaa cct acc aaa att tct   1939
Leu Glu Thr Ile Arg Cys Met Lys Gly Tyr Glu Pro Thr Lys Ile Ser
        600                 605                 610 gct ctt tat gta gct aat tgt tat aaa ggt gaa cat aaa gat aga tgt   1987
Ala Leu Tyr Val Ala Asn Cys Tyr Lys Gly Glu His Lys Asp Arg Cys
    615                 620                 625 gat gaa ggt tct agt cca atg gaa ttc tta caa att att gaa gat tat   2035
Asp Glu Gly Ser Ser Pro Met Glu Phe Leu Gln Ile Ile Glu Asp Tyr
630                 635                 640 gga ttc tta cca gca gaa tca aat tat cca tat aac tat gtg aaa gtt   2083
Gly Phe Leu Pro Ala Glu Ser Asn Tyr Pro Tyr Asn Tyr Val Lys Val
645                 650                 655                 660 gga gaa caa tgt cca aag gta gaa gat cac tgg atg aat cta tgg gat   2131
Gly Glu Gln Cys Pro Lys Val Glu Asp His Trp Met Asn Leu Trp Asp
            665                 670                 675 aat gga aaa atc tta cat aac aaa aat gaa cct aat agt tta gat ggt   2179
Asn Gly Lys Ile Leu His Asn Lys Asn Glu Pro Asn Ser Leu Asp Gly
        680                 685                 690 aag gga tat act gca tat gaa agt gaa aga ttt cat gat aat atg gat   2227
Lys Gly Tyr Thr Ala Tyr Glu Ser Glu Arg Phe His Asp Asn Met Asp
    695                 700                 705 gca ttt gtt aaa att att aaa act gaa gta atg aat aaa ggt tca gtt   2275
Ala Phe Val Lys Ile Ile Lys Thr Glu Val Met Asn Lys Gly Ser Val
710                 715                 720 att gca tat att aaa gct gaa aat gtt atg gga tat gaa ttt agt gga   2323
Ile Ala Tyr Ile Lys Ala Glu Asn Val Met Gly Tyr Glu Phe Ser Gly
            725                 730                 735                 740 aag aaa gta cag aac tta tgt ggt gat gat aca gct gat cat gca gtt   2371
Lys Lys Val Gln Asn Leu Cys Gly Asp Asp Thr Ala Asp His Ala Val
        745                 750                 755 aat att gtt ggt tat ggt aat tat gtg aat agc gaa gga gaa aaa aaa   2419
Asn Ile Val Gly Tyr Gly Asn Tyr Val Asn Ser Glu Gly Glu Lys Lys
    760                 765                 770 tcc tat tgg att gta aga aac agt tgg ggt cca tat tgg gga gat gaa   2467
Ser Tyr Trp Ile Val Arg Asn Ser Trp Gly Pro Tyr Trp Gly Asp Glu
775                 780                 785 ggt tat ttt aaa gta gat atg tat gga cca act cat tgt cat ttt aac   2515
Gly Tyr Phe Lys Val Asp Met Tyr Gly Pro Thr His Cys His Phe Asn
            790                 795                 800 ttt att cac agt gtt gtt ata ttc aat gtt gat tta cct atg aat aat   2563
Phe Ile His Ser Val Val Ile Phe Asn Val Asp Leu Pro Met Asn Asn
805                 810                 815                 820 aaa aca act aaa aaa gaa tca aaa ata tat gat tat tat tta aag gcc   2611
Lys Thr Thr Lys Lys Glu Ser Lys Ile Tyr Asp Tyr Tyr Leu Lys Ala
```

-continued

```
                      825                 830                 835
tct cca gaa ttt tat cat aac ctt tac ttt aag aat ttt aat gtt ggt    2659
Ser Pro Glu Phe Tyr His Asn Leu Tyr Phe Lys Asn Phe Asn Val Gly
            840                 845                 850 aag aaa aat tta ttc tct gaa aag gaa gat aat gaa aac aac aaa aaa    2707
Lys Lys Asn Leu Phe Ser Glu Lys Glu Asp Asn Glu Asn Asn Lys Lys
            855                 860                 865 tta ggt aac aac tat att ata ttc ggt caa gat acg gca gga tca gga    2755
Leu Gly Asn Asn Tyr Ile Ile Phe Gly Gln Asp Thr Ala Gly Ser Gly
            870                 875                 880 caa agt gga aag gaa agc aat act gca tta gaa tct gca gga act tca    2803
Gln Ser Gly Lys Glu Ser Asn Thr Ala Leu Glu Ser Ala Gly Thr Ser
885                 890                 895                 900 aat gaa gtc tca gaa cgt gtt cat gtt tat cac ata tta aaa cat ata    2851
Asn Glu Val Ser Glu Arg Val His Val Tyr His Ile Leu Lys His Ile
                905                 910                 915 aag gat ggc aaa ata aga atg ggt atg cgt aaa tat ata gat aca caa    2899
Lys Asp Gly Lys Ile Arg Met Gly Met Arg Lys Tyr Ile Asp Thr Gln
            920                 925                 930 gat gta aat aag aaa cat tct tgt aca aga tcc tat gca ttt aat cca    2947
Asp Val Asn Lys Lys His Ser Cys Thr Arg Ser Tyr Ala Phe Asn Pro
            935                 940                 945 gag aat tat gaa aaa tgt gta aat tta tgt aat gtg aac tgg aaa aca    2995
Glu Asn Tyr Glu Lys Cys Val Asn Leu Cys Asn Val Asn Trp Lys Thr
            950                 955                 960 tgc gag gaa aaa aca tca cca gga ctt tgt tta tcc aaa ttg gat aca    3043
Cys Glu Glu Lys Thr Ser Pro Gly Leu Cys Leu Ser Lys Leu Asp Thr
965                 970                 975                 980 aat aac gaa tgt tat ttc tgt tat gta taaataata taacaaaaaa           3090
Asn Asn Glu Cys Tyr Phe Cys Tyr Val
                985 aaaaaaaaaa aaaaaaa                                                  3107
```

<210> SEQ ID NO 2
<211> LENGTH: 989
<212> TYPE: PRT
<213> ORGANISM: Plasmodium falciparum

<400> SEQUENCE: 2

```
Met Lys Ser Tyr Ile Ser Leu Phe Phe Ile Leu Cys Val Ile Phe Asn
 1               5                  10                  15

Lys Asn Val Ile Lys Cys Thr Gly Glu Ser Gln Thr Gly Asn Thr Gly
             20                  25                  30

Gly Gly Gln Ala Gly Asn Thr Val Gly Asp Gln Ala Gly Ser Thr Gly
         35                  40                  45

Gly Ser Pro Gln Gly Ser Thr Gly Ala Ser Gln Pro Gly Ser Ser Glu
     50                  55                  60

Pro Ser Asn Pro Val Ser Ser Gly His Ser Val Ser Thr Val Ser Val
 65                  70                  75                  80

Ser Gln Thr Ser Thr Ser Ser Glu Lys Gln Asp Thr Ile Gln Val Lys
                 85                  90                  95

Ser Ala Leu Leu Lys Asp Tyr Met Gly Leu Lys Val Thr Gly Pro Cys
            100                 105                 110

Asn Glu Asn Phe Ile Met Phe Leu Val Pro His Ile Tyr Ile Asp Val
        115                 120                 125

Asp Thr Glu Asp Thr Asn Ile Glu Leu Arg Thr Thr Leu Lys Glu Thr
    130                 135                 140
```

```
Asn Asn Ala Ile Ser Phe Glu Ser Asn Ser Gly Ser Leu Glu Lys Lys
145                 150                 155                 160

Lys Tyr Val Lys Leu Pro Ser Asn Gly Thr Thr Gly Glu Gln Gly Ser
                165                 170                 175

Ser Thr Gly Thr Val Arg Gly Asp Thr Glu Pro Ile Ser Asp Ser Ser
            180                 185                 190

Ser Ser Ser Ser Ser Ser Ser Ser Ser Ser Ser Ser Ser Ser Ser Ser
        195                 200                 205

Ser Ser Ser Ser Ser Ser Ser Ser Ser Ser Ser Ser Ser Ser Ser Ser
    210                 215                 220

Ser Glu Ser Leu Pro Ala Asn Gly Pro Asp Ser Pro Thr Val Lys Pro
225                 230                 235                 240

Pro Arg Asn Leu Gln Asn Ile Cys Glu Thr Gly Lys Asn Phe Lys Leu
                245                 250                 255

Val Val Tyr Ile Lys Glu Asn Thr Leu Ile Ile Lys Trp Lys Val Tyr
            260                 265                 270

Gly Glu Thr Lys Asp Thr Thr Glu Asn Asn Lys Val Asp Val Arg Lys
            275                 280                 285

Tyr Leu Ile Asn Glu Lys Glu Thr Pro Phe Thr Ser Ile Leu Ile His
            290                 295                 300

Ala Tyr Lys Glu His Asn Gly Thr Asn Leu Ile Glu Ser Lys Asn Tyr
305                 310                 315                 320

Ala Leu Gly Ser Asp Ile Pro Glu Lys Cys Asp Thr Leu Ala Ser Asn
                325                 330                 335

Cys Phe Leu Ser Gly Asn Phe Asn Ile Glu Lys Cys Phe Gln Cys Ala
            340                 345                 350

Leu Leu Val Glu Lys Glu Asn Lys Asn Asp Val Cys Tyr Lys Tyr Leu
            355                 360                 365

Ser Glu Asp Ile Val Ser Asn Phe Lys Glu Ile Lys Ala Glu Thr Glu
370                 375                 380

Asp Asp Glu Glu Asp Asp Tyr Thr Glu Tyr Lys Leu Thr Glu Ser Ile
385                 390                 395                 400

Asp Asn Ile Leu Val Lys Met Phe Lys Thr Asn Glu Asn Asn Asp Lys
                405                 410                 415

Ser Glu Leu Ile Lys Leu Glu Glu Val Asp Asp Ser Leu Lys Leu Glu
            420                 425                 430

Leu Met Asn Tyr Cys Ser Leu Leu Lys Asp Val Asp Thr Thr Gly Thr
            435                 440                 445

Leu Asp Asn Tyr Gly Met Gly Asn Glu Met Asp Ile Phe Asn Asn Leu
            450                 455                 460

Lys Arg Leu Leu Ile Tyr His Ser Glu Glu Asn Ile Asn Thr Leu Lys
465                 470                 475                 480

Asn Lys Phe Arg Asn Ala Ala Val Cys Leu Lys Asn Val Asp Asp Trp
                485                 490                 495

Ile Val Asn Lys Arg Gly Leu Val Leu Pro Glu Leu Asn Tyr Asp Leu
            500                 505                 510

Glu Tyr Phe Asn Glu His Leu Tyr Asn Asp Lys Asn Ser Pro Glu Asp
            515                 520                 525

Lys Asp Asn Lys Gly Lys Gly Val Val His Val Asp Thr Thr Leu Glu
            530                 535                 540

Lys Glu Asp Thr Leu Ser Tyr Asp Asn Ser Asp Asn Met Phe Cys Asn
545                 550                 555                 560

Lys Glu Tyr Cys Asn Arg Leu Lys Asp Glu Asn Asn Cys Ile Ser Asn
```

-continued

```
                565                 570                 575
Leu Gln Val Glu Asp Gln Gly Asn Cys Asp Thr Ser Trp Ile Phe Ala
                580                 585                 590
Ser Lys Tyr His Leu Glu Thr Ile Arg Cys Met Lys Gly Tyr Glu Pro
                595                 600                 605
Thr Lys Ile Ser Ala Leu Tyr Val Ala Asn Cys Tyr Lys Gly Glu His
                610                 615                 620
Lys Asp Arg Cys Asp Glu Gly Ser Ser Pro Met Glu Phe Leu Gln Ile
625                 630                 635                 640
Ile Glu Asp Tyr Gly Phe Leu Pro Ala Glu Ser Asn Tyr Pro Tyr Asn
                645                 650                 655
Tyr Val Lys Val Gly Glu Gln Cys Pro Lys Val Glu Asp His Trp Met
                660                 665                 670
Asn Leu Trp Asp Asn Gly Lys Ile Leu His Asn Lys Asn Glu Pro Asn
                675                 680                 685
Ser Leu Asp Gly Lys Gly Tyr Thr Ala Tyr Glu Ser Glu Arg Phe His
                690                 695                 700
Asp Asn Met Asp Ala Phe Val Lys Ile Ile Lys Thr Glu Val Met Asn
705                 710                 715                 720
Lys Gly Ser Val Ile Ala Tyr Ile Lys Ala Glu Asn Val Met Gly Tyr
                725                 730                 735
Glu Phe Ser Gly Lys Lys Val Gln Asn Leu Cys Gly Asp Asp Thr Ala
                740                 745                 750
Asp His Ala Val Asn Ile Val Gly Tyr Gly Asn Tyr Val Asn Ser Glu
                755                 760                 765
Gly Glu Lys Lys Ser Tyr Trp Ile Val Arg Asn Ser Trp Gly Pro Tyr
                770                 775                 780
Trp Gly Asp Glu Gly Tyr Phe Lys Val Asp Met Tyr Gly Pro Thr His
785                 790                 795                 800
Cys His Phe Asn Phe Ile His Ser Val Val Ile Phe Asn Val Asp Leu
                805                 810                 815
Pro Met Asn Asn Lys Thr Thr Lys Glu Ser Lys Ile Tyr Asp Tyr
                820                 825                 830
Tyr Leu Lys Ala Ser Pro Glu Phe Tyr His Asn Leu Tyr Phe Lys Asn
                835                 840                 845
Phe Asn Val Gly Lys Lys Asn Leu Phe Ser Glu Lys Glu Asp Asn Glu
850                 855                 860
Asn Asn Lys Lys Leu Gly Asn Asn Tyr Ile Ile Phe Gly Gln Asp Thr
865                 870                 875                 880
Ala Gly Ser Gly Gln Ser Gly Lys Glu Ser Asn Thr Ala Leu Glu Ser
                885                 890                 895
Ala Gly Thr Ser Asn Glu Val Ser Glu Arg Val His Val Tyr His Ile
                900                 905                 910
Leu Lys His Ile Lys Asp Gly Lys Ile Arg Met Gly Met Arg Lys Tyr
                915                 920                 925
Ile Asp Thr Gln Asp Val Asn Lys Lys His Ser Cys Thr Arg Ser Tyr
                930                 935                 940
Ala Phe Asn Pro Glu Asn Tyr Glu Lys Cys Val Asn Leu Cys Asn Val
945                 950                 955                 960
Asn Trp Lys Thr Cys Glu Glu Lys Thr Ser Pro Gly Leu Cys Leu Ser
                965                 970                 975
Lys Leu Asp Thr Asn Asn Glu Cys Tyr Phe Cys Tyr Val
                980                 985
```

<210> SEQ ID NO 3
<211> LENGTH: 6124
<212> TYPE: DNA
<213> ORGANISM: Plasmodium falciparum
<220> FEATURE:
<221> NAME/KEY: CDS
<222> LOCATION: (2407)..(2439)
<221> NAME/KEY: CDS
<222> LOCATION: (2598)..(3404)
<221> NAME/KEY: CDS
<222> LOCATION: (3580)..(3720)
<221> NAME/KEY: CDS
<222> LOCATION: (3850)..(5835)

<400> SEQUENCE: 3

```
gaattcttat gtttatggtc aagatacgac accagtagaa aatgaagcac cgggaagtgg      60
agtacaaaaa ccgacagaat tatcatcaac tgaatctcaa acagtatcac caccaaatgg     120
atctcaaaca gaatcgttat taagtggagg ttcacaaata acaaatccaa cgttaacaca     180
aagtacatcc tcatcaagcg gacaacaaga aacagggccc ttatcaacac aaggactatc     240
accagcaact ggagatccaa aaggaaaaga acaagaagca tcaccggcag aaggattatc     300
aggagtatta aatcctacga aggaagttac atctgaagaa aagatccaaa taatacatct     360
attgaaacat ataaagaata gtaaaattag aagaggttta gttaaatata atcatgaatt     420
tgaagtagga gataattctt gttctagatc tacttcaaaa aatgcagaaa tgatgatgaa     480
tgtgtaaaca tttgtgaaaa atattggcct gaatgtagag gaacggctgt tcctggatat     540
tgtttaagta cacatgatga caaaaatgaa tgtgatttct gttatgtata aaattttttat     600
gaaatatata aataatgaat aatcatattg aaaattttat acaagtttgt tttcttattt     660
attattattt ttttattta ttttattta tttttttttt tttttttcatt taaatattta     720
aaatatgaat taaactagtt cttagttaaa actatatatt gtaattcttt tttatttaat     780
attcttattt tgtcttaatt atatatatta tatatatcat tatggaaaaa ataatttcca     840
tttacgaaat ggaaggctat tcatgagatt taaaaaaaaa aaaatatata tatatatata     900
tatatatata tttatgagtt aatgaaacat atatatattt ttttaaatat atttaaaaga     960
gaaagaatga aaaatgtaca tatatgtaat agctatataa ctaatatgtt attttttcatc    1020
tttaaatttt agtcatatat atatatatac atatatatat gaaataatta aaaatgattg    1080
gggtagtatt accaacaata ttttttattaa gaaccttatc taaaaatgta ttaaaatgct    1140
ttataaaaaa aaatatatat aatggtaagt actaggaata aatatttttt ccatcatata    1200
ttttttcaat aataaggaaa taaaaggta tacttcatat aaatcatatt aaggataaat    1260
gtattttatt aaaatattac atgaacataa aaattagtaa gactttatga tggaaaagca    1320
atattaattc atgagcctta atatatttgt taatataaga ataaataaaa aaaataaaat    1380
aaataaaagg tctagtaaaa taagataatg aattttcttt tgtgtaatat tattattgat    1440
atgattttct cgagaccaag aaaaaaaaaa atcaagctta tgttctgata attcaaatgg    1500
atataataaa attaattttt tttaactcct agaaatattt aatgaaataa atacgaccta    1560
ttataatctt gttatgtaaa aacttttttat attggaagaa aaaaaaaatt tattatatat    1620
tttattgtta aattttatta tatatattat aattacaatt tttttttttt tttttttttt    1680
ttttaaccga atgaataata tatttatgag atcacaattt ttaataattt attttttttt    1740
cggtttaaat attttttttgt gtcacgataa ctaatccctt gttattctta aaaaaaaatg    1800
tacacatgta caatatgtat atatatatat atatatatgt attcttacaa tttaatatat    1860
```

-continued

```
tttagaatat taataattaa ttcttagaat aactataatt tgataatccg aaatcttaaa    1920
atgttacaaa aatgagaagt aaaaaactca cttattatat atatatataa tatatattat    1980
atatatattt atatatttaa tgcactttt aatatatggt ttctttttct tttttttt      2040 tttttttatt gagaggtgtg caatatattt tttttgaat aattaaaata aaagaggtc     2100 atattctaga tttattctct tatgagaatg tacaaaaaaa aaaaaaaaaa attaaaataa    2160
aaaaataaaa attaaataat ttaaataata taatatattt atattaaatt tatatatata    2220
tatatataat aaattttta atttaaaatt aaattagatt gtccaaaaaa aaaaataaaa    2280
aaataaatat atatatatat tataaaatac atatattata acataaagaa aaattaaata    2340
aatcaaacat attcaaaaaa attaaagttc ttaaaatatt ataaactta atattcatat    2400 atcaaa atg aag tca tat att tcc ttg ttt ttc ata ttg tgtaagaatg       2449
       Met Lys Ser Tyr Ile Ser Leu Phe Phe Ile Leu
         1               5                  10 aaaaaaaaaa aaaaaaggaa aaggaaaaga aaaaggaaaa gaaaaaggaa aagaaaaaga    2509
aaaacaaata tgtaaaaata taattattat ataataaata atataatatt tttacgcata    2569
cacaaacatt tgtcattatt ttttttta ggt gtt ata ttt aac aaa aat gtt     2621
                                Gly Val Ile Phe Asn Lys Asn Val
                                                15 ata aaa tgt aca gga gaa agt caa aca ggt aat aca gga gga ggt caa    2669
Ile Lys Cys Thr Gly Glu Ser Gln Thr Gly Asn Thr Gly Gly Gly Gln
 20              25                  30                  35 gca ggt aat aca gta gga gat caa gca ggt agt aca gga gga agt cca    2717
Ala Gly Asn Thr Val Gly Asp Gln Ala Gly Ser Thr Gly Gly Ser Pro
         40                  45                  50 caa ggt agt acg gga gca agt caa ccc gga agt tcc gaa cca agc aat    2765
Gln Gly Ser Thr Gly Ala Ser Gln Pro Gly Ser Ser Glu Pro Ser Asn
     55                  60                  65 cct gta agt tcc gga cat tct gta agt act gta tca gta tca caa act    2813
Pro Val Ser Ser Gly His Ser Val Ser Thr Val Ser Val Ser Gln Thr
         70                  75                  80 tca act tct tca gaa aaa cag gat aca att caa gta aaa tca gct tta    2861
Ser Thr Ser Ser Glu Lys Gln Asp Thr Ile Gln Val Lys Ser Ala Leu
 85                  90                  95 tta aaa gat tat atg ggt tta aaa gtt act ggt cca tgt aac gaa aat    2909
Leu Lys Asp Tyr Met Gly Leu Lys Val Thr Gly Pro Cys Asn Glu Asn
100                 105                 110                 115 ttc ata atg ttc tta gtt cct cat ata tat att gat gtt gat aca gaa    2957
Phe Ile Met Phe Leu Val Pro His Ile Tyr Ile Asp Val Asp Thr Glu
             120                 125                 130 gat act aat atc gaa tta aga aca aca ttg aaa gaa aca aat aat gca    3005
Asp Thr Asn Ile Glu Leu Arg Thr Thr Leu Lys Glu Thr Asn Asn Ala
        135                 140                 145 ata tca ttt gaa tca aac agt ggt tca tta gaa aaa aaa aaa tat gta    3053
Ile Ser Phe Glu Ser Asn Ser Gly Ser Leu Glu Lys Lys Lys Tyr Val
            150                 155                 160 aaa cta cca tca aat ggt aca act ggt gaa caa ggt tca agt acg gga    3101
Lys Leu Pro Ser Asn Gly Thr Thr Gly Glu Gln Gly Ser Ser Thr Gly
        165                 170                 175 aca gtt aga gga gat aca gaa cca att tca gat tca agc tca agt tca    3149
Thr Val Arg Gly Asp Thr Glu Pro Ile Ser Asp Ser Ser Ser Ser Ser
180                 185                 190                 195 agt tca agt tct agt tca agt tca agt tca agt tct agt tca agt tca    3197
Ser Ser Ser Ser Ser Ser Ser Ser Ser Ser Ser Ser Ser Ser Ser Ser
                200                 205                 210 agt tca agt tca agt tct agt tca agt tca agt tca agt tca gaa agt    3245
```

```
Ser Ser Ser Ser Ser Ser Ser Ser Ser Ser Ser Ser Ser Glu Ser
            215                 220                 225 ctt cct gct aat gga cct gat tcc cct act gtt aaa ccg cca aga aat      3293
Leu Pro Ala Asn Gly Pro Asp Ser Pro Thr Val Lys Pro Pro Arg Asn
        230                 235                 240 tta caa aat ata tgt gaa act gga aaa aac ttc aag ttg gta gta tat      3341
Leu Gln Asn Ile Cys Glu Thr Gly Lys Asn Phe Lys Leu Val Val Tyr
    245                 250                 255 att aag gag aat aca tta ata att aaa tgg aaa gta tac gga gaa aca      3389
Ile Lys Glu Asn Thr Leu Ile Ile Lys Trp Lys Val Tyr Gly Glu Thr
260                 265                 270                 275 aaa gat act act gaa agtataaaaa ataaccgaat aaaacaataa taataatact      3444
Lys Asp Thr Thr Glu
                280 tttttctttt tttgattgat tattttatat tttcataaga aaatgtcatt atacatacaa    3504 ctactatcaa ttatgtatat tttgttatta tttatattat tattatttat tatttattta   3564 tttatttttt tttta gat aac aaa gtt gat gta aga aag tat ttg ata aat    3615
                Asp Asn Lys Val Asp Val Arg Lys Tyr Leu Ile Asn
                                285                 290 gaa aag gaa acc cca ttt act agt ata cta ata cat gcg tat aaa gaa      3663
Glu Lys Glu Thr Pro Phe Thr Ser Ile Leu Ile His Ala Tyr Lys Glu
        295                 300                 305 cat aat gga aca aac tta ata gaa agt aaa aac tac gca tta gga tca      3711
His Asn Gly Thr Asn Leu Ile Glu Ser Lys Asn Tyr Ala Leu Gly Ser
    310                 315                 320 gac att cca ggtaaataac aataagagg aatatacaaa tgtatgaata               3760
Asp Ile Pro
325 tatatgcata atcaaaatgt aatatatata tatatatata tatatatata tatatacata    3820 ttatatattt ttttaattttt tttgttttta gaa aaa tgt gat acc tta gct tcc    3873
                                Glu Lys Cys Asp Thr Leu Ala Ser
                                            330                 335 aat tgc ttt tta agt ggt aat ttt aac att gaa aaa tgc ttt caa tgt      3921
Asn Cys Phe Leu Ser Gly Asn Phe Asn Ile Glu Lys Cys Phe Gln Cys
        340                 345                 350 gct ctt tta gta gaa aaa gaa aat aaa aat gac gta tgt tac aaa tac      3969
Ala Leu Leu Val Glu Lys Glu Asn Lys Asn Asp Val Cys Tyr Lys Tyr
    355                 360                 365 cta tct gaa gat att gta agt aac ttc aaa gaa ata aaa gct gag aca      4017
Leu Ser Glu Asp Ile Val Ser Asn Phe Lys Glu Ile Lys Ala Glu Thr
370                 375                 380 gaa gat gat gat gaa gat gat tat act gaa tat aaa tta aca gaa tct      4065
Glu Asp Asp Asp Glu Asp Asp Tyr Thr Glu Tyr Lys Leu Thr Glu Ser
        385                 390                 395 att gat aat ata tta gta aaa atg ttt aaa aca aat gaa aat aat gat      4113
Ile Asp Asn Ile Leu Val Lys Met Phe Lys Thr Asn Glu Asn Asn Asp
400                 405                 410                 415 aaa tca gaa tta ata aaa tta gaa gaa gta gat gat agt ttg aaa tta      4161
Lys Ser Glu Leu Ile Lys Leu Glu Glu Val Asp Asp Ser Leu Lys Leu
            420                 425                 430 gaa tta atg aat tac tgt agt tta ctt aaa gac gta gat aca aca ggt      4209
Glu Leu Met Asn Tyr Cys Ser Leu Leu Lys Asp Val Asp Thr Thr Gly
        435                 440                 445 acc tta gat aat tat ggg atg gga aat gaa atg gat ata ttt aat aac      4257
Thr Leu Asp Asn Tyr Gly Met Gly Asn Glu Met Asp Ile Phe Asn Asn
    450                 455                 460 tta aag aga tta tta att tat cat tca gaa gaa aat att aat act tta      4305
Leu Lys Arg Leu Leu Ile Tyr His Ser Glu Glu Asn Ile Asn Thr Leu
```

```
            465                 470                 475
aaa aat aaa ttc cgt aat gca gct gta tgt ctt aaa aat gtt gat gat     4353
Lys Asn Lys Phe Arg Asn Ala Ala Val Cys Leu Lys Asn Val Asp Asp
480                 485                 490                 495 tgg att gta aat aag aga ggt tta gta tta cct gaa tta aat tat gat     4401
Trp Ile Val Asn Lys Arg Gly Leu Val Leu Pro Glu Leu Asn Tyr Asp
                500                 505                 510 tta gaa tat ttc aat gaa cat tta tat aat gat aaa aat tct cca gaa     4449
Leu Glu Tyr Phe Asn Glu His Leu Tyr Asn Asp Lys Asn Ser Pro Glu
                515                 520                 525 gat aaa gat aat aaa gga aaa ggt gtc gta cat gtt gat aca act tta     4497
Asp Lys Asp Asn Lys Gly Lys Gly Val Val His Val Asp Thr Thr Leu
                530                 535                 540 gaa aaa gaa gat act tta tca tat gat aac tca gat aat atg ttt tgt     4545
Glu Lys Glu Asp Thr Leu Ser Tyr Asp Asn Ser Asp Asn Met Phe Cys
545                 550                 555 aat aaa gaa tat tgt aac aga tta aaa gat gaa aat aat tgt ata tct     4593
Asn Lys Glu Tyr Cys Asn Arg Leu Lys Asp Glu Asn Asn Cys Ile Ser
560                 565                 570                 575 aat ctt caa gtt gaa gat caa ggt aat tgt gat act tca tgg att ttt     4641
Asn Leu Gln Val Glu Asp Gln Gly Asn Cys Asp Thr Ser Trp Ile Phe
                580                 585                 590 gct tca aaa tat cat tta gaa act att aga tgt atg aaa gga tat gaa     4689
Ala Ser Lys Tyr His Leu Glu Thr Ile Arg Cys Met Lys Gly Tyr Glu
                595                 600                 605 cct acc aaa att tct gct ctt tat gta gct aat tgt tat aaa ggt gaa     4737
Pro Thr Lys Ile Ser Ala Leu Tyr Val Ala Asn Cys Tyr Lys Gly Glu
            610                 615                 620 cat aaa gat aga tgt gat gaa ggt tct agt cca atg gaa ttc tta caa     4785
His Lys Asp Arg Cys Asp Glu Gly Ser Ser Pro Met Glu Phe Leu Gln
625                 630                 635 att att gaa gat tat gga ttc tta cca gca gaa tca aat tat cca tat     4833
Ile Ile Glu Asp Tyr Gly Phe Leu Pro Ala Glu Ser Asn Tyr Pro Tyr
640                 645                 650                 655 aac tat gtg aaa gtt gga gaa caa tgt cca aag gta gaa gat cac tgg     4881
Asn Tyr Val Lys Val Gly Glu Gln Cys Pro Lys Val Glu Asp His Trp
                660                 665                 670 atg aat cta tgg gat aat gga aaa atc tta cat aac aaa aat gaa cct     4929
Met Asn Leu Trp Asp Asn Gly Lys Ile Leu His Asn Lys Asn Glu Pro
                675                 680                 685 aat agt tta gat ggt aag gga tat act gca tat gaa agt gaa aga ttt     4977
Asn Ser Leu Asp Gly Lys Gly Tyr Thr Ala Tyr Glu Ser Glu Arg Phe
                690                 695                 700 cat gat aat atg gat gca ttt gtt aaa att att aaa act gaa gta atg     5025
His Asp Asn Met Asp Ala Phe Val Lys Ile Ile Lys Thr Glu Val Met
705                 710                 715 aat aaa ggt tca gtt att gca tat att aaa gct gaa aat gtt atg gga     5073
Asn Lys Gly Ser Val Ile Ala Tyr Ile Lys Ala Glu Asn Val Met Gly
720                 725                 730                 735 tat gaa ttt agt gga aag aaa gta cag aac tta tgt ggt gat gat aca     5121
Tyr Glu Phe Ser Gly Lys Lys Val Gln Asn Leu Cys Gly Asp Asp Thr
                740                 745                 750 gct gat cat gca gtt aat att gtt ggt tat ggt aat tat gtg aat agc     5169
Ala Asp His Ala Val Asn Ile Val Gly Tyr Gly Asn Tyr Val Asn Ser
                755                 760                 765 gaa gga gaa aaa aaa tcc tat tgg att gta aga aac agt tgg ggt cca     5217
Glu Gly Glu Lys Lys Ser Tyr Trp Ile Val Arg Asn Ser Trp Gly Pro
                770                 775                 780 tat tgg gga gat gaa ggt tat ttt aaa gta gat atg tat gga cca act     5265
```

```
Tyr Trp Gly Asp Glu Gly Tyr Phe Lys Val Asp Met Tyr Gly Pro Thr
    785                 790                 795 cat tgt cat ttt aac ttt att cac agt gtt gtt ata ttc aat gtt gat    5313
His Cys His Phe Asn Phe Ile His Ser Val Val Ile Phe Asn Val Asp
800                 805                 810                 815 tta cct atg aat aat aaa aca act aaa aaa gaa tca aaa ata tat gat    5361
Leu Pro Met Asn Asn Lys Thr Thr Lys Lys Glu Ser Lys Ile Tyr Asp
                820                 825                 830 tat tat tta aag gcc tct cca gaa ttt tat cat aac ctt tac ttt aag    5409
Tyr Tyr Leu Lys Ala Ser Pro Glu Phe Tyr His Asn Leu Tyr Phe Lys
            835                 840                 845 aat ttt aat gtt ggt aag aaa aat tta ttc tct gaa aag gaa gat aat    5457
Asn Phe Asn Val Gly Lys Lys Asn Leu Phe Ser Glu Lys Glu Asp Asn
        850                 855                 860 gaa aac aac aaa aaa tta ggt aac aac tat att ata ttc ggt caa gat    5505
Glu Asn Asn Lys Lys Leu Gly Asn Asn Tyr Ile Ile Phe Gly Gln Asp
865                 870                 875 acg gca gga tca gga caa agt gga aag gaa agc aat act gca tta gaa    5553
Thr Ala Gly Ser Gly Gln Ser Gly Lys Glu Ser Asn Thr Ala Leu Glu
880                 885                 890                 895 tct gca gga act tca aat gaa gtc tca gaa cgt gtt cat gtt tat cac    5601
Ser Ala Gly Thr Ser Asn Glu Val Ser Glu Arg Val His Val Tyr His
                900                 905                 910 ata tta aaa cat ata aag gat ggc aaa ata aga atg ggt atg cgt aaa    5649
Ile Leu Lys His Ile Lys Asp Gly Lys Ile Arg Met Gly Met Arg Lys
            915                 920                 925 tat ata gat aca caa gat gta aat aag aaa cat tct tgt aca aga tcc    5697
Tyr Ile Asp Thr Gln Asp Val Asn Lys Lys His Ser Cys Thr Arg Ser
        930                 935                 940 tat gca ttt aat cca gag aat tat gaa aaa tgt gta aat tta tgt aat    5745
Tyr Ala Phe Asn Pro Glu Asn Tyr Glu Lys Cys Val Asn Leu Cys Asn
945                 950                 955 gtg aac tgg aaa aca tgc gag gaa aaa aca tca cca gga ctt tgt tta    5793
Val Asn Trp Lys Thr Cys Glu Glu Lys Thr Ser Pro Gly Leu Cys Leu
960                 965                 970                 975 tcc aaa ttg gat aca aat aac gaa tgt tat ttc tgt tat gta            5835
Ser Lys Leu Asp Thr Asn Asn Glu Cys Tyr Phe Cys Tyr Val
                980                 985 taaaataata taacaaaaaa aaaaaaaaaa aatattttt tttatgtatc ctttaattt    5895 taaatagggc ataactctcc attattcatt ttattaaggt agtataatat ctttaattta    5955
tcatgtacct ctataaatat atataaaatt atattattat tatttttttt tttaagaatt    6015
atttttattc atgtaaatat aattcttttt tttttttttt tttttttttt ttaaaaaaaa    6075
tacacgatag ttgtacatta aatgtataca attatattaa ctggaattc                6124

<210> SEQ ID NO 4
<211> LENGTH: 989
<212> TYPE: PRT
<213> ORGANISM: Plasmodium falciparum

<400> SEQUENCE: 4

Met Lys Ser Tyr Ile Ser Leu Phe Phe Ile Leu Gly Val Ile Phe Asn
1               5                   10                  15

Lys Asn Val Ile Lys Cys Thr Gly Glu Ser Gln Thr Gly Asn Thr Gly
            20                  25                  30

Gly Gly Gln Ala Gly Asn Thr Val Gly Asp Gln Ala Gly Ser Thr Gly
        35                  40                  45

Gly Ser Pro Gln Gly Ser Thr Gly Ala Ser Gln Pro Gly Ser Ser Glu
```

```
                50              55              60
Pro Ser Asn Pro Val Ser Ser Gly His Ser Val Ser Thr Val Ser Val
65                  70                  75                  80

Ser Gln Thr Ser Thr Ser Ser Glu Lys Gln Asp Thr Ile Gln Val Lys
                85                  90                  95

Ser Ala Leu Leu Lys Asp Tyr Met Gly Leu Lys Val Thr Gly Pro Cys
            100                 105                 110

Asn Glu Asn Phe Ile Met Phe Leu Val Pro His Ile Tyr Ile Asp Val
            115                 120                 125

Asp Thr Glu Asp Thr Asn Ile Glu Leu Arg Thr Thr Leu Lys Glu Thr
        130                 135                 140

Asn Asn Ala Ile Ser Phe Glu Ser Asn Ser Gly Ser Leu Glu Lys Lys
145                 150                 155                 160

Lys Tyr Val Lys Leu Pro Ser Asn Gly Thr Thr Gly Glu Gln Gly Ser
                165                 170                 175

Ser Thr Gly Thr Val Arg Gly Asp Thr Glu Pro Ile Ser Asp Ser Ser
            180                 185                 190

Ser Ser Ser Ser Ser Ser Ser Ser Ser Ser Ser Ser Ser Ser Ser Ser
        195                 200                 205

Ser Ser Ser Ser Ser Ser Ser Ser Ser Ser Ser Ser Ser Ser Ser Ser
210                 215                 220

Ser Glu Ser Leu Pro Ala Asn Gly Pro Asp Ser Pro Thr Val Lys Pro
225                 230                 235                 240

Pro Arg Asn Leu Gln Asn Ile Cys Glu Thr Gly Lys Asn Phe Lys Leu
                245                 250                 255

Val Val Tyr Ile Lys Glu Asn Thr Leu Ile Ile Lys Trp Lys Val Tyr
            260                 265                 270

Gly Glu Thr Lys Asp Thr Thr Glu Asp Asn Lys Val Asp Val Arg Lys
        275                 280                 285

Tyr Leu Ile Asn Glu Lys Glu Thr Pro Phe Thr Ser Ile Leu Ile His
        290                 295                 300

Ala Tyr Lys Glu His Asn Gly Thr Asn Leu Ile Glu Ser Lys Asn Tyr
305                 310                 315                 320

Ala Leu Gly Ser Asp Ile Pro Glu Lys Cys Asp Thr Leu Ala Ser Asn
                325                 330                 335

Cys Phe Leu Ser Gly Asn Phe Asn Ile Glu Lys Cys Phe Gln Cys Ala
            340                 345                 350

Leu Leu Val Glu Lys Glu Asn Lys Asn Asp Val Cys Tyr Lys Tyr Leu
        355                 360                 365

Ser Glu Asp Ile Val Ser Asn Phe Lys Glu Ile Lys Ala Glu Thr Glu
        370                 375                 380

Asp Asp Asp Glu Asp Asp Tyr Thr Glu Tyr Lys Leu Thr Glu Ser Ile
385                 390                 395                 400

Asp Asn Ile Leu Val Lys Met Phe Lys Thr Asn Glu Asn Asn Asp Lys
                405                 410                 415

Ser Glu Leu Ile Lys Leu Glu Val Asp Asp Ser Leu Lys Leu Glu
            420                 425                 430

Leu Met Asn Tyr Cys Ser Leu Leu Lys Asp Val Asp Thr Thr Gly Thr
        435                 440                 445

Leu Asp Asn Tyr Gly Met Gly Asn Glu Met Asp Ile Phe Asn Asn Leu
        450                 455                 460

Lys Arg Leu Leu Ile Tyr His Ser Glu Glu Asn Ile Asn Thr Leu Lys
465                 470                 475                 480
```

-continued

```
Asn Lys Phe Arg Asn Ala Ala Val Cys Leu Lys Asn Val Asp Asp Trp
            485                 490                 495
Ile Val Asn Lys Arg Gly Leu Val Leu Pro Glu Leu Asn Tyr Asp Leu
            500                 505                 510
Glu Tyr Phe Asn Glu His Leu Tyr Asn Asp Lys Asn Ser Pro Glu Asp
            515                 520                 525
Lys Asp Asn Lys Gly Lys Gly Val His Val Asp Thr Thr Leu Glu
            530             535                 540
Lys Glu Asp Thr Leu Ser Tyr Asp Asn Ser Asp Asn Met Phe Cys Asn
545             550                 555                 560
Lys Glu Tyr Cys Asn Arg Leu Lys Asp Glu Asn Asn Cys Ile Ser Asn
                565                 570                 575
Leu Gln Val Glu Asp Gln Gly Asn Cys Asp Thr Ser Trp Ile Phe Ala
                580                 585                 590
Ser Lys Tyr His Leu Glu Thr Ile Arg Cys Met Lys Gly Tyr Glu Pro
            595                 600                 605
Thr Lys Ile Ser Ala Leu Tyr Val Ala Asn Cys Tyr Lys Gly Glu His
            610                 615                 620
Lys Asp Arg Cys Asp Glu Gly Ser Ser Pro Met Glu Phe Leu Gln Ile
625             630                 635                 640
Ile Glu Asp Tyr Gly Phe Leu Pro Ala Glu Ser Asn Tyr Pro Tyr Asn
                645                 650                 655
Tyr Val Lys Val Gly Glu Gln Cys Pro Lys Val Glu Asp His Trp Met
                660                 665                 670
Asn Leu Trp Asp Asn Gly Lys Ile Leu His Asn Lys Asn Glu Pro Asn
            675                 680                 685
Ser Leu Asp Gly Lys Gly Tyr Thr Ala Tyr Glu Ser Glu Arg Phe His
            690                 695                 700
Asp Asn Met Asp Ala Phe Val Lys Ile Ile Lys Thr Glu Val Met Asn
705             710                 715                 720
Lys Gly Ser Val Ile Ala Tyr Ile Lys Ala Glu Asn Val Met Gly Tyr
                725                 730                 735
Glu Phe Ser Gly Lys Lys Val Gln Asn Leu Cys Gly Asp Asp Thr Ala
            740                 745                 750
Asp His Ala Val Asn Ile Val Gly Tyr Gly Asn Tyr Val Asn Ser Glu
            755                 760                 765
Gly Glu Lys Lys Ser Tyr Trp Ile Val Arg Asn Ser Trp Gly Pro Tyr
            770                 775                 780
Trp Gly Asp Glu Gly Tyr Phe Lys Val Asp Met Tyr Gly Pro Thr His
785             790                 795                 800
Cys His Phe Asn Phe Ile His Ser Val Val Ile Phe Asn Val Asp Leu
                805                 810                 815
Pro Met Asn Asn Lys Thr Thr Lys Lys Glu Ser Lys Ile Tyr Asp Tyr
                820                 825                 830
Tyr Leu Lys Ala Ser Pro Glu Phe Tyr His Asn Leu Tyr Phe Lys Asn
            835                 840                 845
Phe Asn Val Gly Lys Lys Asn Leu Phe Ser Glu Lys Glu Asp Asn Glu
850                 855                 860
Asn Asn Lys Lys Leu Gly Asn Tyr Ile Ile Phe Gly Gln Asp Thr
865                 870                 875                 880
Ala Gly Ser Gly Gln Ser Gly Lys Glu Ser Asn Thr Ala Leu Glu Ser
                885                 890                 895
```

-continued

```
Ala Gly Thr Ser Asn Glu Val Ser Glu Arg Val His Val Tyr His Ile
            900                 905                 910
Leu Lys His Ile Lys Asp Gly Lys Ile Arg Met Gly Met Arg Lys Tyr
            915                 920                 925
Ile Asp Thr Gln Asp Val Asn Lys Lys His Ser Cys Thr Arg Ser Tyr
            930                 935                 940
Ala Phe Asn Pro Glu Asn Tyr Glu Lys Cys Val Asn Leu Cys Asn Val
945                 950                 955                 960
Asn Trp Lys Thr Cys Glu Glu Lys Thr Ser Pro Gly Leu Cys Leu Ser
            965                 970                 975
Lys Leu Asp Thr Asn Asn Glu Cys Tyr Phe Cys Tyr Val
            980                 985
```

<210> SEQ ID NO 5
<211> LENGTH: 159
<212> TYPE: DNA
<213> ORGANISM: Plasmodium falciparum

<400> SEQUENCE: 5

```
aacaaggttc aagtacggga acagttagag gagatacaga accaatttca gattcaagct      60
caagttcaag ttcaagttct agttcaagtt caagttcaag ttctagttca agttcaagtt     120
caagttcaag ttctagttca agttcaagtt caagttcag                             159
```

<210> SEQ ID NO 6
<211> LENGTH: 120
<212> TYPE: DNA
<213> ORGANISM: Plasmodium falciparum

<400> SEQUENCE: 6

```
aacaaagttc tagttcaagt tcaagttcta gttcaaattc tagttcaagt tcaagttcaa      60
gttcaagttc tagttcaagt tcaagttcaa gttctagttc aagttcaagt tcaagttcag     120
```

<210> SEQ ID NO 7
<211> LENGTH: 16
<212> TYPE: PRT
<213> ORGANISM: Plasmodium falciparum

<400> SEQUENCE: 7

```
Met Lys Ser Tyr Ile Ser Leu Phe Phe Ile Leu Cys Val Ile Phe Asn
  1               5                  10                  15
```

<210> SEQ ID NO 8
<211> LENGTH: 30
<212> TYPE: DNA
<213> ORGANISM: Plasmodium falciparum

<400> SEQUENCE: 8

```
ctgtatctcc tctaactgtt cccgtacttg                                        30
```

<210> SEQ ID NO 9
<211> LENGTH: 30
<212> TYPE: DNA
<213> ORGANISM: Plasmodium falciparum

<400> SEQUENCE: 9

```
ctagaacttg aacttgaact agaactttgt                                        30
```

<210> SEQ ID NO 10
<211> LENGTH: 24
<212> TYPE: DNA

<213> ORGANISM: Plasmodium falciparum

<400> SEQUENCE: 10

```
gtaatacagg aggaggtcaa gcag                                           24
```

<210> SEQ ID NO 11
<211> LENGTH: 39
<212> TYPE: DNA
<213> ORGANISM: Plasmodium falciparum

<400> SEQUENCE: 11

```
gggaacagtt agaggagata cagaaccaat ttcagattc                           39
```

<210> SEQ ID NO 12
<211> LENGTH: 810
<212> TYPE: DNA
<213> ORGANISM: Plasmodium falciparum
<220> FEATURE:
<221> NAME/KEY: CDS
<222> LOCATION: (43)..(723)
<223> OTHER INFORMATION: All occurrences of Xaa indicate any amino acid

<400> SEQUENCE: 12

```
tctagaaata attttgttta actttaagaa ggagatatac at atg gag cag gta        54
                                               Met Glu Gln Val
                                                 1 tgt gac gtt ttc gac atc tac gcg att tgc gcg tgc tgc aag gtg gag      102
Cys Asp Val Phe Asp Ile Tyr Ala Ile Cys Ala Cys Cys Lys Val Glu
  5                  10                  15                  20 tca aag aac gag gga aaa aaa aat gag gtg ttc aac aac tac aca ttt      150
Ser Lys Asn Glu Gly Lys Lys Asn Glu Val Phe Asn Asn Tyr Thr Phe
             25                  30                  35 cga ggc ctt ggc aac aaa ggt gtg ttg ccg tgg aaa tgc aac tca ttg      198
Arg Gly Leu Gly Asn Lys Gly Val Leu Pro Trp Lys Cys Asn Ser Leu
         40                  45                  50 gat atg aag tac ttt tgt gca gtg acc acg tat gtg aat gaa agt aaa      246
Asp Met Lys Tyr Phe Cys Ala Val Thr Thr Tyr Val Asn Glu Ser Lys
     55                  60                  65 tac gaa aaa ctt aag tat aag cgg tkt aag tat ctc aac aaa gaa aca      294
Tyr Glu Lys Leu Lys Tyr Lys Arg Xaa Lys Tyr Leu Asn Lys Glu Thr
 70                  75                  80 gtt gac aac gtc aat gat atg cct aac tct aaa aaa ctg cag aac gtc      342
Val Asp Asn Val Asn Asp Met Pro Asn Ser Lys Lys Leu Gln Asn Val
 85                  90                  95                 100 gtt gtw atg ggc cgy acg asc tgg gaa tca atc ccg aaa aaa ttc aag      390
Val Xaa Met Gly Xaa Thr Xaa Trp Glu Ser Ile Pro Lys Lys Phe Lys
             105                 110                 115 ccg ttg tcg aat cgc atc aat gtg atc ctc tct aga acg ttg aag aaa      438
Pro Leu Ser Asn Arg Ile Asn Val Ile Leu Ser Arg Thr Leu Lys Lys
         120                 125                 130 gag gac ttt gac gaa gat gta tat att att aat aag gtk gaa gat ttr      486
Glu Asp Phe Asp Glu Asp Val Tyr Ile Ile Asn Lys Xaa Glu Asp Xaa
     135                 140                 145 atc gtg ctc cta ggt aag ttg aat tac tac aaa tgc ttt att att ggc      534
Ile Val Leu Leu Gly Lys Leu Asn Tyr Tyr Lys Cys Phe Ile Ile Gly
150                 155                 160 ggc agc gtt gtt tat cag gaa ttt ttg gag aag aag ctg atc aag aag      582
Gly Ser Val Val Tyr Gln Glu Phe Leu Glu Lys Lys Leu Ile Lys Lys
165                 170                 175                 180 atc tac ttt acg cgt atc aat agc acc tat gaa tgt gac gtg ttc ttc      630
Ile Tyr Phe Thr Arg Ile Asn Ser Thr Tyr Glu Cys Asp Val Phe Phe
             185                 190                 195
```

-continued

```
ccg gaa att aat gag aac gag tac cag ata atc tcc gtc agc gac gtc    678
Pro Glu Ile Asn Glu Asn Glu Tyr Gln Ile Ile Ser Val Ser Asp Val
        200                 205                 210 tac acc tct aac aac act act ttg gac ttt att att tat aag aag        723
Tyr Thr Ser Asn Asn Thr Thr Leu Asp Phe Ile Ile Tyr Lys Lys
    215                 220                 225 taaggatccg gctgctaaca aagccgaaag gaagctgagt tggctgctgc caccgctgag  783
caataactag cataacccct tggggcc                                      810

<210> SEQ ID NO 13
<211> LENGTH: 227
<212> TYPE: PRT
<213> ORGANISM: Plasmodium falciparum
<220> FEATURE:
<223> OTHER INFORMATION: All occurrences of Xaa indicate any amino acid

<400> SEQUENCE: 13

Glu Gln Val Cys Asp Val Phe Asp Ile Tyr Ala Ile Cys Ala Cys
                5                  10                  15

Lys Val Glu Ser Lys Asn Glu Gly Lys Lys Asn Glu Val Phe Asn
         20                  25                  30

Tyr Thr Phe Arg Gly Leu Gly Asn Lys Gly Val Leu Pro Trp Lys
     35                  40                  45

Asn Ser Leu Asp Met Lys Tyr Phe Cys Ala Val Thr Thr Tyr Val
50                  55                  60

Glu Ser Lys Tyr Glu Lys Leu Lys Tyr Lys Arg Xaa Lys Tyr Leu
                 70                  75                  80

Lys Glu Thr Val Asp Asn Val Asn Asp Met Pro Asn Ser Lys Lys
             85                  90                  95

Gln Asn Val Val Xaa Met Gly Xaa Thr Xaa Trp Glu Ser Ile Pro
         100                 105                 110

Lys Phe Lys Pro Leu Ser Asn Arg Ile Asn Val Ile Leu Ser Arg
     115                 120                 125

Leu Lys Lys Glu Asp Phe Asp Glu Asp Val Tyr Ile Ile Asn Lys
130                 135                 140

Glu Asp Xaa Ile Val Leu Leu Gly Lys Leu Asn Tyr Tyr Lys Cys
                 150                 155                 160

Ile Ile Gly Gly Ser Val Val Tyr Gln Glu Phe Leu Glu Lys Lys
             165                 170                 175

Ile Lys Lys Ile Tyr Phe Thr Arg Ile Asn Ser Thr Tyr Glu Cys
         180                 185                 190

Val Phe Phe Pro Glu Ile Asn Glu Asn Glu Tyr Gln Ile Ile Ser
     195                 200                 205

Ser Asp Val Tyr Thr Ser Asn Asn Thr Thr Leu Asp Phe Ile Ile
210                 215                 220

Lys Lys

<210> SEQ ID NO 14
<211> LENGTH: 1104
<212> TYPE: DNA
<213> ORGANISM: Plasmodium falciparum
<220> FEATURE:
<221> NAME/KEY: CDS
<222> LOCATION: (1)..(1101)

<400> SEQUENCE: 14
```

```
atg aaa aac gtg atc aaa tgt acc ggt gaa agc cag acc ggt aat acc      48
Met Lys Asn Val Ile Lys Cys Thr Gly Glu Ser Gln Thr Gly Asn Thr
 1               5                  10                  15 ggc ggt ggt cag gca ggc aac acg gtt ggc gac cag gcg ggt tct acc      96
Gly Gly Gly Gln Ala Gly Asn Thr Val Gly Asp Gln Ala Gly Ser Thr
                20                  25                  30 ggc ggc tct ccg cag ggt agc aca ggc gcc agt caa ccc ggc tct agc     144
Gly Gly Ser Pro Gln Gly Ser Thr Gly Ala Ser Gln Pro Gly Ser Ser
            35                  40                  45 gaa ccg tct aac cca gtg tct tct ggc cat tct gtt agt acc gtt agc     192
Glu Pro Ser Asn Pro Val Ser Ser Gly His Ser Val Ser Thr Val Ser
    50                  55                  60 gtt agc cag acc agc acc tct tct gaa aaa caa gat acc att cag gtg     240
Val Ser Gln Thr Ser Thr Ser Ser Glu Lys Gln Asp Thr Ile Gln Val
 65                 70                  75                  80 aaa tct gcg ctg ctg aaa gat tat atg ggt tta aaa gtt acg ggc ccg     288
Lys Ser Ala Leu Leu Lys Asp Tyr Met Gly Leu Lys Val Thr Gly Pro
                85                  90                  95 tgt aac gaa aat ttc atc atg ttc ctg gtt ccg cat att tat att gat     336
Cys Asn Glu Asn Phe Ile Met Phe Leu Val Pro His Ile Tyr Ile Asp
            100                 105                 110 gtg gat acc gaa gat acc aat ata gag ctc cgt acc acc ctg aaa gaa     384
Val Asp Thr Glu Asp Thr Asn Ile Glu Leu Arg Thr Thr Leu Lys Glu
    115                 120                 125 acc aac aac gcg atc tca ttt gaa tca aac agt ggt tca ctg gaa aaa     432
Thr Asn Asn Ala Ile Ser Phe Glu Ser Asn Ser Gly Ser Leu Glu Lys
130                 135                 140 aaa aaa tat gtg aag ctt ccg tca aac ggc acc acc ggt gaa cag ggt     480
Lys Lys Tyr Val Lys Leu Pro Ser Asn Gly Thr Thr Gly Glu Gln Gly
145                 150                 155                 160 tca agt aca ggc acc gtt cgc ggc gat acc gaa ccg att tca cac tcg     528
Ser Ser Thr Gly Thr Val Arg Gly Asp Thr Glu Pro Ile Ser His Ser
                165                 170                 175 agt agc tct tcg tcc agt tca agc tcc tct agc tcg tca tct agc tcg     576
Ser Ser Ser Ser Ser Ser Ser Ser Ser Ser Ser Ser Ser Ser Ser Ser
            180                 185                 190 tct agc agt tca tcc agc agt tct agc tcg tcc tct agt tcc agc tca     624
Ser Ser Ser Ser Ser Ser Ser Ser Ser Ser Ser Ser Ser Ser Ser Ser
    195                 200                 205 tcg agc gaa agt ctt ccg gcg aat ggc ccg gat tcc ccg acc gtt aaa     672
Ser Ser Glu Ser Leu Pro Ala Asn Gly Pro Asp Ser Pro Thr Val Lys
210                 215                 220 ccc ccg cgt aac ctg cag aac atc tgt gaa acc ggc aaa aac ttc aaa     720
Pro Pro Arg Asn Leu Gln Asn Ile Cys Glu Thr Gly Lys Asn Phe Lys
225                 230                 235                 240 ctg gtg gtg tat att aag gag aat aca tta atc att aaa tgg aaa gtg     768
Leu Val Val Tyr Ile Lys Glu Asn Thr Leu Ile Ile Lys Trp Lys Val
                245                 250                 255 tac ggc gaa acc aaa gat acc acc gaa aat aac aaa gtg gac gta cgc     816
Tyr Gly Glu Thr Lys Asp Thr Thr Glu Asn Asn Lys Val Asp Val Arg
            260                 265                 270 aag tat ctg att aac gaa aag gaa acc ccg ttt act agt att cta atc     864
Lys Tyr Leu Ile Asn Glu Lys Glu Thr Pro Phe Thr Ser Ile Leu Ile
    275                 280                 285 cat gca tat aaa gaa cat aat ggc acc aac ctg atc gaa act aaa aac     912
His Ala Tyr Lys Glu His Asn Gly Thr Asn Leu Ile Glu Thr Lys Asn
290                 295                 300 tac gcg ctg ggc tca gac att ccg gaa aaa tgt gat acc ctg gcg tcc     960
Tyr Ala Leu Gly Ser Asp Ile Pro Glu Lys Cys Asp Thr Leu Ala Ser
305                 310                 315                 320
```

```
aat tgc ttt ctg agt ggt aac ttt aac att gaa aaa tgc ttt cag tgc    1008
Asn Cys Phe Leu Ser Gly Asn Phe Asn Ile Glu Lys Cys Phe Gln Cys
            325                 330                 335 gcg ctg ctg gtg gaa aaa gaa aat aaa aac gac gtg tgt tac aaa tac    1056
Ala Leu Leu Val Glu Lys Glu Asn Lys Asn Asp Val Cys Tyr Lys Tyr
340                 345                 350 cta agc gaa gat att gtg tct aat ttc aag gag atc aaa gcg gag taa    1104
Leu Ser Glu Asp Ile Val Ser Asn Phe Lys Glu Ile Lys Ala Glu
            355                 360                 365

<210> SEQ ID NO 15
<211> LENGTH: 367
<212> TYPE: PRT
<213> ORGANISM: Plasmodium falciparum

<400> SEQUENCE: 15
```

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
        35                  40                  45

Glu Pro Ser Asn Pro Val Ser Ser Gly His Ser Val Ser Thr Val Ser
50                  55                  60

Val Ser Gln Thr Ser Thr Ser Ser Glu Lys Gln Asp Thr Ile Gln Val
65                  70                  75                  80

Lys Ser Ala Leu Leu Lys Asp Tyr Met Gly Leu Lys Val Thr Gly Pro
                85                  90                  95

Cys Asn Glu Asn Phe Ile Met Phe Leu Val Pro His Ile Tyr Ile Asp
            100                 105                 110

Val Asp Thr Glu Asp Thr Asn Ile Glu Leu Arg Thr Thr Leu Lys Glu
        115                 120                 125

Thr Asn Asn Ala Ile Ser Phe Glu Ser Asn Ser Gly Ser Leu Glu Lys
130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser His Ser
                165                 170                 175

Ser Ser Ser Ser Ser Ser Ser Ser Ser Ser Ser Ser Ser Ser Ser Ser
            180                 185                 190

Ser Ser Ser Ser Ser Ser Ser Ser Ser Ser Ser Ser Ser Ser Ser Ser
        195                 200                 205

Ser Ser Glu Ser Leu Pro Ala Asn Gly Pro Asp Ser Pro Thr Val Lys
210                 215                 220

Pro Pro Arg Asn Leu Gln Asn Ile Cys Glu Thr Gly Lys Asn Phe Lys
225                 230                 235                 240

Leu Val Val Tyr Ile Lys Glu Asn Thr Leu Ile Ile Lys Trp Lys Val
                245                 250                 255

Tyr Gly Glu Thr Lys Asp Thr Thr Glu Asn Asn Lys Val Asp Val Arg
            260                 265                 270

Lys Tyr Leu Ile Asn Glu Lys Thr Pro Phe Thr Ser Ile Leu Ile
        275                 280                 285

His Ala Tyr Lys Glu His Asn Gly Thr Asn Leu Ile Glu Thr Lys Asn
290                 295                 300

Tyr Ala Leu Gly Ser Asp Ile Pro Glu Lys Cys Asp Thr Leu Ala Ser

```
                  305                 310                 315                 320
Asn Cys Phe Leu Ser Gly Asn Phe Asn Ile Glu Lys Cys Phe Gln Cys
                325                 330                 335

Ala Leu Leu Val Glu Lys Glu Asn Lys Asn Asp Val Cys Tyr Lys Tyr
            340                 345                 350

Leu Ser Glu Asp Ile Val Ser Asn Phe Lys Glu Ile Lys Ala Glu
        355                 360                 365

<210> SEQ ID NO 16
<211> LENGTH: 720
<212> TYPE: DNA
<213> ORGANISM: Plasmodium falciparum
<220> FEATURE:
<221> NAME/KEY: CDS
<222> LOCATION: (1)..(717)

<400> SEQUENCE: 16 atg aaa gat gaa aac aac tgc att tcg aac ctg cag gtg gaa gat cag      48
Met Lys Asp Glu Asn Asn Cys Ile Ser Asn Leu Gln Val Glu Asp Gln
 1               5                  10                  15 ggt aac tgc gat acc agc tgg atc ttc gct agc aag tat cat ctg gaa     96
Gly Asn Cys Asp Thr Ser Trp Ile Phe Ala Ser Lys Tyr His Leu Glu
                20                  25                  30 acc att cgt tgt atg aaa ggc tac gaa ccg act aaa atc tcc gcc ctc    144
Thr Ile Arg Cys Met Lys Gly Tyr Glu Pro Thr Lys Ile Ser Ala Leu
            35                  40                  45 tat gtg gcc aac tgt tat aaa ggc gaa cat aaa gat cga tgt gat gaa    192
Tyr Val Ala Asn Cys Tyr Lys Gly Glu His Lys Asp Arg Cys Asp Glu
        50                  55                  60 ggt tct agt ccc atg gaa ttt ctg caa att atc gaa gat tat ggc ttt    240
Gly Ser Ser Pro Met Glu Phe Leu Gln Ile Ile Glu Asp Tyr Gly Phe
    65                  70                  75                  80 ctg ccg gcg gaa tct aac tat ccg tat aac tat gta aaa gtt ggc gaa    288
Leu Pro Ala Glu Ser Asn Tyr Pro Tyr Asn Tyr Val Lys Val Gly Glu
                    85                  90                  95 cag tgt ccg aag gtt gaa gat cac tgg atg aac ctt tgg gat aac ggc    336
Gln Cys Pro Lys Val Glu Asp His Trp Met Asn Leu Trp Asp Asn Gly
                100                 105                 110 aag atc ttg cat aac aaa aac gaa ccg aat agc ctg gat ggt aag ggc    384
Lys Ile Leu His Asn Lys Asn Glu Pro Asn Ser Leu Asp Gly Lys Gly
            115                 120                 125 tat acc gcg tac gaa agc gag cgt ttt cac gat aac atg gac gcg ttt    432
Tyr Thr Ala Tyr Glu Ser Glu Arg Phe His Asp Asn Met Asp Ala Phe
        130                 135                 140 gtt aaa att att aaa acc gaa gtg atg aac aaa ggt tct gtg atc gcg    480
Val Lys Ile Ile Lys Thr Glu Val Met Asn Lys Gly Ser Val Ile Ala
145                 150                 155                 160 tat atc aaa gcg gaa aac gtg atg ggt tac gaa ttc agc ggc aag aaa    528
Tyr Ile Lys Ala Glu Asn Val Met Gly Tyr Glu Phe Ser Gly Lys Lys
                165                 170                 175 gtg caa aac ctg tgc ggc gat gat acg gct gat cat gca gtt aac att    576
Val Gln Asn Leu Cys Gly Asp Asp Thr Ala Asp His Ala Val Asn Ile
                180                 185                 190 gtg ggt tac ggc aac tat gta aac tca gaa ggt gaa aaa aag tca tac    624
Val Gly Tyr Gly Asn Tyr Val Asn Ser Glu Gly Glu Lys Lys Ser Tyr
            195                 200                 205 tgg atc gtg cgt aac tct tgg ggc ccg tac tgg ggc gat gaa ggt tat    672
Trp Ile Val Arg Asn Ser Trp Gly Pro Tyr Trp Gly Asp Glu Gly Tyr
        210                 215                 220 ttt aaa gtc gac atg tac ggc ccg acc cac tgc cat atc gaa ttc tag   720
```

```
Phe Lys Val Asp Met Tyr Gly Pro Thr His Cys His Ile Glu Phe
225                 230                 235
```

<210> SEQ ID NO 17

<211> LENGTH: 239
<212> TYPE: PRT
<213> ORGANISM: Plasmodium falciparum

<400> SEQUENCE: 17

```
Met Lys Asp Glu Asn Asn Cys Ile Ser Asn Leu Gln Val Glu Asp Gln
1               5                   10                  15

Gly Asn Cys Asp Thr Ser Trp Ile Phe Ala Ser Lys Tyr His Leu Glu
            20                  25                  30

Thr Ile Arg Cys Met Lys Gly Tyr Glu Pro Thr Lys Ile Ser Ala Leu
        35                  40                  45

Tyr Val Ala Asn Cys Tyr Lys Gly Glu His Lys Asp Arg Cys Asp Glu
    50                  55                  60

Gly Ser Ser Pro Met Glu Phe Leu Gln Ile Ile Glu Asp Tyr Gly Phe
65                  70                  75                  80

Leu Pro Ala Glu Ser Asn Tyr Pro Tyr Asn Tyr Val Lys Val Gly Glu
                85                  90                  95

Gln Cys Pro Lys Val Glu Asp His Trp Met Asn Leu Trp Asp Asn Gly
            100                 105                 110

Lys Ile Leu His Asn Lys Asn Glu Pro Asn Ser Leu Asp Gly Lys Gly
        115                 120                 125

Tyr Thr Ala Tyr Glu Ser Glu Arg Phe His Asp Asn Met Asp Ala Phe
    130                 135                 140

Val Lys Ile Ile Lys Thr Glu Val Met Asn Lys Gly Ser Val Ile Ala
145                 150                 155                 160

Tyr Ile Lys Ala Glu Asn Val Met Gly Tyr Glu Phe Ser Gly Lys Lys
                165                 170                 175

Val Gln Asn Leu Cys Gly Asp Asp Thr Ala Asp His Ala Val Asn Ile
            180                 185                 190

Val Gly Tyr Gly Asn Tyr Val Asn Ser Glu Gly Glu Lys Lys Ser Tyr
        195                 200                 205

Trp Ile Val Arg Asn Ser Trp Gly Pro Tyr Trp Gly Asp Glu Gly Tyr
    210                 215                 220

Phe Lys Val Asp Met Tyr Gly Pro Thr His Cys His Ile Glu Phe
225                 230                 235
```

<210> SEQ ID NO 18
<211> LENGTH: 1149
<212> TYPE: DNA
<213> ORGANISM: Plasmodium falciparum
<220> FEATURE:
<221> NAME/KEY: CDS
<222> LOCATION: (1)..(1146)

<400> SEQUENCE: 18

```
atg aaa tct tat att tct ctg ttt ttc atc ctg tgt gta ata ttc aac      48
Met Lys Ser Tyr Ile Ser Leu Phe Phe Ile Leu Cys Val Ile Phe Asn
1               5                   10                  15 aaa aac gtg atc aaa tgt acc ggt gaa agc cag acc ggt aat acc ggc      96
Lys Asn Val Ile Lys Cys Thr Gly Glu Ser Gln Thr Gly Asn Thr Gly
            20                  25                  30 ggt ggt cag gca ggc aac acg gtt ggc gac cag gcg ggc tct acc ggc     144
Gly Gly Gln Ala Gly Asn Thr Val Gly Asp Gln Ala Gly Ser Thr Gly
```

-continued

```
              35                  40                  45
ggc tct ccg cag ggt agc aca ggc gcc agt caa ccc ggc tct agc gaa    192
Gly Ser Pro Gln Gly Ser Thr Gly Ala Ser Gln Pro Gly Ser Ser Glu
     50                  55                  60 ccg tct aac cca gtg tct tct ggc cat tct gtt agt acc gtt agc gtt    240
Pro Ser Asn Pro Val Ser Ser Gly His Ser Val Ser Thr Val Ser Val
 65                  70                  75                  80 agc cag acc agc acc tct tct gaa aaa caa gat acc att cag gtg aaa    288
Ser Gln Thr Ser Thr Ser Ser Glu Lys Gln Asp Thr Ile Gln Val Lys
                 85                  90                  95 tct gcg ctg ctg aaa gat tat atg ggt tta aaa gtt acg ggc ccg tgt    336
Ser Ala Leu Leu Lys Asp Tyr Met Gly Leu Lys Val Thr Gly Pro Cys
            100                 105                 110 aac gaa aat ttc atc atg ttc ctg gtt ccg cat att tat att gat gtg    384
Asn Glu Asn Phe Ile Met Phe Leu Val Pro His Ile Tyr Ile Asp Val
        115                 120                 125 gat acc gaa gat acc aat ata gag ctc cgt acc acc ctg aaa gaa acc    432
Asp Thr Glu Asp Thr Asn Ile Glu Leu Arg Thr Thr Leu Lys Glu Thr
    130                 135                 140 aac aac cgc atc tca ttt gaa tca aac agt ggt tca ctg gaa aaa aaa    480
Asn Asn Arg Ile Ser Phe Glu Ser Asn Ser Gly Ser Leu Glu Lys Lys
145                 150                 155                 160 aaa tat gtg aag ctt ccg tca aac ggc acc acc ggt gaa cag ggt tca    528
Lys Tyr Val Lys Leu Pro Ser Asn Gly Thr Thr Gly Glu Gln Gly Ser
                165                 170                 175 agt aca ggc acc gtt cgc ggc gat acc gaa ccg att tca cac tcg agt    576
Ser Thr Gly Thr Val Arg Gly Asp Thr Glu Pro Ile Ser His Ser Ser
            180                 185                 190 agc tct tcg tcc agt tca agc tcc tct agc tcg tca tct agc tcg tct    624
Ser Ser Ser Ser Ser Ser Ser Ser Ser Ser Ser Ser Ser Ser Ser Ser
        195                 200                 205 agc agt tca tcc agc agt tct agc tcg tcc tct agt tcc agc tca tcg    672
Ser Ser Ser Ser Ser Ser Ser Ser Ser Ser Ser Ser Ser Ser Ser Ser
    210                 215                 220 agc gaa agt ctt ccg gcg aat ggc ccg gat tcc ccg acc gtt aaa ccc    720
Ser Glu Ser Leu Pro Ala Asn Gly Pro Asp Ser Pro Thr Val Lys Pro
225                 230                 235                 240 ccg cgt aac ctg cag aac ata tgt gaa acc ggc aaa aac ttc aaa ctg    768
Pro Arg Asn Leu Gln Asn Ile Cys Glu Thr Gly Lys Asn Phe Lys Leu
                245                 250                 255 gtg gtg tat att aag gag aat aca tta atc att aaa tgg aaa gtg tac    816
Val Val Tyr Ile Lys Glu Asn Thr Leu Ile Ile Lys Trp Lys Val Tyr
            260                 265                 270 ggc gaa acc aaa gat acc acc gaa aat aac aaa gtg gac gta cgc aag    864
Gly Glu Thr Lys Asp Thr Thr Glu Asn Asn Lys Val Asp Val Arg Lys
        275                 280                 285 tat ctg att aac gaa aag gaa acc ccg ttt act agt att cta atc cat    912
Tyr Leu Ile Asn Glu Lys Glu Thr Pro Phe Thr Ser Ile Leu Ile His
    290                 295                 300 gca tat aaa gaa cat aat ggc acc aac ctg atc gaa act aaa aac tac    960
Ala Tyr Lys Glu His Asn Gly Thr Asn Leu Ile Glu Thr Lys Asn Tyr
305                 310                 315                 320 gcg ctg ggc tca gac att ccg gaa aaa tgt gat acc ctg gcg tcc aat   1008
Ala Leu Gly Ser Asp Ile Pro Glu Lys Cys Asp Thr Leu Ala Ser Asn
                325                 330                 335 tgc ttt ctg agt ggt aac ttt aac att gaa aaa tgc ttt cag tgc gcg   1056
Cys Phe Leu Ser Gly Asn Phe Asn Ile Glu Lys Cys Phe Gln Cys Ala
            340                 345                 350 ctg ctg gtg gaa aaa gaa aat aaa aac gac gtg tgt tac aaa tac cta   1104
```

```
Leu Leu Val Glu Lys Glu Asn Lys Asn Asp Val Cys Tyr Lys Tyr Leu
        355                 360                 365 agc gaa gat att gtg tct aat ttc aag gag atc aaa gcg gag taa        1149
Ser Glu Asp Ile Val Ser Asn Phe Lys Glu Ile Lys Ala Glu
        370                 375                 380

<210> SEQ ID NO 19
<211> LENGTH: 382
<212> TYPE: PRT
<213> ORGANISM: Plasmodium falciparum

<400> SEQUENCE: 19

Met Lys Ser Tyr Ile Ser Leu Phe Phe Ile Leu Cys Val Ile Phe Asn
 1               5                  10                  15

Lys Asn Val Ile Lys Cys Thr Gly Glu Ser Gln Thr Gly Asn Thr Gly
            20                  25                  30

Gly Gly Gln Ala Gly Asn Thr Val Gly Asp Gln Ala Gly Ser Thr Gly
        35                  40                  45

Gly Ser Pro Gln Gly Ser Thr Gly Ala Ser Gln Pro Gly Ser Ser Glu
    50                  55                  60

Pro Ser Asn Pro Val Ser Ser Gly His Ser Val Ser Thr Val Ser Val
65                  70                  75                  80

Ser Gln Thr Ser Thr Ser Ser Glu Lys Gln Asp Thr Ile Gln Val Lys
                85                  90                  95

Ser Ala Leu Leu Lys Asp Tyr Met Gly Leu Lys Val Thr Gly Pro Cys
            100                 105                 110

Asn Glu Asn Phe Ile Met Phe Leu Val Pro His Ile Tyr Ile Asp Val
        115                 120                 125

Asp Thr Glu Asp Thr Asn Ile Glu Leu Arg Thr Thr Leu Lys Glu Thr
    130                 135                 140

Asn Asn Arg Ile Ser Phe Glu Ser Asn Ser Gly Ser Leu Glu Lys Lys
145                 150                 155                 160

Lys Tyr Val Lys Leu Pro Ser Asn Gly Thr Thr Gly Glu Gln Gly Ser
                165                 170                 175

Ser Thr Gly Thr Val Arg Gly Asp Thr Glu Pro Ile Ser His Ser Ser
            180                 185                 190

Ser Ser Ser Ser Ser Ser Ser Ser Ser Ser Ser Ser Ser Ser Ser Ser
        195                 200                 205

Ser Ser Ser Ser Ser Ser Ser Ser Ser Ser Ser Ser Ser Ser Ser Ser
    210                 215                 220

Ser Glu Ser Leu Pro Ala Asn Gly Pro Asp Ser Pro Thr Val Lys Pro
225                 230                 235                 240

Pro Arg Asn Leu Gln Asn Ile Cys Glu Thr Gly Lys Asn Phe Lys Leu
                245                 250                 255

Val Val Tyr Ile Lys Glu Asn Thr Leu Ile Ile Lys Trp Lys Val Tyr
            260                 265                 270

Gly Glu Thr Lys Asp Thr Thr Glu Asn Asn Lys Val Asp Val Arg Lys
        275                 280                 285

Tyr Leu Ile Asn Glu Lys Glu Thr Pro Phe Thr Ser Ile Leu Ile His
    290                 295                 300

Ala Tyr Lys Glu His Asn Gly Thr Asn Leu Ile Glu Thr Lys Asn Tyr
305                 310                 315                 320

Ala Leu Gly Ser Asp Ile Pro Glu Lys Cys Asp Thr Leu Ala Ser Asn
                325                 330                 335

Cys Phe Leu Ser Gly Asn Phe Asn Ile Glu Lys Cys Phe Gln Cys Ala
```

```
                    340                 345                 350
Leu Leu Val Glu Lys Glu Asn Lys Asn Asp Val Cys Tyr Lys Tyr Leu
                355                 360                 365

Ser Glu Asp Ile Val Ser Asn Phe Lys Glu Ile Lys Ala Glu
        370                 375                 380

<210> SEQ ID NO 20
<211> LENGTH: 1058
<212> TYPE: DNA
<213> ORGANISM: Plasmodium falciparum

<400> SEQUENCE: 20
ttttcatatt gtgtgttata tttaacaaaa atgttataaa atgtacagga gaaagtcaaa      60
caggtaatac aggaggaggt caagcaggta atacagtagg agatcaagca ggtagtacag     120
gaggaagtcc acaaggtagt acgggagcaa gtcaacccgg aagttccgaa ccaagcaatc     180
ctgtaagttc cggacattct gtaagtactg tatcagtatc acaaacttca acttcttcag     240
aaaaacagga tacaattcaa gtaaaatcag ctttattaaa agattatatg ggtttaaaag     300
ttactggtcc atgtaacgaa aatttcataa tgttcttagt tcctcatata tatattgatg     360
ttgatacaga agatactaat atcgaattaa gaacaacatt gaaagaaaca aataatgcaa     420
tatcatttga atcaaacagt ggttcattag aaaaaaaaaa atatgtaaaa ctaccatcaa     480
atggtacaac tggtgaacaa ggttcaagta cgggaacagt tagaggagat acagaaccaa     540
tttcagattc aagctcaagt tcaagttcaa gttctagttc aagttcaagt tcaagttcta     600
gttcaagttc aagttcaagt tcaagttcta gttcaagttc tagttcaagt tcagaaagtc     660
ttcctgctaa tggacctgat tcccctactg ttaaaccgcc aagaaattta caaaatatat     720
gtgaaactgg aaaaaacttc aagttggtag tatatattaa ggagaataca ttaataatta     780
aatggaaagt atacggagaa acaaaagata ctactgaaaa taacaaagtt gatgtaagaa     840
agtatttgat aaatgaaaag gaaaccccat ttactagtat actaatacat gcgtataaag     900
aacataatgg aacaaactta atagaaagta aaaactacgc attaggatca gacattccag     960
aaaaatgtga taccttagct tccaattgct ttttaagtgg taattttaac attgaaaaat    1020
gctttcaatg tgctcttttta gtagaaaaag aaaataaa                           1058
```